United States Patent
Pulé et al.

(10) Patent No.: US 11,965,173 B2
(45) Date of Patent: Apr. 23, 2024

(54) PLASMID SYSTEM

(71) Applicant: AUTOLUS LIMITED, London (GB)

(72) Inventors: Martin Pulé, London (GB); Paulo Fernandes, London (GB); Hanna Kymalainen, London (GB); Ekaterini Kotsopoulou, London (GB)

(73) Assignee: AUTOLUS LIMITED, London (GB)

( * ) Notice: Subject to any disclaimer, the term of this patent is extended or adjusted under 35 U.S.C. 154(b) by 983 days.

(21) Appl. No.: 16/772,216

(22) PCT Filed: Dec. 14, 2018

(86) PCT No.: PCT/GB2018/053638
§ 371 (c)(1),
(2) Date: Jun. 12, 2020

(87) PCT Pub. No.: WO2019/116051
PCT Pub. Date: Jun. 20, 2019

(65) Prior Publication Data
US 2023/0242937 A1 Aug. 3, 2023

(30) Foreign Application Priority Data
Dec. 15, 2017 (GB) ...................................... 1720948

(51) Int. Cl.
*C12N 15/86* (2006.01)
*C12N 15/85* (2006.01)

(52) U.S. Cl.
CPC ............. *C12N 15/86* (2013.01); *C12N 15/85* (2013.01); *C12N 2740/13022* (2013.01); *C12N 2740/13043* (2013.01); *C12N 2740/13052* (2013.01); *C12N 2800/107* (2013.01)

(58) Field of Classification Search
CPC .................................. C12N 15/86; C12N 15/85
See application file for complete search history.

(56) References Cited

FOREIGN PATENT DOCUMENTS

| WO | WO-95/31566 A1 | 11/1995 |
|---|---|---|
| WO | WO-01/79518 A2 | 10/2001 |
| WO | WO-2013/153391 A1 | 10/2013 |
| WO | WO-2014/066700 A1 | 5/2014 |

OTHER PUBLICATIONS

International Search Report and Written Opinion from International Application No. PCT/GB2018/053638 dated Apr. 10, 2019.
Li et al., "A codon-shuffling method to prevent reversion during production of replication-defective herpesvirus stocks: Implications for herpesvirus vaccines," Scientific Reports 7(1), 9 pages (2017).
Sheridan et al., "Generation of Retroviral Packaging and Producer Cell Lines for Large-Scale Vector Production and Clinical Application: Improved Safety and High Titer," Molecular Therapy 2(3):262-275 (2000).
Shin et al., "Construction of a retroviral vector production system with the minimum possibility of a homologous recombination," Gene Therapy 10(8):706-711 (2003).
Soneoka et al., "A transient three-plasmid expression system for the production of high titer retroviral vectors," Nucleic Acids Res. 23(4):628-633 (1995).
Zucchelli et al., "Codon Optimization Leads to Functional Impairment of RD114-TR Envelope Glycoprotein," Mol Ther Methods Clin Dev. 4:102-114 (2017).

*Primary Examiner* — Amy E Juedes
*Assistant Examiner* — Peter Johansen
(74) *Attorney, Agent, or Firm* — MARSHALL, GERSTEIN & BORUN LLP

(57) ABSTRACT

There is provided a plasmid system for transfection into a cell to create a producer cell, the system comprising: a. a helper plasmid comprising a first nucleotide sequence encoding Murine leukemia virus (MLV)-derived Gag and Pol poly-proteins; b. an envelope plasmid comprising a second nucleotide sequence encoding an Env protein; c. a genome plasmid comprising a third nucleotide sequence encoding a retroviral genome, wherein the first nucleotide sequence is codon-shuffled to remove any significant regions of homology with the third nucleotide sequence; and wherein the second nucleotide sequence is codon-optimised for expression in the producer cell.

9 Claims, 11 Drawing Sheets

Specification includes a Sequence Listing.

| Tube | Envelope Plasmid | µg | Titre | STDEV |
|---|---|---|---|---|
| 1 | pcDNA3.1.GALVenv | low | 7.11E+04 | 4.61E+03 |
| 2 | pcDNA3.1.GALVenv | high | 7.48E+04 | 3.96E+03 |
| 3 | pcDNA3.1.GALVenv | standard | 3.62E+05 | 4.34E+04 |
| 4 | pSF_Ferritin_mEF1α_optGALV | low | 1.33E+05 | 1.46E+04 |
| 5 | pSF_Ferritin_mEF1α_optGALV | standard | 7.93E+05 | 1.41E+05 |
| 6 | pSF_Ferritin_mEF1α_optGALV | high | 1.51E+06 | 4.46E+05 |

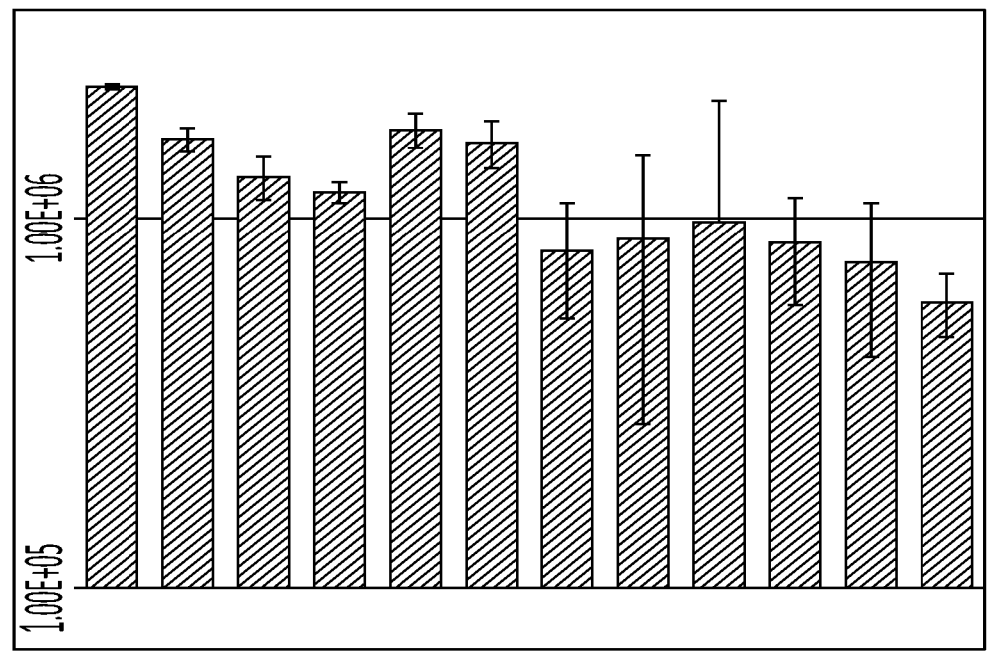

| Tube | GAGPOL/ENV plasmids | Ratio | Titre 01/04 | Titre 01/04 | Average | STDEV |
|---|---|---|---|---|---|---|
|  | pSF_CMV_BGIntron_wtGAGPOL |  |  |  |  |  |
| 1 | pSF_Ferritin_mEF1α_optRD114 | SL | 2.31E+06 | 2.23E+06 | 2.27E+06 | 57700 |
| 2 | pGEN1 | LL | 1.65E+06 | 1.63E+06 | 1.64E+06 | 13011 |
| 3 | pSF_CMV_shufGAGPOL | SS | 1.38E+06 | 1.22E+06 | 1.30E+06 | 111016 |
| 4 | pSF_Ferritin_mEF1α_optRD114 | SL | 7.24E+05 | 1.63E+06 | 1.18E+06 | 640214 |
| 5 | pGEN1 | LS | 1.79E+06 | 1.68E+06 | 1.74E+06 | 74105 |
| 6 |  | LL | 1.36E+06 | 1.85E+06 | 1.60E+06 | 345068 |
| 7 | pSF_CAG_shufGAGPOL | SS | 6.89E+05 | 9.45E+05 | 8.17E+05 | 180736 |
| 8 | pSF_Ferritin_mEF1α_optRD114 | SL | 9.47E+05 | 8.13E+05 | 8.80E+05 | 94752 |
| 9 | pGEN1 | LS | 8.65E+05 | 1.09E+06 | 9.78E+05 | 160230 |
| 10 |  | LL | 8.13E+05 | 9.04E+05 | 8.59E+05 | 64064 |
| 11 | pSF_p565Prom_shufGAGPOL | SL | 8.72E+05 | 6.48E+05 | 7.60E+05 | 158675 |
| 12 | pSF_CMV_BGIntron_wtRD114 | LL | 5.92E+05 | 5.92E+05 | 5.92E+05 | 566 |
|  | pGEN1 |  |  |  |  |  |

PLASMID SYSTEM

CROSS-REFERENCE TO RELATED APPLICATIONS

This is a U.S. National Phase of International Application No. PCT/GB2018/053638, filed Dec. 14, 2018, which claims priority to Great Britain Application No. 1720948.7, filed Dec. 15, 2017.

FIELD OF INVENTION

The present invention relates to a plasmid system which may be used to create a producer cell for producing retroviral vectors. The invention also relates to methods for increasing the efficiency of retroviral vectors using such a plasmid system.

BACKGROUND

Retroviral vectors are used for several applications including ex vivo modification of T cells for cancer immunotherapies.

Retroviral vectors may be made by transient transfection using a three plasmid system:

i) a helper plasmid containing the viral sequences encoding Gag and Pol polyproteins; (ii) an envelope plasmid coding for the envelope protein (Env); and (iii) a genome plasmid containing the transgene flanked by viral Long Terminal Repeats (LTRs) and a packaging signal required for the incorporation of the viral vector RNA into virions.

It is desirable to maximise the efficiency of viral vector production in order to obtain high retroviral titres and to reduce the total amount of plasmid needed for transient transfection.

DESCRIPTION OF THE FIGURES

FIG. 8: Titration results of independent vector preparations in 10 cm plates made using different helper and envelope plasmids at different ratios. The ratios are designated "standard" or "low" (¼ of standard). "SS"=Standard helper and envelope, "SL"=standard helper, low envelope; "LS"=Low helper, standard envelope; "LL"=Low helper and envelope. pGEN1, genome plasmid 1.

SUMMARY OF ASPECTS OF THE INVENTION

Figure 1:
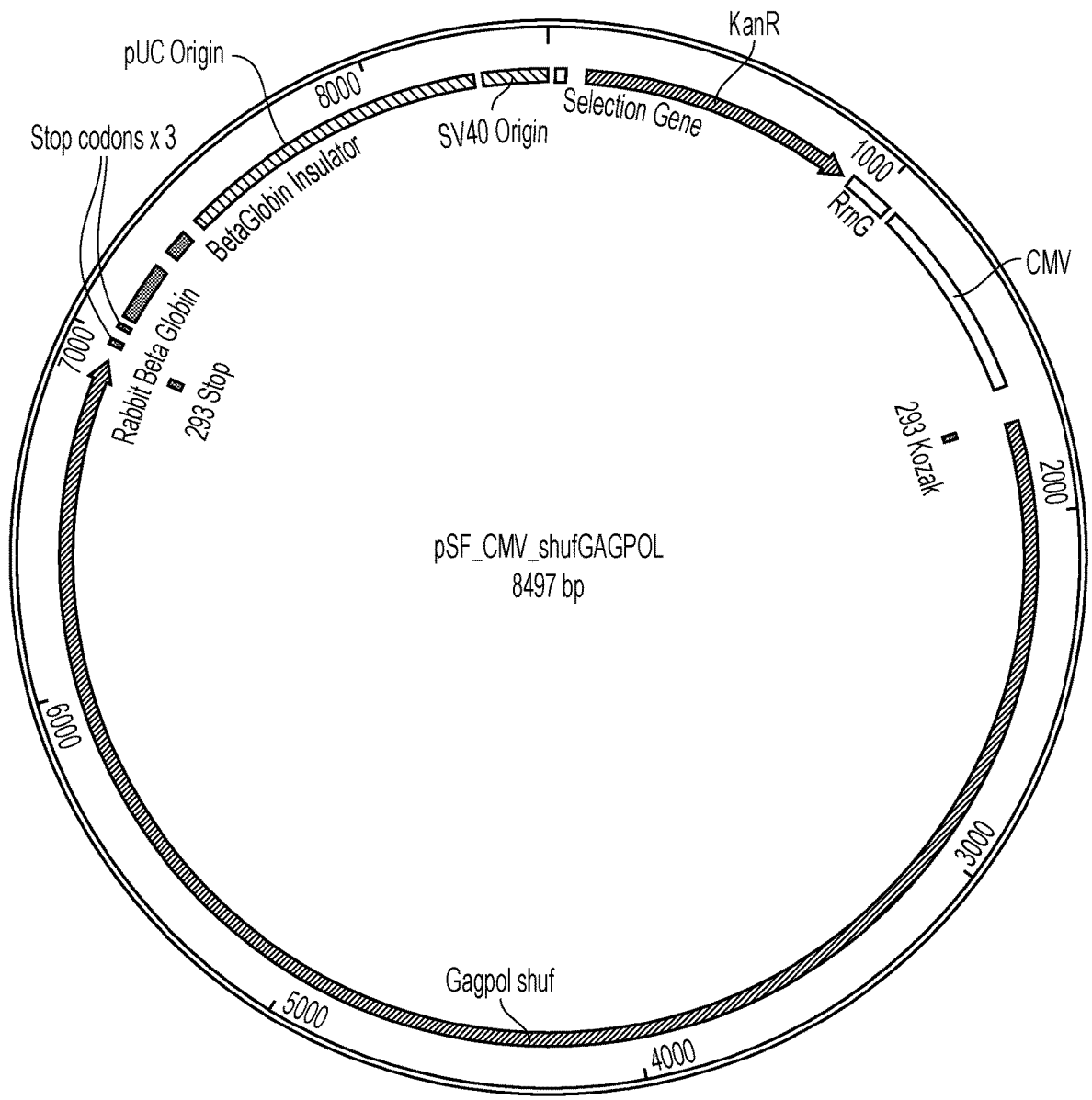
FIG. 1: Map of a helper plasmid of the plasmid system of the present invention

The present invention is based on the finding that it is possible to improve the system for creating a producer cell for producing retroviral vectors with plasmids comprising novel modifications at the nucleic acid level. These modifications have been found to improve the titre and safety profile of the viral vectors as well as increasing the efficiency of the producer cell itself.

Thus in a first aspect, the present invention provides a plasmid system for transfection into a cell to create a producer cell, the system comprising:

a. a helper plasmid comprising a first nucleotide sequence encoding Murine leukemia virus (MLV)-derived Gag and Pol poly-proteins;

b. an envelope plasmid comprising a second nucleotide sequence encoding an Env protein;

c. a genome plasmid comprising a third nucleotide sequence encoding a retroviral genome, wherein the first nucleotide sequence is codon-shuffled to remove any significant regions of homology with the third nucleotide sequence; and wherein the second nucleotide sequence is codon-optimised for expression in the producer cell.

The first nucleotide sequence may be codon optimised for expression in the producer cell.

The codon adaptation index (CAI) of the first nucleotide sequence may be at least 0.75.

The first nucleotide sequence may comprise a sequence selected from SEQ ID NO: 1, SEQ ID NO: 2 or SEQ ID NO: 3.

The helper plasmid may comprise a promoter selected from: CMV early enhancer/chicken β actin (CAG) or cytomegalovirus (CMV).

The helper plasmid may comprise a rabbit β-globin polyA site.

The helper plasmid may further comprise an intron sequence in the 5′ untranslated region. The intron may be a (human β-globin) intron.

The helper plasmid may lack a long terminal repeat (LTR) sequence.

The second nucleotide sequence of the first aspect may comprises the sequence selected from SEQ ID NO: 7, SEQ ID NO: 8, SEQ ID NO: 9, SEQ ID NO: 10, SEQ ID NO: 11 or SEQ ID NO: 12.

The Env protein may be the RD114 Envelope protein or the GALV Envelope protein.

For example, when the Env protein is the RD114 Envelope protein, the codon adaptation index (CAI) of the second nucleotide sequence is at least 0.75.

Alternatively, when the Env protein is GALV Envelope protein, the codon adaptation index (CAI) of the second nucleotide sequence is at least 0.65.

The envelope plasmid may comprise a promoter selected from: Ferritin and cytomegalovirus (CMV) promoters.

The envelope plasmid may comprise a SV40 polyA site.

The envelope plasmid may further comprises an intron sequence in the 5' untranslated region. The intron of the envelope plasmid may be a BG (human β-globin), RD114 or mEf1 (murine elongation factor 1) intron.

The envelope plasmid may lack a long terminal repeat (LTR) sequence.

The helper plasmid and the envelope plasmid may comprise different promoters.

The helper plasmid and the envelope plasmid may comprise different polyA sites.

The helper plasmid and envelope plasmid may comprise different introns.

The genome plasmid of the first aspect of the invention may further comprise a nucleotide of interest (NOI).

The genome plasmid may comprise a packaging signal, which has homology with a portion of the wildtype MLV nucleotide sequence encoding Gag and/or Pol polyprotein(s).

In a second aspect, the present invention provides a method for making a packaging cell, which packages retroviral vectors, which comprises the step of transfecting a cell with a helper plasmid and an envelope plasmid as defined in the first aspect of the invention.

In a third aspect, the present invention provides a method for making a producer cell, which produces retroviral vectors, which comprises the step of transfecting a cell with a helper plasmid, an envelope plasmid and a genome plasmid, as defined in the first or second aspect of the invention.

In a fourth aspect, the present invention provides a packaging cell capable of packaging retroviral vectors, comprising a helper plasmid and an envelope plasmid, as defined in the first aspect of the invention.

In a fifth aspect, the present invention provides a producer cell capable of producing retroviral vectors, comprising a helper plasmid, an envelope plasmid and a genome plasmid, as defined in the first or second aspect of the invention.

In a sixth aspect, the present invention provides a method for making a retroviral vector using a packaging cell as defined in the fourth aspect of the invention, or a producer cell as defined in the fifth aspect of the invention.

In a seventh aspect, the present invention provides a method to increase efficiency of a producer cell of a plasmid system, the system comprising:
a. a helper plasmid comprising a first nucleotide sequence encoding MLV-derived Gag and Pol poly-proteins;
b. an envelope plasmid comprising a second nucleotide sequence encoding an Env protein;
c. a genome plasmid comprising a third nucleotide sequence encoding a retroviral genome, characterised in that the method comprises the steps of:
(I) codon-shuffling the first nucleotide sequence to remove significant regions of homology with the third nucleotide sequence;
(II) codon-optimising the second nucleotide sequence for expression in the producer cell.

In an eighth aspect, the present invention provides a nucleotide sequence encoding MLV-derived Gag and Pol poly-proteins comprising the sequence selected from: SEQ ID NO: 1 to SEQ ID NO: 3.

In a ninth aspect, the present invention provides a nucleotide sequence encoding Env protein comprising the sequence selected from: SEQ ID NO: 5 to SEQ ID NO: 7 and SEQ ID NO: 9 to 11.

The inventors found that codon shuffling the Gag and Pol polyprotein encoding sequence and codon-optimising the Env sequence not only improves safety but has a synergistic effect in improving vector titre.

It has previously been reported that codon optimisation of Env-encoding sequences leads to a non-functional Env due to impaired glycosylation of the precursor protein, so it is surprising that codon optimised Env-encoding sequences a) encode a functional protein and b) in combination with a codon-shuffled GagPol-encoding sequence leads to increased efficiency of gene expression.

DETAILED DESCRIPTION

Retroviruses

Retroviruses are double stranded RNA enveloped viruses mainly characterized by the ability to "reverse-transcribe" their genome from RNA to DNA. Virions measure 100-120 nm in diameter and contain a dimeric genome of identical positive RNA strands complexed with the nucleocapsid proteins. The genome is enclosed in a protein capsid that also contains enzymatic proteins, namely the reverse transcriptase, the integrase and proteases, required for viral infection. Matrix proteins form a layer outside the capsid core that interacts with the envelope, a lipid bilayer derived from the host cellular membrane, which surrounds the viral core particle. Anchored on this bilayer, are the viral envelope glycoproteins responsible for recognizing specific receptors on a host cell and initiating the infection process. These envelope proteins are formed by two subunits: the transmembrane (TM) that anchors the protein into the lipid membrane and the surface (SU) which binds to the cellular receptors.

Based on the genome structure, retroviruses are classified into simple retrovirus such as MLV (murine leukemia virus); or complex retrovirus such as HIV or EIAV.

Retroviruses encode three genes: gag-pro (group specific antigen-protease), gag-pro-pol (group specific antigen-protease-polymerase) by read through of a stop codon and env (envelope). The gag sequence encodes the three main structural proteins: the matrix protein, nucleocapsid proteins, and capsid protein. The pro sequence encodes proteases responsible for cleaving Gag and Gag-Pol during particle assembly, budding and maturation. The pol sequence encodes the enzymes reverse transcriptase and integrase, the former catalyzing the reverse transcription of the viral genome from RNA to DNA during the infection process and the latter responsible for integrating the proviral DNA into the host cell genome.

In addition to gag, pol and env, complex retroviruses, such as lentiviruses, have accessory genes including vif, vpr, vpu, nef, tat and rev that regulate viral gene expression, assembly of infectious particles and modulate viral replication in infected cells.

During the process of infection, a retrovirus initially attaches to a specific cell surface receptor via the envelope glycoprotein. On entry into the susceptible host cell, the retroviral RNA genome is then copied to DNA by the virally encoded reverse transcriptase in the host cell cytoplasm. This DNA is transported to the host cell nucleus where it subsequently integrates into the host genome. At this stage, it is typically referred to as the provirus. The provirus is stable in the host chromosome during cell division and is transcribed like other cellular proteins. The provirus encodes the proteins and packaging machinery required to make more virus, which can leave the cell by a process known as "budding".

When enveloped viruses, such as retrovirus and lentivirus, bud out of the host cells, they take part of the host cell lipid bilayer membrane. In this way, host-cell derived membrane proteins become part of the retroviral particle.

The present invention utilises this process of infection in order to introduce proteins of interest into the genome of the host cell.

Retroviral Vectors

Retroviruses and lentiviruses may be used as a carrier, vector or delivery system for the transfer of a nucleotide sequence of interest (NOI), or a plurality of NOIs, to a target cell. The transfer can occur in vitro, ex vivo or in vivo. When used in this fashion, the viruses are typically called viral vectors. Viral vectors of the present invention may comprise a NOI(s), which may encode a T cell receptor or a chimeric antigen receptor and/or a suicide gene.

Gamma-retroviral vectors, commonly designated retroviral vectors, were the first viral vector employed in gene therapy clinical trials in 1990 and are still one of the most used. More recently, the interest in a sub-family of retroviral vectors, i.e. lentiviral vectors, derived from complex retroviruses such as the human immunodeficiency virus (HIV), has grown due to their ability to transduce non-dividing cells. The most attractive features of retroviral and lentiviral vectors as gene transfer tools include the capacity for large genetic payload (up to 9 kb), minimal patient immune response, high transducing efficiency in vivo and in vitro, and the ability to permanently modify the genetic content of the target cell, sustaining a long-term expression of the delivered gene. While both lentiviruses and gamma-retroviruses may use the same gene products for packaging (i.e., Gag, Pol, and Env), the isoforms of these proteins differ so they are not interchangeable. General envelope plasmids, such as VSV-G, however, may be used across both systems.

The retroviral vector may be based on any suitable retrovirus which is able to deliver genetic information to eukaryotic cells. For example, the retroviral vector may be an alpharetroviral vector, a gammaretroviral vector, a lentiviral vector or a spumaretroviral vector. Such vectors have been used extensively in gene therapy treatments and other gene delivery applications. Retroviral vectors are commonly produced by transfection of a packaging target cell line such as Human Embryonic Kidney 293 (HEK293) cells, using a three-plasmid system.

Described herein is such a plasmid system for triple transfection into a cell to create a producer cell for the manufacture of a retroviral vector. Also described is a plasmid system for double transfection into a cell to create a stable packaging cell.

Triple Transfection

The transient three-plasmid system for the production of high titre retroviral vectors has previously been described (see, for example, Soneoka et al.; Nucleic Acids Res. 1995; 23(4); 628-633). This system is used to create a producer cell in the first aspect of the invention and involves three separate plasmids:

a) a helper plasmid comprising a first nucleotide sequence encoding MLV-derived Gag and Pol poly-proteins;
b) an envelope plasmid comprising a second nucleotide sequence encoding an Env protein; and
c) a genome plasmid comprising a third nucleotide sequence encoding a retroviral genome.

This system is a convenient method for rapid analysis of encoding components within each plasmid (such as the MLV-derived Gag and Pol or Env proteins), and is simple and reproducible in the hands of different operators compared to a single plasmid transfection method. This is because in addition to being a helper virus-free method, the triple transfection protocol offers the flexibility to adapt the packaging components and exogenous regulatory elements in the plasmid. Triple transfection is widely used in research grade vector core facilities and has been used for the manufacturing of clinical grade preparations for phase one trials.

Replication Competent Retrovirus

The three plasmids in the plasmid system of the present invention are used for vector production by transient transfection, and thus are designed to be present in the nucleus of the producer cells at the same time. Sequence homology between different DNA molecules that are present in the nucleus at the same time may result in homologous recombination between the DNA molecules, and the generation of recombinant DNA. For example, RCR has been reported in murine producer cell lines PA317, AM12 and Psi-CRIP.

Homologous recombination is a type of genetic recombination in which nucleotide sequences are exchanged between two similar or identical molecules of DNA. If DNA recombines in such a way as to bring together the viral helper packaging compenents (Gag and Pol polyproteins), the envelope (Env) and the LTRs/packaging signal of the three separate plasmids, production of partially or fully replication competent recombinant retroviruses may result. Infection with these type of retroviruses can cause malignant diseases as well as well as a range of other unsafe pathogenic states.

The most efficient way to avoid the risk of generation of recombinant retrovirus, potentially capable of replication, is to ensure that no sequence homology between the plasmids exists.

The nucleic acid sequence comprised within the genome plasmid that encodes the wild type retroviral genome may have portion(s) of sequence homology with the nucleic acid sequence of the helper plasmid that encodes the wild type Gag and Pol polyproteins. For example, the packaging signal of the retroviral genome may have a portion of sequence which shows homology with the nucleic acid sequence encoding the Gag and pol polyprotein. The helper plasmid may also share sequence homology between other exogenous elements in the envelope or genome plasmids, such as the promoter, the intron, the polyA sequence and/or the LTR sequences. This further increases a risk of generation of replication-competent retrovirus (RCR) via homologous recombination during transfection.

The standard 3-plasmid system therefore features limitations relating to the safety as well as efficiency of the system to create a producer cell for creating retroviral vector. To overcome these issues, the present inventors have optimised the plasmid system by re-designing the standard plasmids to improve gene expression by a combination of several approaches;

I. Sequence modification of the Gag and Pol polyprotein by codon-shuffling to improve the safety profile of the plasmid combination by removal of the homologous regions with the packaging signal sequence in the genome plasmid; and
II. Codon optimising the Env coding sequences to improve translation efficiency and mRNA stability; and/or
III. Introduction of new efficient promoters to enhance transcription; and/or;
IV. Introduction of new strong polyadenylation sites to improve mRNA stability; and/or
V. Utilise introns at the 5' untranslated region to enhance mRNA export from the nucleus to the cytoplasm.

Further additions to the new plasmids may include the SV40 origin of replication, which results in increased plasmid copy number during transfection if carried out in 293T cells which express the SV40 large T antigen. The antibiotic resistance marker may also be changed from ampicillin to kanamycin to improve the clinical safety profile of the plasmids.

The inventors have designed a three-plasmid system where not one of the regulatory elements present in each of the separate plasmids described herein are the same. For example, the helper plasmid, the envelope plasmid and the genome plasmid all comprise different promoters.

Re-Designing Plasmids

Codon-Shuffling

The present inventors have discovered that it is possible to create a helper plasmid comprising the packaging components with completely novel sequences and reduced homology to the viral genome plasmid comprising a packaging signal.

Codon shuffling, also known as codon-wobbling, is a process whereby the amino acid sequence is preserved for a given coding sequence, but alternative codons are used due to the degeneracy of the genetic code. Importantly, this type of synthetic manipulation to alter codon distribution in a viral gene effectively changes the nucleotide sequence in a gene of interest without altering the amino acid sequence. In addition, the genetic deck can be manipulated to change any number of variables to potentially increase or decrease protein levels, a consideration for viral gene products that are toxic to the host cell.

Retrovirus genomes can undergo homologous recombination (HR) during replication, which may lead to wild-type (WT) reversion during complementation of replication-defective and attenuated viruses via HR with the helper gene provided in trans. To avoid this safety-risk, the present invention employs a synthetic-biology approach based on a technique known as codon shuffling. Computer-assisted algorithms may be used to redistribute codons in a helper plasmid, thereby eliminating regions of homology with the genome plasmid, while enabling manipulation of factors such as codon-pair bias and CpG content to effectively titrate helper-gene protein levels. The present inventors apply this technique to avoid homologous replication between the retroviral genome and the sequences encoding MLV-derived gag and pol polyproteins.

Codon-Optimisation

There may be species-specific codon usage bias between the host and the target cell which may affect the efficiency of the system. One powerful strategy to overcome codon-usage bias is codon-optimisation.

Codon optimisation is a method of enhancing gene expression by making the translation process more efficient. Due to the redundant nature of the DNA code, many amino acids can be coded for by several different triplets. These triplets are transcribed into messenger RNA (mRNA) and then translated into amino acids to make polypeptides. The translation process features the binding of a transfer RNA (tRNA) containing the complementary triplet to the one present on the mRNA molecule, and by doing that the amino acid associated with that tRNA is added onto the growing polypeptide.

The abundance of the different tRNAs varies between organisms. Therefore, the speed at which an amino acid is added to the polypeptide depends on whether the triplet coding for it is abundant or rare in that particular species. The abundance of different codons for several different organisms is documented on publicly available databases such as the codon usage database, and therefore it is possible to change the DNA sequence of a gene by utilising abundant codons without changing the amino acid sequence, resulting in more efficient translation and thus enhanced gene expression.

Recently, one group attempted to codon-optimise a sequence of an Env protein (RD114) but showed that it lead to functional impairment of the protein (Zucchelli et al.; Mol Ther Methods Clin Dev. 2017; 4: 102-114). However, the present inventors found that not only did the Env protein of the present invention remain functional, but the combination of such a modified envelope plasmid with the codon-shuffled GagPol-encoding sequence of the helper plasmid showed a synergistic effect with increased efficiency of gene expression. Notably, the CAI of the codon-optimised RD114 Env protein significantly increased from 0.66 to 0.75.

In one embodiment described herein, the nucleotide sequence encoding the Gag and Pol polyprotein may be codon-optimised.

Codon-Optimisation Index (CAI)

The codon adaptation index (CAI) is a widespread technique for analysing codon usage bias. CAI measures the deviation of a given protein coding gene sequence with respect to a reference set of genes.

The reference set in CAI is composed of highly expressed genes, so that CAI provides an indication of gene expression level under the assumption that there is translational selection to optimise gene sequences according to their expression levels.

CAI is defined as the geometric mean of the weight associated to each codon over the length of the gene sequences (measured in codons). For each amino acid sequence, the weight of each of its codons, in CAI is computed from the reference set, as the ratio between the observed frequency of the codon, and the frequency of the most frequent synonymous codon for that amino acid.

The present invention may provide an increase in CAI for both the first nucleotide sequence comprised within the helper plasmid and the second nucleotide sequence comprised with the envelope plasmid. In one aspect of the invention, the first nucleotide sequence, which encodes packaging components Gag and Pol polyproteins is increased to over 0.75.

The CAI of the second nucleotide sequence which encodes the Env protein similarly increased to over 0.75. In another embodiment, the CAI the second nucleotide sequence, which encoded a differently derived Env protein, is increased to over 0.65.

i) Helper Plasmid

The helper plasmid (FIG. 1), also known as the packaging plasmid, comprises a nucleotide sequence encoding Gag and Pol polyproteins described herein. Notably, in the triple plasmid system, the Gag and Pol polyproteins packaging components are on a separate plasmid to the Env protein. Placing the packaging genes on separate plasmids helps to reduce the formation of replication-competent virus.

The helper plasmid may also comprise exogenous regulatory elements such as, for example at least one stop codon, a promoter sequence, an intron sequence and/or a polyA sequence.

Examples of promoter sequences of the helper plasmid described herein include, but are not limited to, CMV early enhancer/chicken β actin (CAG), cytomegalovirus (CMV) or p565Prom sequence.

An example of an intron sequence of the helper plasmid described herein includes, but is not limited to, human β-globin intron in the 5' untranslated region of the plasmid.

An example of a polyA sequence of the helper plasmid described herein includes, but is not limited to, the rabbit β-globin polyA sequence. This polyA sequence is selected due to its relative strength. The inclusion of a strong polyadenylation signal at the end of the expression cassette is important for the efficient termination of transcription. It increases gene expression levels by allowing the RNA polymerase to detach from the completed mRNA and begin again to transcribe a new mRNA molecule. Expression levels are further increased as the polyA tail promotes mRNA export from the nucleus, initiation of translation, and protects the mRNA from degradation.

The helper plasmid may further comprise a nucleotide sequence encoding a SV40 origin of replication which results in increased copy number and increase plasmid retention in transfected cells and thus improve vector titre. The helper plasmid may further comprise an antibiotic resistance marker. For example, the helper plasmid may comprise the marker kanamycin, which has shown improved clinical safety profile of plasmids compared to the standard ampicillin marker.

In one embodiment, the LTR sequence of the helper plasmid may be removed to reduce portions of shared sequence homology with the LTR sequences present in any one of the other plasmids of the three-plasmid system, such as the envelope plasmid and/or the genome plasmid.

In particular, provided herein is a helper plasmid comprising MLV-derived Gag and Pol polyproteins, the nucleic acid sequence of which has been codon shuffled, as described herein.

MLV-Derived GAG and POL Polyproteins

The present invention provides Gag and Pol polyproteins derived from Murine Leukemia virus (MLV). MLVs (or MuLVs) are retroviruses with an ability to cause cancer in murine hosts. The murine leukemia viruses are type VI retrovirus and belong to the gammaretroviral genus of the Retroviridae family.

Moloney, Rauscher, Abelson and Friend strains of MLVs are commonly used in cancer research. In one embodiment, the Gag and Pol polyproteins of the helper plasmid are Moloney-MLV derived Gag and pol polyproteins.

Importantly, the nucleotide sequence encoding the MLV-derived Gag and Pol polyproteins of the helper plasmid of the present invention have been codon-shuffled to remove any significant regions of homology with the packaging signal in the genome plasmid.

The nucleotide sequence of the MLV-derived Gag and Pol polyproteins packaging component has a relatively good codon-usage, compared to, for example, HIV-derived Gag and Pol polyproteins. However, the present inventors have shown that it is possible to codon shuffle the nucleotide sequence encoding the MLV-derived Gag and Pol polyproteins in order to avoid homologous recombination but still retain good translation efficiency.

ii) Envelope Plasmid

The envelope plasmid comprises a nucleotide sequence encoding the Env protein as well as regulatory exogenous elements, such as, a promoter, an intron sequence and/or a polyA sequence. Other exogenous elements may include a SV40 origin of replication and a marker such as an antibiotic resistance marker.

Examples of promoter sequences of the envelope plasmid described herein include but are not limited Ferritin, cytomegalovirus (CMV) or PDXG3 promoters.

An example of an intron sequence of the envelope plasmid described herein includes, but is not limited to, BGIntron, RD114 or mEf1 intron in the 5' untranslated region of the plasmid.

Figure 2:
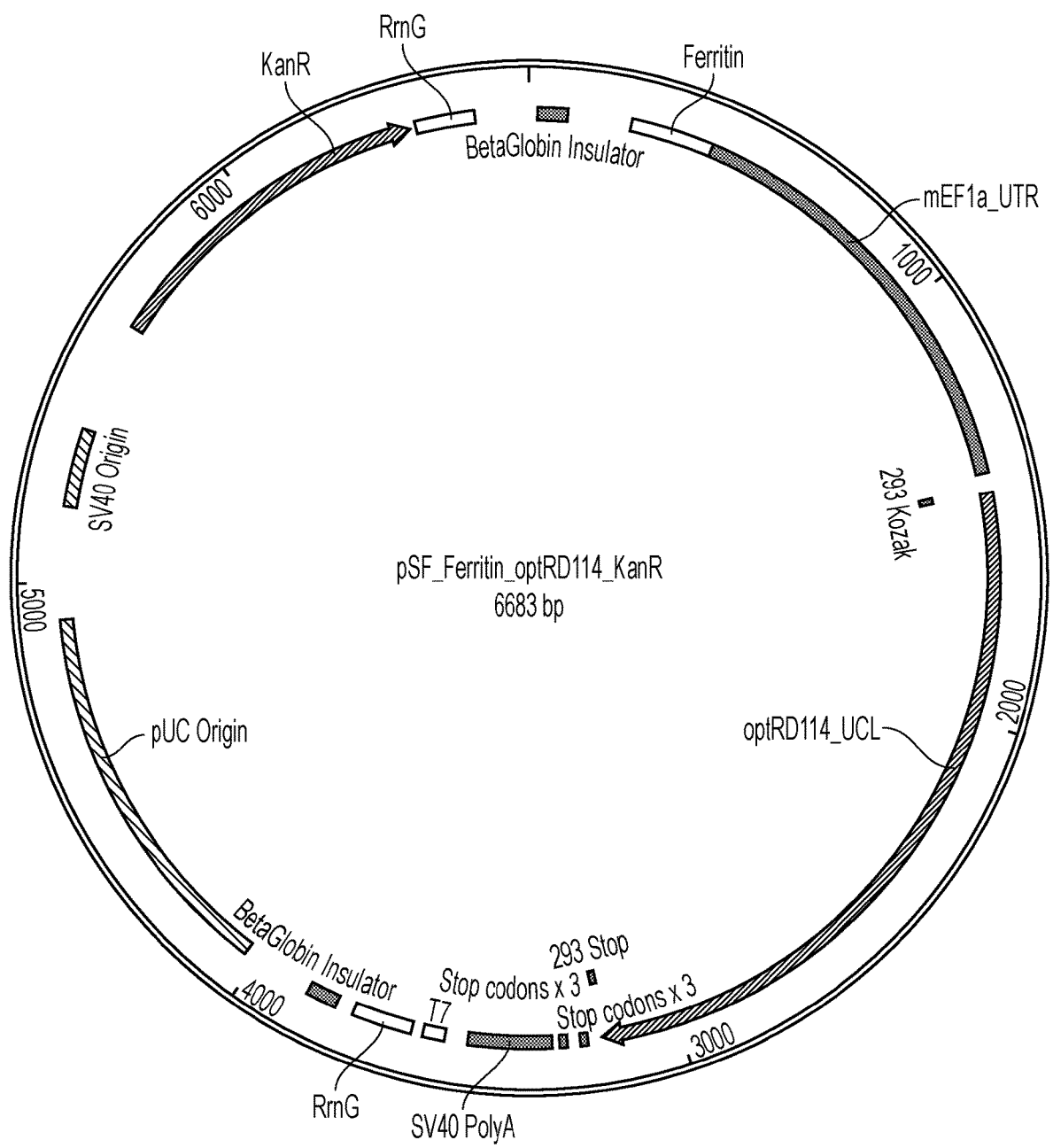
FIG. 2: Map of an envelope plasmid of the plasmid system of the present invention

An example of a polyA sequence of the helper plasmid described herein includes, but is not limited to, SV40 polyA sequence. FIG. 2 shows a map of an envelope plasmid construct of the present invention.

ENV Protein

A heterologous envelope gene may be used to pseudotype a retroviral vector to alter infectivity to the host. For example, the use of the VSV-G envelope protein provides a wide range of cell types (tropism) that a virus can infect. Despite its efficacy, VSV-G is cytotoxic, a feature that prohibits the development of stable cell lines that constitutively express this envelope. The RD114 Envelope protein is an example of a much less toxic pantropic viral envelope, also capable of infection of a variety of cell types, including stem cells and T cells.

The Env (Envelope) protein is a bipartite transmembrane protein and is cleaved by furin within the Golgi apparatus while being trafficked to the cell surface membrane. The viral Env protein determines viral tropism, or which cell types a virus can infect. The classes of viral envelopes are: i) ecotropic: narrow host range, can infect only one or a small group of species (usually mouse and rat); ii) amphotropic: broader host range, usually refers to viruses infecting only mammalian cells; iii) pantropic: broadest host range; both mammalian and non-mammalian cells can be infected. The vesicular stomatitis viral envelope (VSV-G) commonly used to package lentivirus and retrovirus is an example of a pantropic envelope.

RD114 Envelope

The Env protein in the envelope plasmid described herein may be derived from the feline endogenous retrovirus RD114 (UniProt entry: P31791), as shown in FIG. 2. This envelope confers the virions increased stability in the presence of human serum, compared with the wild-type MoMuLV envelope.

The RD114 Env provides increased particle stability and its receptor is widely expressed on hematopoietic stem cells (HSCs). Both transient transfection as well as generation of a stable cell line may be done with a RD114 envelope.

The present inventors have developed an improved envelope plasmid compared to the original envelope plasmid pLTR-RD114. It has previously been reported that codon optimisation of Env-encoding sequences leads to a non-functional Env due to impaired glycosylation of the precursor protein, so it is not expected that codon optimised Env-encoding sequences a) encode a functional protein and b) in combination with a codon-shuffled GagPol-encoding sequence leads to increased efficiency of gene expression.

The CAI of the wild type RD114 is 0.66 and this was increased to 0.78 in the codon optimised sequence described in the Examples. Both wild type and codon-optimised versions were cloned into each of the plasmid designs. The resulting 10 envelope plasmids are listed in the Examples section herein.

GALV Envelope

GALV (Gibbon ape leukemia virus) is a highly oncogenic C-type retrovirus capable of inducing myeloid leukemia in juvenile gibbons. GALV (UniProt: 070653) is antigenically most closely related to a new world monkey virus, simian sarcoma associated virus (SSAV), and less to the murine and feline C-type leukemia viruses.

As with RD114 Env protein, GALV Env proteins are able to form stable producer cell lines, making them potentially useful for small and large-scale production of pseudotyped vectors. GALV and RD114 are closely related type C mammalian retroviruses, and their entry pathways have common features. Their Env proteins contain two subunits, SU and TM, which are cleaved from a common precursor protein during transport to the cell surface. An additional feature of these Env proteins is that the C-terminal region of the cytoplasmic tail, the R peptide, is cleaved by the viral protease at, or shortly after, viral budding. R peptide cleavage is necessary to confer full activity to the Env protein, although not all of the Env proteins in a virion are cleaved. The processing of the cytoplasmic tail of Env is not unique to the mammalian type C retroviruses and has also been reported for more-distantly related retroviruses such as the Mason-Pfizer monkey virus and equine infectious anemia virus.

Described herein is an envelope plasmid comprising a codon-optimised GALV Env protein or a codon-optimised RD114 Env protein in combination with a helper plasmid comprising MLV-derived codon shuffled Gag and Pol polyproteins.

iii) Genome Plasmid

A genome plasmid (sometimes referred to as the transfer plasmid) comprises the exogenous NOI, also known as a transgene sequence. The NOI sequence is flanked by long terminal repeat (LTR) sequences, which facilitate integration of the transfer plasmid sequences into the host genome. The sequence between LTRs also contains the packaging signal of the virus and may contain a polypurine tract (PPT) and for lenti also a central polypurine tract (cPPT).

Typically, it is the sequence between and including the LTRs that is integrated into the host genome upon transfection into a cell to make a producer cell.

Figure 3:
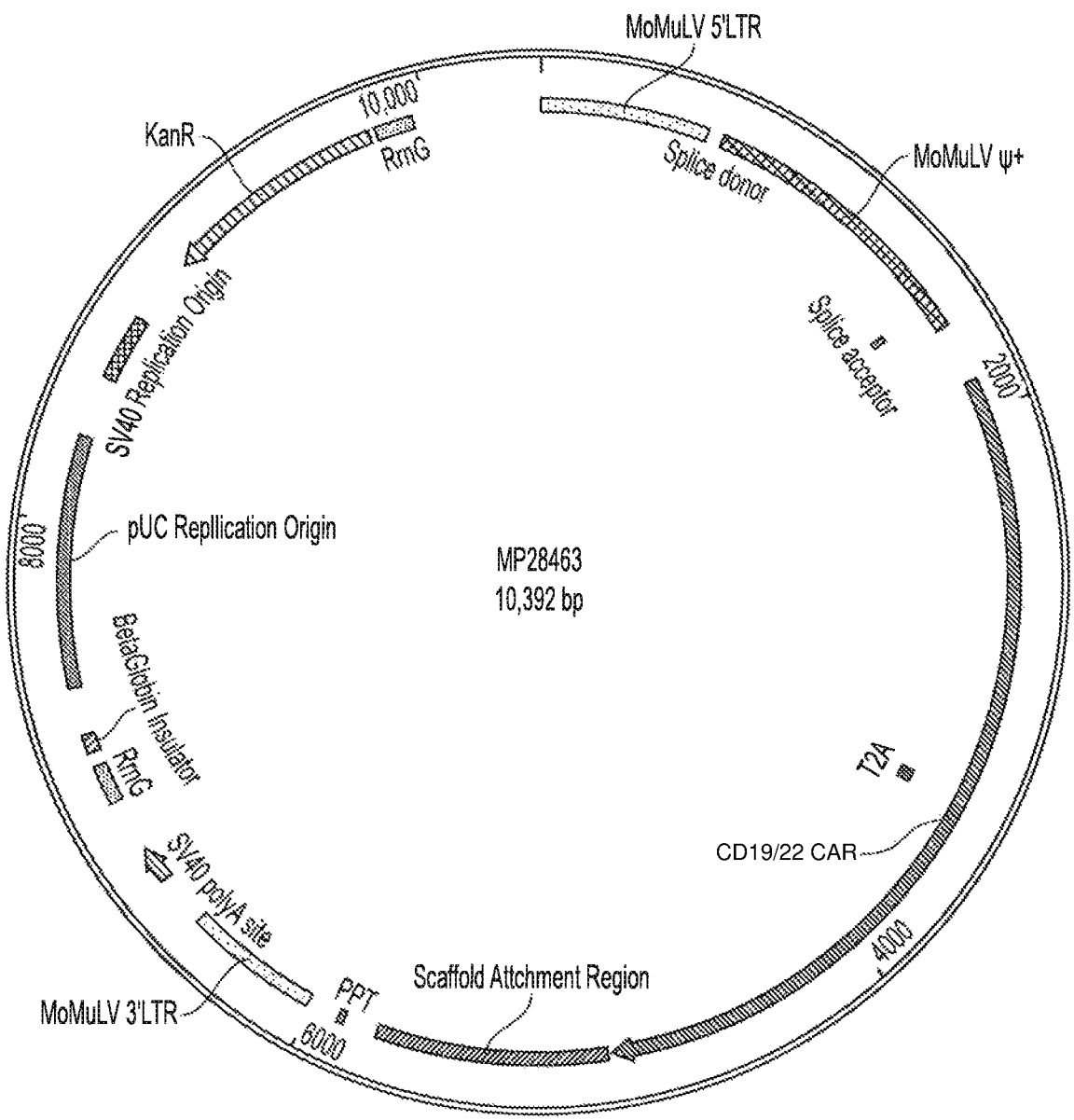
FIG. 3: Map of a genome plasmid of the plasmid system of the present invention encoding a CD19/CD22 CAR
Figure 4:
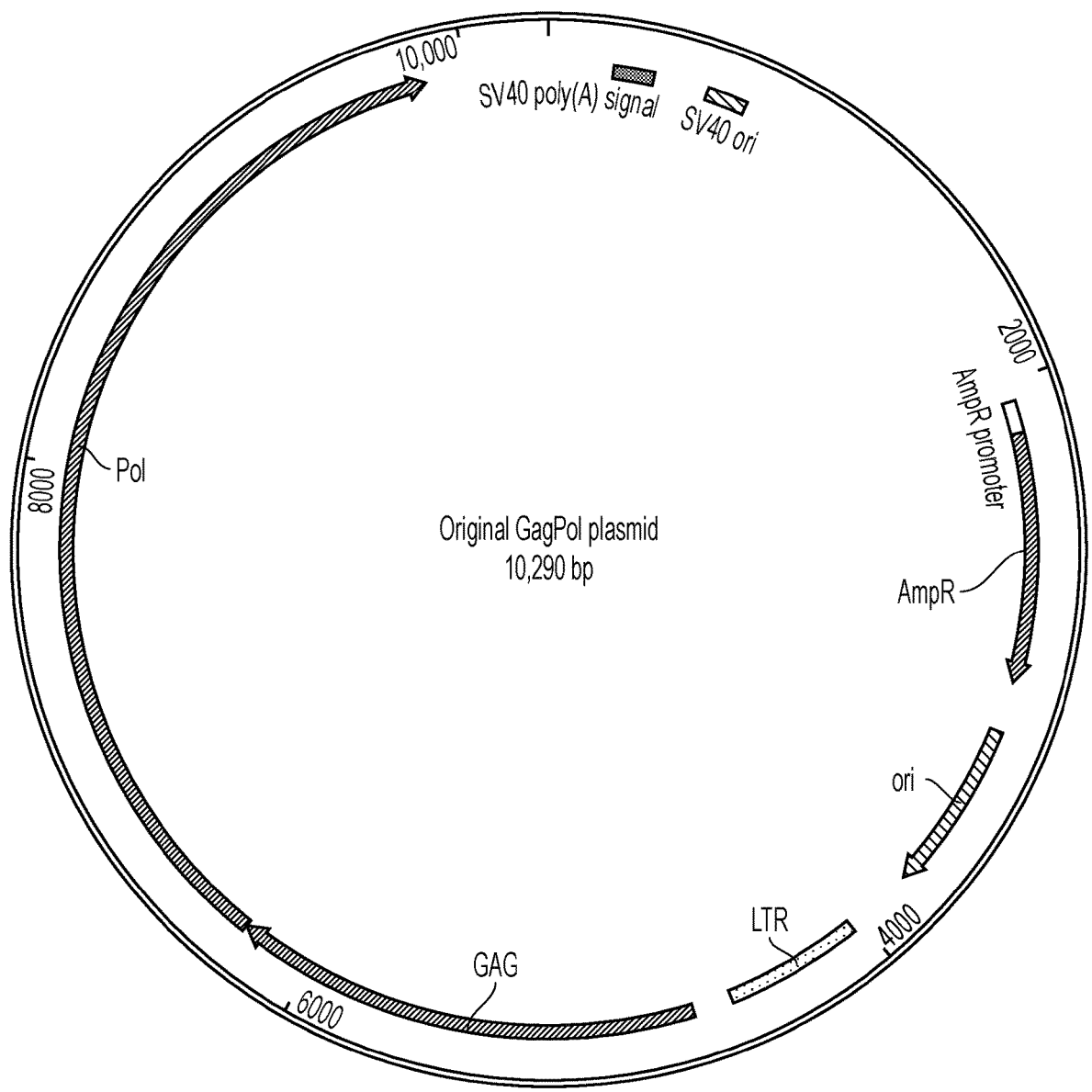
FIG. 4: Originals maps of a helper plasmid and envelope plasmid used in standard vector manufacture by transient transfection.
Figure 4:
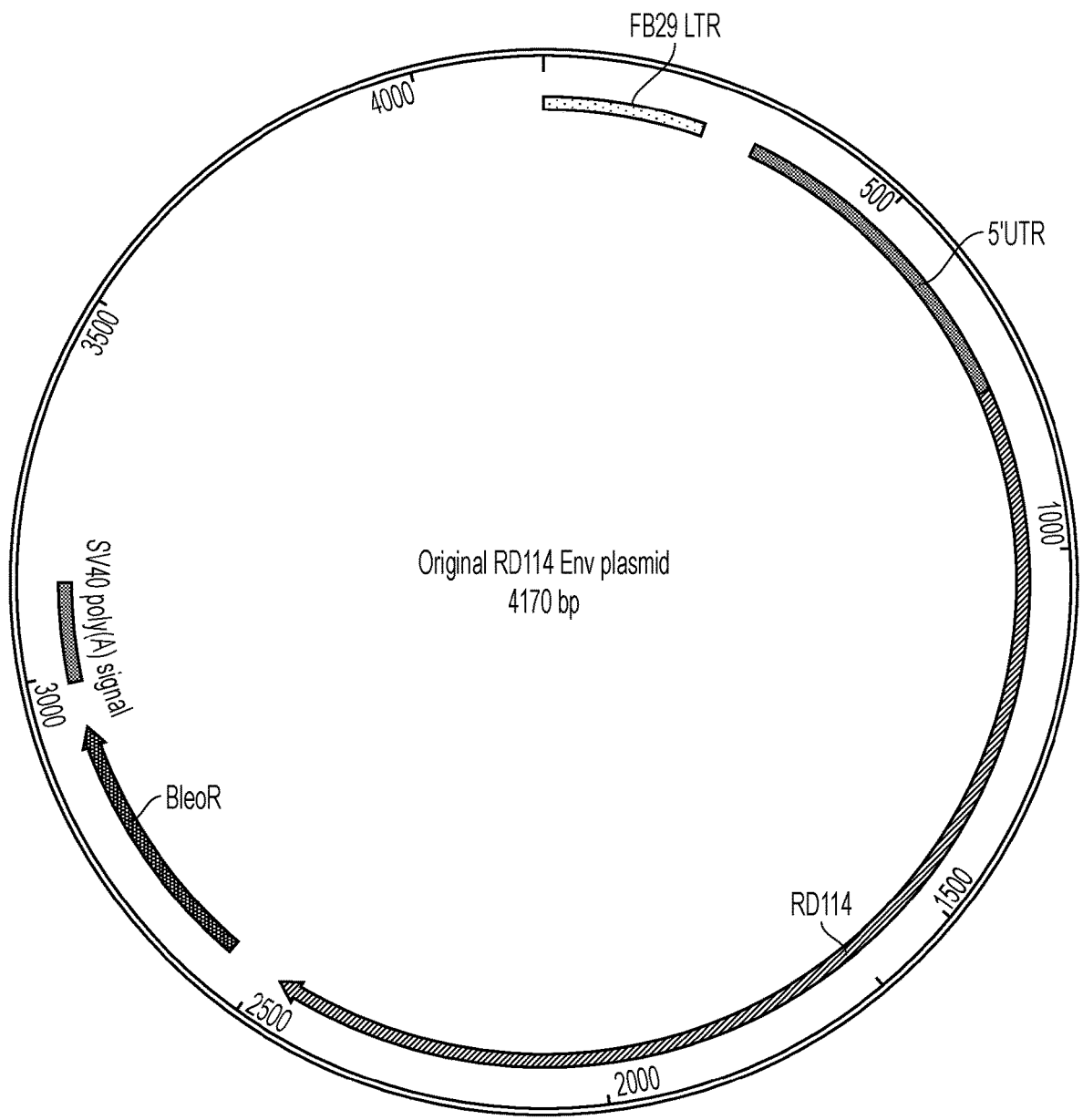

The genome plasmid (FIG. 3) described herein may derive from MoMLV. Since the expression of a transgene is driven by the MoMLV-LTR after integration, rather than an exogenous promoter, the step of selecting a promoter that differs from that of helper plasmid and envelope plasmid is relatively simple.

Examples of other elements featured in a genome plasmid described herein include but are not limited to: an intron sequence, a polyA sequence and a stop codon. As with the other two plasmids of the three plasmid system described herein, the regulatory exogenous elements of the genome plasmid may not be the same as the regulatory exogenous elements of the helper or envelope plasmids.

Since the size of the genome plasmid may be of consideration, depending on the length of the NOI, the introns present in the genome plasmid may also be removed.

Synergistic Effect of the Plasmids

The present inventors have surprisingly found that the combination of specific plasmids of the plasmid system of the present invention provides improved efficiency of the producer cell in terms of vector titre. Each plasmid of the system has been modified at the nucleotide level and/or with the presence or absence of certain regulatory elements. Notably, none of the exogenous regulatory elements between the helper plasmid and the envelope plasmid are the same.

Table 1 below shows two example preferred combinations of exogenous regulatory elements of modified helper and Envelope plasmid.

TABLE 1

| Helper (GagPol) Plasmid | Envelope (Env) Plasmid |
|---|---|
| CMV promoter/β-globin intron/Rabbit globin polyA | Ferritin promoter/ mEF1α/SV40 polyA |
| CMV promoter/Rabbit globin polyA | Ferritin promoter/ mEF1α/SV40 polyA |

Nucleotide of Interest (NOI)/Polypeptides of Interest (POI)

The viral vector of the present invention is capable of delivering a nucleotide of interest (NOI) to a target cell, such as a T cell or a natural killer (NK) cell.

The NOI may encode all or part of a T-cell receptor (TCR) or a chimeric antigen receptor (CAR) and/or a suicide gene.

The viral vector of the present invention is capable of delivering a polypeptide of interest (POI) to a target cell, such as a T cell or a natural killer (NK) cell.

The POI may be any polypeptide that is desired to be expressed in the transduced cell population. The POI may, for example be a Chimeric antigen receptor (CAR) or an engineered T cell receptor (TCR). The POI may be a polypeptide encoding for a suicide gene.

CARs, are chimeric type I trans-membrane proteins which connect an extracellular antigen-recognizing domain (binder) to an intracellular signalling domain (endodomain). The binder is typically a single-chain variable fragment (scFv) derived from a monoclonal antibody (mAb), but it can be based on other formats which comprise an antibody-like antigen binding site. A spacer domain is usually necessary to isolate the binder from the membrane and to allow it a suitable orientation. A trans-membrane domain anchors the protein in the cell membrane. A CAR may comprise or associate with an intracellular T-cell signalling domain or endodomain.

CAR-encoding nucleic acids may be transferred to cells, such a T cells, using the retroviral or lentiviral vector of the present invention. In this way, a large number of cancer-specific T cells can be generated for adoptive cell transfer. When the CAR binds the target-antigen, this results in the transmission of an activating signal to the T-cell it is expressed on. Thus the CAR directs the specificity and cytotoxicity of the T cell towards tumour cells expressing the targeted antigen.

A suicide gene encodes a polypeptide which enable the cells expressing such a polypeptide to be deleted, for example by triggering apoptosis. An example of a suicide gene is described in WO2013/153391.

Making a Retroviral Vector: Transient and Stable Transfection of a Producer or Packaging Cell In a transient transfection, the transfected material enters the cell but is not integrated into the cellular genome. This method is generally useful for shorter-term expression of genes or gene products, or small-scale protein production. In contrast, material is integrated into the cellular genome via stable transfection but this method is a longer and more complex process, mainly for large scale protein production.

Components used to generate retroviral/lentiviral vectors include a helper plasmid encoding the Gag/Pol proteins, an envelope plasmid encoding the Env protein (and, in the case of lentiviral vectors, the rev protein), and the retroviral/lentiviral vector genome, as described herein. Vector production involves transient transfection of one or more of these components into cells containing the other required components.

The packaging cells of one aspect of the invention may be any mammalian cell type capable of producing retroviral/lentiviral vector particles. The packaging cells may be 293T-cells, or variants of 293T-cells which have been adapted to grow in suspension and grow without serum.

In the case of lentiviral vector, transient transfection with a rev vector is also performed.

The invention provides a plasmid system for transfection into a cell to create a producer cell, according to the first aspect of the invention. Also described herein are also other methods of transferring exogenous material into a cell. Other methods may include transduction, transposition or site-specific integration for creating stable cell lines.

A producer cell is a cell that produces a retroviral vector by transient transfection or with a stable cell line.

A producer cell for a retroviral vector may comprise gag, pol and env genes. A producer cell for a lentiviral vector may comprises gag, pol, env and rev genes.

The producer cell may comprise gag, pol, env and optionally rev genes and a retroviral or lentiviral vector genome.

In a recombinant retroviral or lentiviral vector for use in gene therapy, the gag-pol and env protein coding regions are provided by the packaging cell. This makes the viral vector replication-defective as the virus is capable of integrating its genome into a host genome but the modified viral genome is unable to propagate itself due to a lack of structural proteins.

In the plasmid system of the invention, the gag, pol and env (and, in the case of lentiviral vectors, rev) viral coding regions are carried on separate expression plasmids that are independently transfected into a packaging cell line, so that three recombinant events are required for viral production. Packaging cells are used to propagate and isolate quantities of viral vectors i.e to prepare suitable titres of the retroviral vector for transduction of a target cell.

Cell

There is provided a cell transfected with a plasmid system of the first aspect of the present invention to create a producer cell. There is also provided a cell transfected with helper and envelope plasmid from the plasmid system of the first aspect of the invention to create a packaging cell. The cell which is to be transfected may be referred to as the parent cell. It maybe any suitable cell type such as a 293T cell or a HeLa cell.

The cell of the invention may be an ex vivo cell from a subject. The cell may be from a peripheral blood mononuclear cell (PBMC) sample. Such cells may be activated and/or expanded prior to being transduced with nucleic acid encoding the molecules providing the plasmid system according to the first aspect of the invention.

The cell may be made by: (i) isolation of a cell-containing sample from a subject or other sources listed above; and (ii) transducing or transfecting the cell with plasmid system according to the first aspect of the invention.

The cells of the present invention may be capable of producing retroviral vectors or packaging retroviral vectors for transducing cells, such as a T cells. These transduced cells, such as T cells, may be for use in the treatment and or/prevention of diseases. The disease to be treated and/or prevented may be a cancerous disease.

Nucleic Acid

The present invention relates to a nucleic acid encoding MLV-derived Gag and Pol poly-proteins. Described herein are nucleic acid sequences encoding MLV-derived Gag and Pol polyproteins, which comprise a sequence selected from: SEQ ID NO: 1 to SEQ ID NO: 3.

Additionally the present invention also relates to a second nucleic acid sequence encoding an Env protein. Described here are nucleic acid sequences encoding Env protein, which comprise a sequence selected from: SEQ ID NO: 5 to SEQ ID NO: 7 and SEQ ID NO: 9 to 11.

As used herein, the terms "polynucleotide", "nucleotide", and "nucleic acid" are intended to be synonymous with each other.

It will be understood by a skilled person that numerous different polynucleotides and nucleic acids can encode the same polypeptide as a result of the degeneracy of the genetic code. In addition, it is to be understood that skilled persons may, using routine techniques, make nucleotide substitutions that do not affect the polypeptide sequence encoded by the polynucleotides described here to reflect the codon usage of any particular host organism in which the polypeptides are to be expressed.

Nucleic acids may comprise DNA or RNA. They may be single-stranded or double-stranded. They may also be polynucleotides which include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of the use as described herein, it is to be understood that the polynucleotides may be modified by any method available in the art. Such modifications may be carried out in order to enhance the in vivo activity or life span of polynucleotides of interest.

The terms "variant", "homologue" or "derivative" in relation to a nucleotide sequence include any substitution of, variation of, modification of, replacement of, deletion of or addition of one (or more) nucleic acid from or to the sequence.

The invention will now be further described by way of Examples, which are meant to serve to assist one of ordinary skill in the art in carrying out the invention and are not intended in any way to limit the scope of the invention.

EXAMPLES

The initial round of experiments consisted of small-scale vector production and substituting one of the three plasmids with a range of new designs while using the standard plasmids for the other two functions. The best performing plasmids for each component were then taken to combination testing experiments to come to the optimal combination and relative ratio of the plasmids. Some larger scale experiments with different genomes were then conducted to assess the robustness of the plasmid system.

Example 1: Retroviral Vector Manufacture and Titration

Retroviral vectors pseudotyped with the RD114 envelope were produced by transient transfection of HEK (Human embryonic kidney) 293 T cells using Lipofectamine® 2000. HEK293T cells were seeded to be 80-90% confluent on the day of transfection. Transfection was carried out using 48 μl Lipofectamine per 10 cm dish; the amount of transfection reagent remained the same regardless of the plasmid amounts. The media were replaced 16-18 hours after transfection containing 1 mM NaBu. The vector was harvested 48 hours post-transfection, filtered through a 0.45 μm filter, and stored at −80° C.

For functional titration, HEK293T cells were transduced with serial dilutions of vector stock in the presence of 8 μg/ml polybrene. The cells were harvested four days post-transduction and stained for expression of the transgene. Transgene positive cells were scored using flow cytometry and titres calculated as transducing units/ml.

Example 2: Design of the MLV-Derived Gag and Pol Polyprotein Helper Plasmid

Five different versions of the helper plasmid were designed; each contained a strong promoter and an efficient polyadenylation site. Each of these versions was constructed using either the wild-type or a codon-shuffled version of the MLV-derived GagPol coding sequence, resulting in a total of 10 different plasmids.

Care was taken to maintain the stop codon between Gag and Pol in order to maintain the read-through mechanism that results in the majority of transcripts being Gag and minority being GagPol. Additional stop codons were also introduced downstream of the coding sequence to ensure efficient transcription termination.

Rabbit β-globin polyadenylation site was used for all of the versions as it confers high gene expression. The versions are summarised in Table 2.

The codon usage in the GagPol coding sequence was shuffled for expression in human cells. Interestingly, the Codon Adaptation Index (CAI) increased from 0.72 in the wild type to 0.77 in the shuffled sequence.

TABLE 2

10 different helper plasmids

| | Plasmid | GagPol CDS | Promoter | Intron |
|---|---|---|---|---|
| 1 | pSF_CAG_GagPol_RabpA | Wild-type | CAG (CMV enhancer/chicken β-actin promoter) | None |
| 2 | | Codon-shuffled | | |
| 3 | pSF_CMV_ GagPol _RabpA | Wild-type | CMV | None |
| 4 | | Codon-shuffled | | |
| 5 | pSF_CMV_BGIntron_ GagPol _RabpA | Wild-type | CMV promoter & Intron from Human β-globin gene | Human β-globin |
| 6 | | Codon-shuffled | | |
| 7 | pSF_POXG1_ GagPol _ RabpA | Wild-type | POXG1 | None |
| 8 | | Codon-shuffled | | |
| 9 | pSF_Prom565_ GagPol _ RabpA | Wild-type | Prom565 | None |
| 10 | | Codon-shuffled | | |

All 10 different versions of the helper plasmid were tested for small scale vector manufacture using transient transfection. The standard envelope plasmid pLTR-RD114 and genome plasmid pLTR-APRIL were kept the same throughout the experiments. The amount of envelope plasmid was kept constant, whilst two different amounts of the helper plasmid were tested: the standard amount normally used for transfection (designated as "standard") and ¼ of the standard amount (designated as "low"). This was done to account for the expression levels from the new plasmids to be higher, and as such, may lead to the generation of excessive empty vector particles. The total amount of DNA per transfection was kept the same so that transfection efficiency and the DNA:Lipofectamine ratio wouldn't be affected, such as, when a reduced amount of GagPol was used the amount of genome plasmid pLTR-APRIL was increased accordingly.

Figure 5:
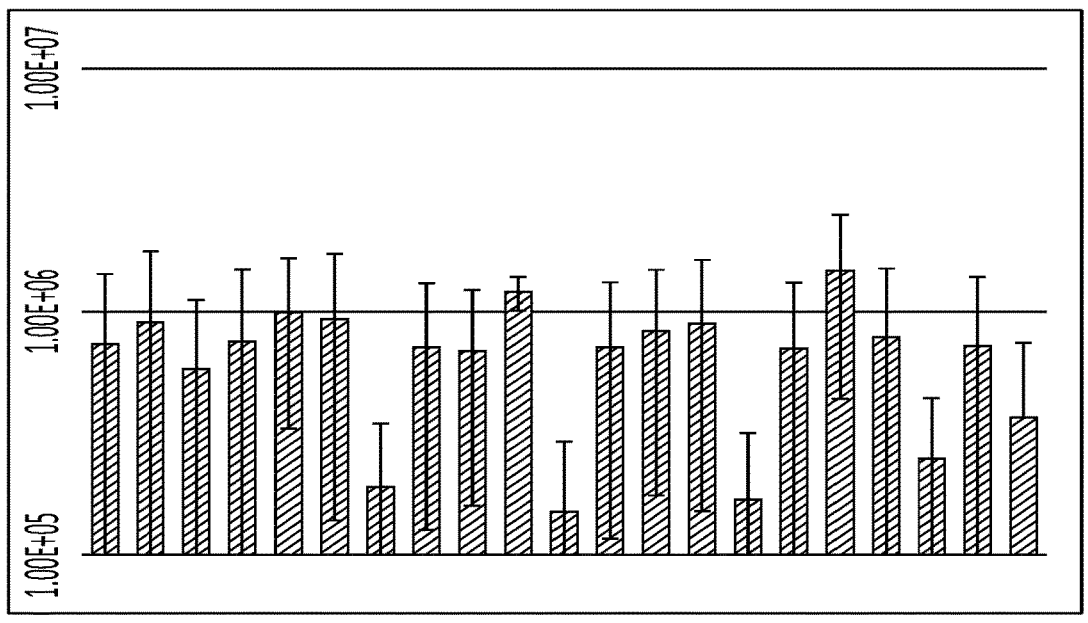
FIG. 5: Titration results of five independent vector preparations made using the different helper plasmids. All 10 helper plasmids were used either at the standard or low amount (¼ of standard). Sample 21 represents the unmodified, standard LTR-driven helper plasmid. The conditions chosen to bring forward for further optimisation experiments are highlighted.

Retroviral vectors were produced by three plasmid co-transfection in HEK293T cells over four independent experiments and were titrated by transducing HEK293T cells and assessing transgene expression by flow cytometry after four days. The results are shown in FIG. 5.

Several of the new helper plasmids increased the vector titre compared to the standard pLTR-GagPol helper plasmid by up to 10-fold. Even better, increased titres were obtained using the decreased (LOW) amount of plasmid, suggesting the feasibility of reducing the amount of helper plasmid required.

The best performing helper plasmids were brought forward for further optimisation experiments, for testing in combination with a range of new envelope plasmids. Only the the codon shuffled versions of the coding sequence were selected due to the increased safety profile (see Example 7); as the shuffled DNA sequence is different from the wild-type gene there will be no sequence homology with the extended packaging signal present in the genome plasmid which spans the beginning of Gag and the end of Pol.

Based on the data, three plasmids were chosen for further optimisation experiments:
a) pSF_CAG_shufGAGPOL (4),
b) pSF_CMV_shufGAGPOL (8),
c) pSF_p565Prom_shufGAGPOL (20).

Example 3: Design of RD114 Envelope Plasmid

Five different versions of the Envelope plasmid comprising the RD114 envelope protein were designed; each also comprising a strong promoter and a highly efficient SV40 polyadenylation site. All but one of the designs also contain an intron in the 5'UTR.

The CAI of the wild type RD114 is 0.66 and this increased to between 0.75 and 0.78 in the codon optimised sequence. Both wild type and codon-optimised versions were cloned into each of the plasmid designs. The resulting 10 envelope plasmids are summarised in Table 3 below.

TABLE 3

10 different envelope plasmids

| | Plasmid | Env CDS | Promoter | Intron |
|---|---|---|---|---|
| 1 | pSF_CMV_RD114_SV40pA | Wild-type | CMV | None |
| 2 | | Codon-optimised | | |
| 3 | pSF_CMV_BGIntron_ RD114_SV40pA | Wild-type | CMV | Human β-globin |
| 4 | | Codon-optimised | | |
| 5 | pSF_CMV_EnvNatUTR_ RD114_SV40pA | Wild-type | CMV | RD114 intron |
| 6 | | Codon-optimised | | |
| 7 | pSF_POXG3_RD114_SV40pA | Wild-type | POXG3 | None |
| 8 | | Codon-optimised | | |
| 9 | pSF_Ferritin _mEf1UTR_ RD114_SV40pA | Wild-type | Ferritin | Murine elongation factor 1α intron |
| 10 | | Codon-optimised | | |

Codon optimisation has previously been reported to lead to non-functional RD114 due to impaired glycosylation of the precursor protein. However, and surprisingly, this finding was not replicated and the present inventors were able to generate a functional, codon optimised RD114 coding sequence that outperformed its non-optimised standard counterpart.

The ten different versions of the envelope plasmid were tested by small scale vector production using transient transfection. The standard helper plasmid pLTR-GagPol and genome plasmid pLTR-APRIL were kept the same throughout the experiments. Whilst the amount of packaging plasmid was kept constant, two different amounts of the envelope plasmid were tested: the standard amount normally used for transfection (designated as "standard") and ¼ of the standard amount (designated as "low"). This was done to avoid potential reduction in vector titre resulting from excessive RD114 protein presence in producer cells due more efficient Env gene expression. As before with helper, the total amount of DNA per transfection was kept the same so that when a reduced amount of envelope plasmid was used the amount of genome plasmid could be increased accordingly.

Figure 6:
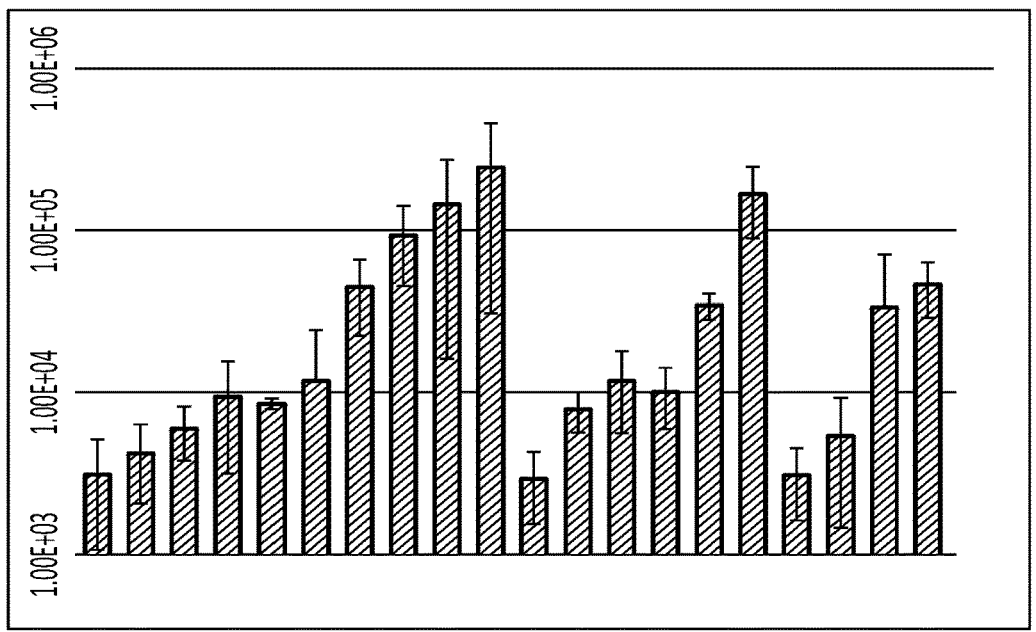
FIG. 6: Titration results of five independent vector preparations made using different envelope plasmids, all comprising the RD114 Envelope protein. All 10 envelope plasmids were used either at a standard or low amount (¼ of standard). Sample 21 represents the unmodified, standard LTR-driven RD114 envelope plasmid used at the standard amount. The plasmid chosen to bring forward for further optimisation experiments is highlighted.
Figure 7:
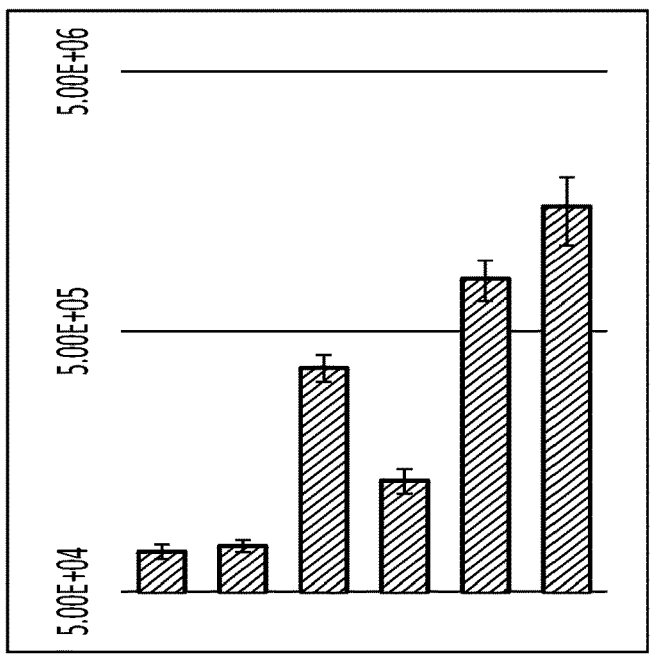
FIG. 7: Titration results of two independent vector preparations made using the different helper plasmids, comprising the Galv Envelope protein. All 6 helper plasmids were used either at the standard, low amount (¼ of standard) or high amount (2× of standard). The helper plasmid with the highest titre is highlighted.

The vectors were produced over three independent experiments and titrated by transducing HEK293T cells and assessing transgene expression by flow cytometry after 4 days. The results are shown below in FIG. 6.

The best performing plasmid was taken forward for further optimisation experiments, to be tested in combination with a range of new helper plasmids. There is no sequence homology between the envelope plasmids and the other plasmids regardless of whether the wild-type or the codon optimised version of the RD114 sequence is used, and therefore the main consideration was the efficiency of gene expression and hence the titre achieved using the minimum amount of plasmid. The plasmid that outperformed others was chosen for further optimisation experiments: pSF_Ferritin_mEF1α_optRD114 (16).

Example 4: Helper Plasmid and Envelope Plasmid Design Providing Synergistic Effect Following the selection of the most promising helper and envelope plasmids by single plasmid substitution experiments described in Examples 1 and 2, a set of experiments was designed to assess the synergistic effects of combining different helper and envelope plasmids in different ratios. As decreasing the amount of plasmid required is desirable and $\frac{1}{4}^{th}$ of the standard amount produced equivalent titre vector in the first set of experiments, a further plasmid amount of $\frac{1}{16}^{th}$ was introduced. The two plasmids were therefore used in three amounts, designated "standard" (S), "low" (L) (¼ of standard) or "minimal" (M) ($\frac{1}{16}$ of standard).

As changing the helper plasmid resulted in a more significant increase in the vector titre compared to the envelope plasmid, the strong CMV promoter was prioritised for use in the helper plasmid. The same promoter cannot be used in both plasmids due to the need to avoid sequence homology during transfection, and as three of the best-performing helper plasmids contained the CMV promoter, the ferritin promoter presented an attractive option for inclusion in the envelope plasmid. Thus, the number of allowed helper/envelope plasmid combinations to be tested were:

1) pSF_CMV_shufGAGPOL/pSF_Ferritin_mEF1α_optRD114-UCL
2) pSF_CAG_shufGAGPOL/pSF_Ferritin_mEF1α_optRD114-UCL
3) pSF_p565Prom_ShufGAGPOL/pSF_CMV_BGIntron_wtRD114 (or optRD114)

The plasmid combinations were tested by transient transfection using two different genome plasmids, pGEN1 and pGEN2, to ensure that any titre differences would be applicable to all vector types. The first small scale transient transfection was done using 10 cm plates and the pGEN1 genome plasmid in two independent experiments. The vectors were titrated by transducing HEK293T cells and assessing transgene expression by flow cytometry after four days. The results are shown in FIG. 8.

Figure 9:
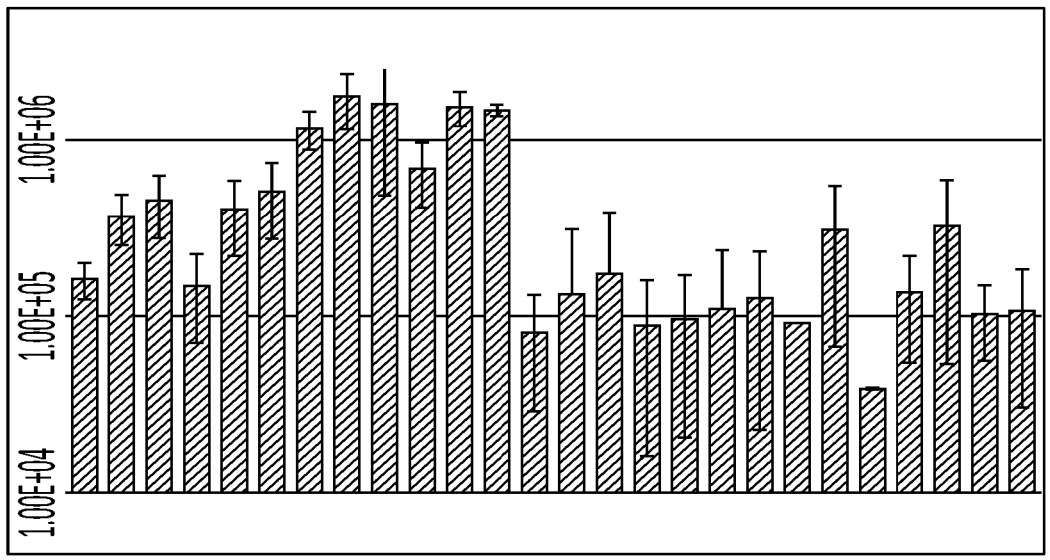
FIG. 9: Titration results of independent vector preparations using the different helper and Envelope plasmids at different ratios. The plasmids are used in 3 amounts, designated "standard" (S), "low" (L) (¼ of standard) or "minimal" (M) (¹⁄₁₆ of standard. The first letter refers to the amount of helper plasmid used and the second letter to the amount of Envelope plasmid used. The total amount of DNA per transfection was kept constant by the addition of genome vector plasmid. pGEN2, genome plasmid 2. Samples 25 and 26 are controls made using the original unmodified plasmids.

The testing of different plasmid combinations and ratios was repeated by larger scale vector production in two independent experiments using transient transfection in T175 flasks and the pGEN2 genome plasmid. The vectors were titrated by transducing HEK293T cells and assessing CAR expression by flow cytometry after four days. The results are shown in FIG. 9.

Example 5: Larger Scale Vector Manufacture with Multiple Plasmid Combinations and Rations Based on the titrations, the plasmid combination that most consistently produced the highest titre of vector with the lowest plasmid input was pSF_CMV_shufGAGPOL/pSF_Ferritin_mEF1α_optRD114. Further vector preparations were done in T175 flasks using the minimal amount ($\frac{1}{16}^{th}$ of standard) of each plasmid and using three different genome plasmids. As a control, vectors were produced alongside the original helper and envelope plasmids in the standard amounts. The titres obtained with the shuffled/optimised versus original plasmids using different genome plasmids (GEN1 and GEN2) are summarised below in Table 4 below.

TABLE 4

Comparison of vector titres achieved with original versus improved plasmids

| GEN1 vector titres | Prep3 | Prep2 | Prep4 | Prep5 | Average |
|---|---|---|---|---|---|
| Shuffled GagPol in helper plasmid & optimised Env in Envelope plasmids | 1.36E+06 | 1.85E+06 | 2.96E+06 | 3.49E+06 | 2.41E+06 |
| Original GagPol & Env plasmids | 6.29E+05 | 4.28E+05 | 4.18E+05 | 1.06E+06 | 6.34E+05 |
| GEN2 vector titres | Prep1 | Prep2 | Prep4 | | Average |
| Shuffled GagPol in helper plasmid & optimised Env in Envelope plasmids | 1.55E+06 | 1.39E+06 | 2.32E+06 | | 1.75E+06 |

TABLE 4-continued

Comparison of vector titres achieved with
original versus improved plasmids

| Original GagPol & Env plasmids | 1.36E+05 | 6.94E+04 | 4.18E+05 | 2.08E+05 |

Comparison of vector titres achieved with original versus the shuffled helper and optimised envelope plasmids. Both genome plasmids GEN1 and GEN2 showed increased average titre by about 1 log with the modified plasmids (shuffled and optimised) compared to the original plasmids.

The experiment showed that high retroviral titres can be obtained with the shuffled GagPol and optimised Env sequences in the helper and envelope plasmids respectively, with transient transfection, even when the amount of the packaging plasmids was reduced. However, this resulted in an increase in the amount of genome plasmid required in order to maintain the same total amount of DNA used per transfection.

A lower genome plasmid requirement would benefit the production process by reducing the plasmid contamination at the end and reducing the cost of production. Therefore, further experiments were carried out to assess the effect of genome plasmid amount reduction on vector titre.

The experiment showed that high retroviral titres can be obtained with the shuffled GagPol and optimised Env sequences in the helper and envelope plasmids respectively, with transient transfection, even when the amount of the packaging plasmids was reduced.

A lower genome plasmid requirement would benefit the production process by reducing the plasmid contamination at the end and reducing the cost of production. Therefore, further experiments were carried out to assess the effect of genome plasmid amount reduction on vector titre.

Figure 10:
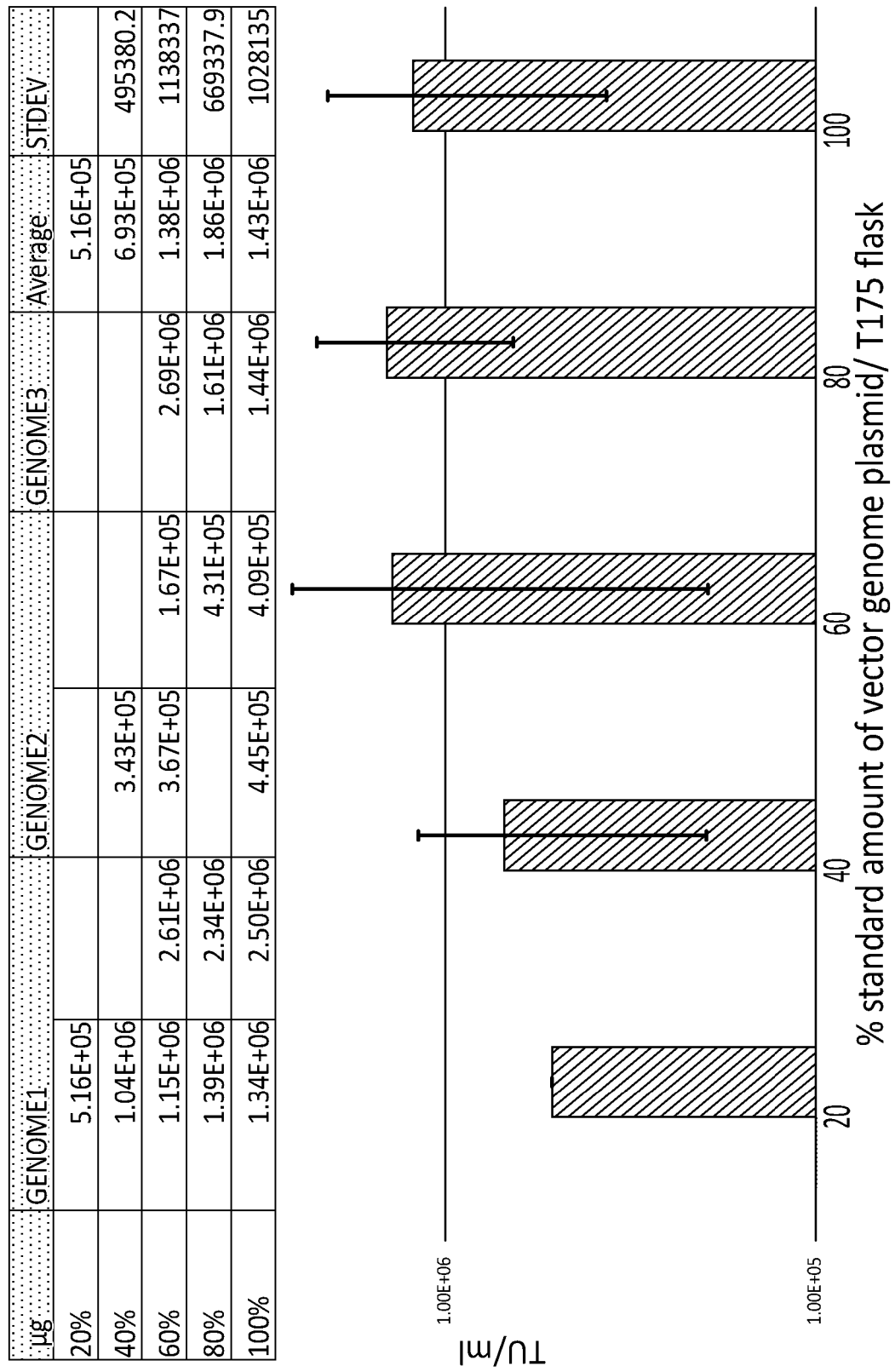
FIG. 10: Titration results of independent vector preparations in T175 flasks using the optimised helper and envelope plasmids and ratio, and with different genome plasmids at different amounts ranging from 20-100% of the standard amount.

The standard genome plasmid amount to complement the low amounts of the optimised packaging plasmids was designated as 100% per T175 flask, and we decided to test a range of genome plasmid amounts from 20-80%. Vectors were produced in independent experiments using GEN1, GEN2 and GEN3 genome plasmids. The vectors were produced in two independent experiments and titrated by transducing HEK293T cells and assessing transgene expression by flow cytometry after four days. The results are summarised in FIG. 10.

The results show that the amount of genome plasmid per flask can be reduced from 100% to 60% without a marked drop in titre. The trend is consistent when using different CAR genomes and can therefore be applied for use in vector production.

The plasmid system described herein utilises plasmid combinations and amounts with the codon-shuffled Gag-pol packaging plasmid pSF_CMV_shufGAGPOL_RabpA at $\frac{1}{16}^{th}$ of the standard amount, codon-optimised Env plasmid pSF_Ferritin_mEF1α_optRD114 at $\frac{1}{16}^{th}$ of the standard amount, and the vector genome plasmid at 60% of the standard amount.

Example 6: Large Scale Vector Production, Titre and Safety Data

The optimised plasmids were used for large scale vector production under Good Manufacturing Practice (GMP) conditions. The titres achieved were higher than those with the original plasmids, as shown in Table 6.

TABLE 5

Comparison of GMP grade vector titres

|  | Original GagPol & Env plasmids | Optimised GagPol & Env plasmids |
|---|---|---|
| GEN1 vector titres | 7.4E+05 | 3.28E+06 |

Example 7: Testing for Presence of Replication Competent Retrovirus (RCR)

Two assays were carried out to detect not only true RCR, but also potential replication-deficient but RT (reverse transcriptase)-positive particle producing virus or virus-like particle, and hence can also detect replication-deficient recombination events.

The first was a cell-based assay (PG4 S+/L− end point co-culture), which quantifies the number of replication competent virions by counting the distinct foci formed by the cytopathic effects of the RCR on the PG4 cells. PG4 cells can be used to detect and assay retroviruses and are currently recommended for the detection of replication competent retroviruses in gene therapy products The second assay was a molecular assay, qFPERT (quantitative fluorescent product enhanced reverse transcriptase), which quantifies the level of reverse transcriptase (RT) activity in the supernatant of transduced and serially passaged detector cells.

The GMP GEN1 vector batch produced using the original helper plasmids produced a negative signal for the PG4 co-culture assay but a positive signal for the QFPERT assay, albeit at 3-4 logs less RT activity than the positive control. The results of the QFPERT assays (original and re-test assay for the same vector batch sample) are shown in Table 6.

TABLE 6

Results of QFPERT assay for GEN1 vector using original plasmids

| Sample | PP5 Average CT value Assay 1 | PP5 Average CT value Assay 2 | PP6 Average CT value Assay 2 | Result |
|---|---|---|---|---|
| Gen1_Original Test article 1 | 29.82 | 26.44 | 27.75 | + |
| Gen1_Original Test article 2 | 30.9 | 26.52 | 28.85 | + |
| Negative control A | 38.66 | 37.43 | 36.48 | − |
| Negative control B | 38.15 | 35.74 | 36.12 | − |
| Cultured positive control A | 16.26 | 14.18 | 14.91 | + |
| Cultured positive control B | 19.77 | 14.79 | 16.14 | + |
| Cultured spiked Test article | 18.24 | 17.74 | 16.19 | + |
| 10E-2 units RT +ve control enzyme | 14.04 | 14.26 | | + |
| 10E-3 units RT +ve control enzyme | 17.43 | 17.74 | | + |
| 10E-4 units RT +ve control enzyme | 20.85 | 22.13 | | + |
| 10E-5 units RT +ve control enzyme | 25.79 | 25.13 | | + |
| 10E-6 units RT +ve control enzyme | 27.87 | 28.26 | | + |

TABLE 6-continued

Results of QFPERT assay for GEN1 vector using original plasmids

| Sample | PP5 Average CT value Assay 1 | PP5 Average CT value Assay 2 | PP6 Average CT value Assay 2 | Result |
|---|---|---|---|---|
| 10E-7 units RT +ve control enzyme | 31.94 | 32.61 | | + |
| NTC | 38.97 | UD | | − |
| DMEM | 37.39 | 35.37 | | − |
| MLV recovery control 10 IU | 27.84 | 21.55 | | − |

Test articles 1 and 2 are derived from duplicate cultures, PP5 and PP6 refer to the passage point at which supernatant was harvested. The positive control is derived from a culture transduced with 100 IU of positive control virus.

Results of the QFPERT assay for GEN1 vector was then manufactured using the new optimised plasmids (Table 7). Test articles 1-9 are derived from replicate cultures. The four test article repeats that initially produced a low positive signal are shown in italics. The same samples generated did not generate positive signal in two repeat assays.

These data show that the risk of recombination events between plasmids in the three-plasmid system is reduced in the GEN1-optimised plasmid system described herein, versus the GEN1-original plasmid system.

TABLE 7

Results of QFPERT assay for GEN1 vector using new optimised plasmids

| Sample | PP5 Average CT value Assay 1 | PP5 Average CT value Assay 2 | PP6 Average CT value Assay 2 | Result |
|---|---|---|---|---|
| Gen1_Opt Test article 1 | 35.68 | − | − | − |
| Gen1_Opt Test article 2 | 32.97 | − | − | − |
| Gen1_Opt Test article 3 | *28.90* | 35.76 | 36.81 | − |
| Gen1_Opt Test article 4 | *31.20* | 37.85 | UD | − |
| Gen1_Opt Test article 5 | *30.83* | 35.23 | 39.93 | − |
| Gen1_Opt Test article 6 | 36.96 | − | − | − |
| Gen1_Opt Test article 7 | *30.70* | 36.00 | 35.83 | − |
| Gen1_Opt Test article 8 | 36.10 | − | − | − |
| Gen1_Opt Test article 9 | 38.14 | − | − | − |
| Negative control A | 38.08 | UD | UD | − |
| Negative control B | 36.91 | UD | UD | − |
| Cultured spiked Test article | 15.49 | 21.16 | 23.89 | + |
| 10E-2 units RT +ve control enzyme | 14.8 | 15.44 | | + |
| 10E-3 units RT +ve control enzyme | 18.3 | 17.95 | | + |
| 10E-4 units RT +ve control enzyme | 21.8 | 22.83 | | + |
| 10E-5 units RT +ve control enzyme | 25.0 | 24.97 | | + |
| 10E-6 units RT +ve control enzyme | 28.9 | 28.24 | | + |
| 10E-7 units RT +ve control enzyme | 32.2 | 32.38 | | + |
| NTC | 36.09 | 37.9 | | − |
| DMEM | 36.42 | UD | | − |
| MLV recovery control 10 IU | 24.3 | 30.82 | | + |

Methods

The plasmids were produced over three independent experiments and titrated by transducing HEK293T cells and assessing transgene expression by flow cytometry after 4 days.

The helper and envelope plasmids were synthesised using the pSF molecular cloning plasmid vector. The various genomic component sequences were retrieved from public databases, synthesised, and cloned into the plasmids.

The helper plasmid pSF_CMV_shufGagPol_RabpA comprised the CMV promoter, the codon shuffled Gag and Pol coding sequences, and the rabbit globin polyadenylation site.

The Envelope plasmid pSF_Ferritin_mEF1α_optRD114_SV40pA comprised the promoter from the human ferritin gene (GenBank AP003733.5, nt 18029 . . . 17850), the murine EF1α 5'UTR (GenBank AC158987.3, nt 121232 . . . 120236), the codon optimised RD114 coding sequence (strain UCL) and the Simian Polyoma Virus 40 polyadenylation site.

FIGS. 1 and 2 show a Schematic representation of the shuffled Gagpol plasmid pSF_CMV_shufGagPol_RabpA and the optimised Env plasmid pSF_Ferritin_mEF1α_optRD114_SV40pA. As demonstrated in Example 3, this combination of plasmids provided a synergistic effect.

A list of the nucleotide and amino acid sequences described herein is provided:

(Gag and Pol polyproteins codon-shuffled variant)
SEQ ID NO: 1
ATGGGCCAAACCGTGACCACCCCGCTGTCGCTGACTCTGGGGCATTGGAAGGATG

TGGAACGCATCGCCCACAACCAGAGCGTGGACGTGAAGAAGCGCCGCTGGGTGA

CCTTCTGCTCCGCAGAATGGCCTACCTTTAACGTGGGGTGGCCTCGGGACGGCAC

CTTCAATCGGGACCTGATCACCCAGGTGAAAATCAAGGTGTTCAGCCCGGGTCCG

CACGGCCATCCAGATCAAGTCCCGTACATCGTGACTTGGGAAGCCCTGGCGTTCG

ACCCCCCACCGTGGGTCAAACCATTCGTCCACCCGAAGCCACCGCCACCCCTGCC

GCCGTCGGCGCCCTCACTGCCGCTGGAACCTCCGAGATCGACTCCTCCGAGATCA

TCGCTCTACCCGGCGCTCACTCCGAGCCTGGGCGCAAAGCCAAAGCCGCAAGTGC

TGTCCGATTCGGGAGGACCTCTCATCGACCTGCTCACCGAGGACCCTCCACCCTA

-continued

```
CAGAGATCCGCGCCCTCCCCCGAGCGACAGGGACGGGAACGGCGGGGAGGCCA
CCCCGGCAGGAGAAGCCCCGGACCCAAGCCCTATGGCGTCAAGACTCAGAGGCA
GAAGAGAACCTCCGGTGGCAGACTCGACTACTTCGCAGGCATTCCCACTGCGCGC
CGGGGGAAATGGCCAGCTGCAGTACTGGCCGTTCAGCTCATCGGACCTCTACAAT
TGGAAGAACAACAATCCCTCGTTCTCGGAGGACCCTGGTAAACTAACCGCTTTGAT
CGAATCGGTCCTGATTACCCACCAGCCGACCTGGGACGACTGCCAGCAGCTCCTG
GGCACTCTGCTGACCGGAGAGGAAAAACAAAGAGTGCTGCTGGAAGCACGGAAGG
CAGTGCGCGGGATGATGGCAGGCCGACCCAGCTCCCGAACGAGGTGGACGCTG
CCTTCCCACTGGAACGCCCAGATTGGGACTACACCACCCAAGCTGGAAGAAACCA
CCTGGTCCATTACCGCCAACTGCTGCTGGCAGGACTCCAAAACGCAGGACGGTCC
CCTACTAACCTGGCCAAGGTGAAAGGGATTACTCAAGGCCCGAACGAGTCGCCGA
GCGCGTTCCTAGAGCGCCTAAAAGAGGCCTACCGGCGCTACACCCCATATGACCC
AGAGGACCCAGGACAGGAAACCAATGTGAGCATGTCATTCATCTGGCAGTCAGCC
CCCGACATCGGACGCAAGCTGGAACGCCTGGAAGACCTGAAGAATAAAACGCTCG
GCGATCTGGTGCGGGAAGCAGAGAAGATTTTCAATAAACGGGAAACCCCGGAAGA
GCGGGAGGAACGCATCCGGCGCGAGACCGAAGAAAAGGAGGAACGCAGACGCAC
CGAGGATGAACAGAAGGAGAAGGAGAGAGACCGCCGCCGGCACCGCGAAATGTC
GAAACTGCTGGCCACGGTGGTCAGCGGTCAGAAGCAGGATCGCCAAGGAGGCGA
GCGCAGAAGATCGCAACTGGATCGCGACCAGTGCGCCTACTGCAAGGAGAAGGG
GCACTGGGCGAAAGATTGTCCCAAGAAACCACGAGGACCTCGGGGACCAAGACCC
CAGACCTCCCTCCTGACCCTAGATGACTAGGGAGGTCAGGGTCAGGAGCCCCCCC
CTGAACCCAGGATAACCCTCAAAGTCGGGGGGCAACCCGTCACCTTCCTGGTGGA
CACCGGCGCGCAGCACAGCGTGCTGACCCAAAACCCGGGACCTCTGTCAGACAAG
TCCGCCTGGGTGCAGGGCGCAACTGGAGGGAAGCGGTATCGGTGGACCACTGAT
CGCAAAGTGCACCTGGCAACGGGAAAAGTGACCCATTCATTTCTGCACGTGCCGG
ACTGCCCGTACCCGCTTCTGGGACGCGACCTCCTGACTAAGCTCAAGGCACAGAT
CCACTTCGAGGGATCAGGAGCGCAGGTCATGGGACCTATGGGACAACCATTGCAG
GTCCTGACCTTGAACATCGAAGACGAGTACAGGCTGCACGAGACTAGCAAGGAAC
CTGACGTGTCGCTGGGGAGCACCTGGCTGTCGGACTTTCCCCAAGCTGGGCAGA
GACCGGAGGAATGGGGCTCGCGGTCAGACAGGCACCACTCATCATCCCACTCAAG
GCCACCTCCACCCCGGTCTCAATTAAGCAATACCCGATGTCGCAGGAAGCCCGCC
TCGGAATCAAGCCGCATATTCAACGCCTCCTGGACCAAGGGATTCTGGTGCCGTG
CCAGTCGCCGTGGAACACCCCACTATTGCCGGTCAAGAAGCCTGGAACTAACGATT
ACAGGCCGGTGCAGGACCTGCGGGAAGTGAACAAACGGGTGGAGGACATCCACC
CGACCGTGCCGAATCCGTACAACCTTCTGTCCGGACTCCCTCCCTCACATCAGTGG
TACACTGTGCTCGACCTTAAGGACGCGTTCTTCTGCCTGCGCCTGCATCCGACGTC
ACAGCCGTTGTTCGCTTTCGAGTGGCGCGATCCCGAAATGGGTATCTCGGGCCAA
CTGACTTGGACTCGGCTGCCACAAGGATTCAAGAACTCGCCAACTCTGTTTGATGA
AGCTCTACACCGCGACCTGGCCGACTTCAGAATCCAACACCCGGACCTGATCCTG
CTTCAATACGTGGATGACCTGCTGCTCGCCGCGACTTCCGAGCTGGACTGTCAGC
AGGGCACTAGAGCACTGCTACAGACCTTGGGTAATCTGGGATACAGAGCAAGCGC
```

-continued

```
CAAGAAAGCTCAGATTTGCCAAAAGCAAGTGAAGTACCTGGGCTACCTTCTCAAAG

AAGGCCAGAGATGGCTGACCGAAGCCAGAAAGGAGACCGTGATGGGACAACCGA

CCCCTAAAACCCCTCGGCAGCTGCGCGAGTTCCTGGGAACCGCAGGCTTCTGCCG

CCTGTGGATTCCCGGATTCGCAGAGATGGCCGCCCCGCTATACCCTCTGACCAAG

ACCGGAACCCTGTTTAATTGGGGACCTGACCAGCAGAAGGCGTACCAAGAGATCA

AGCAAGCCCTGCTGACCGCCCCTGCCCTCGGACTGCCGGACCTGACTAAGCCCTT

TGAGCTGTTCGTGGACGAGAAGCAAGGATACGCAAAGGGCGTCCTGACTCAGAAG

CTGGGACCGTGGAGAAGACCGGTCGCGTACCTGTCCAAGAAGCTGGACCCGGTG

GCCGCTGGATGGCCACCGTGCCTGCGGATGGTGGCTGCCATTGCTGTGCTCACCA

AGGACGCAGGCAAGCTGACTATGGGACAGCCACTGGTGATCCTCGCACCGCACGC

CGTGGAGGCTCTGGTGAAACAGCCTCCTGACCGGTGGCTGTCCAATGCGCGCATG

ACTCATTACCAGGCCCTGCTCCTAGACACCGATCGGGTGCAGTTCGGACCAGTGG

TGGCACTGAACCCAGCAACTCTGCTGCCGCTGCCGGAAGAGGGGTTGCAGCACGA

CTGCCTGGACATCCTCGCAGAAGCTCACGGAACGCGGTCCGACCTTACCGACCAA

CCACTGCCCGATGCTGATCACACTTGGTACACTGATGGGTCATCATTCCTGCAAGA

AGGCCAGCGCAAAGCAGGGGCTGCAGTGACTACCGAAACTGAAGTCATTTGGGCT

CGGGCACTGCCGGCGGGGACGTCGGCACAGCGGGCGGAACTCATCGCACTCACC

CAGGCGCTGAAGATGGCCGAGGGCAAAAAGCTGAACGTGTACACCGACTCAAGAT

ACGCGTTCGCAACTGCACATATCCACGGGGAGATTTACAGACGGCGCGGTCTGCT

GACTTCGGAGGGCAAGGAAATCAAAAACAAGGACGAGATCCTGGCGCTCCTGAAA

GCCCTGTTCCTGCCAAAGCGGCTGTCAATCATCCACTGCCCTGGCCATCAGAAGG

GTAACTCCGCTGAAGCCAGGGGAAACCGCATGGCCGATCAAGCCGCGCGCGAGG

TCGCTACCAGAGAGACCCCCGGAACTTCGACGCTGCTTATCGAGAACTCCACGCC

ATACACCCACGAGCACTTTCACTACACTGTCACCGACACTAAGGATCTAACTAAGCT

GGGTGCCACTTATGATAGCGCAAAGAAGTACTGGGTGTACCAGGGGAAGCCTGTG

ATGCCCGATCAGTTCACCTTCGAGCTGCTGGATTTCCTGCATCAACTGACGCACCT

GAGCTTCTCAAAGACCAAGGCTCTGCTGGAACGCAGCCCTTCGCCGTACTATATGT

TGAATAGGGATCGCACCCTGAAGAATATCACCGAAACCTGCAAGGCCTGCGCCCA

GGTGAATGCTTCCAAGTCCGCCGTGAAGCAGGGCACCCGCGTCCGCGGACACCG

CCCTGGAACTCACTGGGAGATCGACTTCACTGAGGTGAAACCGGGCCTTTACGGC

TACAAATACCTGCTGGTGTTCGTGGACACTTTCTCGGGATGGATCGAGGCCTTCCC

GACTAAAAAGGAAACTGCAAAAGTGGTGACTAAGAAGCTGCTGGAGGAGATTTTCC

CCCGCTTTGGCATGCCGCAGGTATTGGGAACTGACAATGGGCCTGCCTTCGTCTC

CAAGGTGAGTCAGACAGTGGCCGATCTGTTGGGGATTGATTGGAAATTACATTGTG

CATACAGACCCCAAAGCTCAGGTCAGGTAGAAAGAATGAATAGGACCATCAAGGAG

ACTTTAACTAAATTAACGCTTGCAACTGGCTCTAGAGACTGGGTGCTCCTACTCCCC

TTAGCCCTGTACCGAGCCCGCAACACGCCGGGCCCCCATGGCCTCACCCCATATG

AGATCTTATATGGGGCACCCCCGCCCCTTGTAAACTTCCCTGACCCTGACATGACC

AGAGTTACTAACAGCCCCTCTCTCCAAGCTCACTTACAGGCTCTCTACTTAGTCCAG

CACGAAGTTTGGAGACCACTGGCGGCAGCTTACCAAGAACAACTGGACCGGCCGG
```

-continued

```
TGGTGCCTCACCCTTACCGGGTCGGCGACACAGTGTGGGTCCGCCGACATCAAAC

CAAGAACCTAGAACCTCGCTGGAAAGGACCTTACACAGTCCTGCTGACCACCCCA

CCGCCCTCAAAGTAGACGGTATCGCAGCTTGGATACACGCAGCCCACGTAAAGGC

GGCCGACACCGAGAGTGGACCATCCTCTGGACGGACATGGCGCGTTCAACGCTCT

CAAAACCCCCTCAAGATAAGATTAACCCGTGGAAGCCCTTAG
```

(Gag and Pol polyproteins codon-shuffled variant)

SEQ ID NO: 2

```
ATGGGTCAGACGGTGACTACTCCGCTTTCACTCACACTCGGTCATTGGAAAGACGT

TGAGCGAATCGCGCACAATCAGAGTGTGGACGTAAAAAAGCGCCGCTGGGTTACG

TTCTGTTCTGCTGAGTGGCCTACGTTTAATGTAGGGTGGCCAAGGGATGGCACTTT

CAACAGGGATCTGATAACACAGGTAAAGATAAAAGTTTTTAGTCCAGGCCCACACG

GTCATCCTGATCAGGTGCCTTACATTGTAACATGGGAAGCACTGGCGTTTGATCCT

CCGCCGTGGGTTAAACCCTTTGTACACCCCAAACCCCCTCCACCACTCCCACCCTC

TGCCCCATCATTGCCGTTGGAACCGCCCAGGTCTACGCCCCCCCGCTCATCCCTTT

ACCCTGCTCTGACACCTAGCCTTGGTGCCAAACCCAAGCCACAAGTGCTCTCAGAC

AGCGGCGGCCCTCTGATAGATTTGCTGACTGAAGATCCGCCTCCTTATCGCGACCC

GCGGCCTCCACCGTCAGATAGGGATGGCAATGGCGGCGAAGCCACACCCGCAGG

TGAGGCCCCTGATCCAAGTCCCATGGCTTCTCGACTTCGAGGCCGACGGGAGCCG

CCTGTCGCTGATAGTACGACTTCACAAGCATTCCCTTTGAGAGCGGGGGGGAATG

GGCAATTGCAATATTGGCCCTTTAGCAGCAGTGACCTGTACAATTGGAAAAACAATA

ACCCTTCTTTTAGTGAGGATCCTGGTAAGCTTACGGCTTTGATAGAATCCGTGCTTA

TTACACATCAGCCGACATGGGATGACTGCCAACAACTCTTGGGTACATTGCTGACG

GGTGAAGAAAAACAGCGCGTGCTCTTGGAAGCCAGGAAAGCTGTACGCGGCGACG

ACGGTCGGCCCACACAGCTTCCTAACGAAGTCGACGCCGCTTTTCCTCTCGAGCG

GCCAGATTGGGATTACACAACCCAGGCCGGCCGGAACCATTTGGTACATTACCGG

CAACTCTTGTTGGCAGGGTTGCAAAACGCTGGTCGGAGCCCCACGAACTTGGCGA

AAGTGAAGGGTATCACCCAAGGCCCAAACGAGTCACCTTCAGCTTTTCTCGAACGA

CTTAAAGAAGCCTACAGACGATACACTCCGTACGATCCAGAGGACCCGGGCCAGG

AAACCAACGTATCTATGTCTTTCATTTGGCAGAGCGCTCCAGACATCGGGCGAAAA

CTGGAACGCCTCGAAGACCTGAAGAATAAAACTCTCGGTGACCTCGTTCGCGAAGC

CGAGAAAATTTTTAATAAAAGAGAAACTCCGGAAGAGCGCGAGGAAAGAATTAGGC

GCGAGACGGAGGAAAAAGAAGAACGGAGGAGAACCGAGGACGAACAAAAGGAGA

AAGAGCGAGACCGACGGCGCCACAGAGAAATGAGCAAACTGCTTGCCACCGTGGT

GAGCGGTCAAAAGCAAGACCGACAGGGAGGGGAGCGGAGACGAAGTCAGCTCGA

CAGGGACCAGTGTGCTTATTGTAAAGAAAGGGCCACTGGGCTAAAGACTGCCCC

AAAAAACCGAGAGGCCCCAGGGGTCCGAGACCGCAGACCTCTTTGTTGACTTTGG

ATGATTAAGGCGGACAGGGTCAAGAGCCTCCACCGGAACCACGCATAACTCTCAAA

GTGGGAGGCCAGCCAGTAACGTTTCTCGTCGACACAGGAGCACAACATTCAGTTCT

TACTCAAAACCCAGGGCCGCTGAGTGACAAGTCTGCTTGGGTGCAGGGAGCTACT

GGAGGGAAGCGGTACCGGTGGACGACGGACCGGAAAGTGCATCTGGCGACGGGT

AAAGTAACACACTCTTTCTTGCATGTACCGGATTGCCCCTACCCACTTCTCGGCCG

CGACTTGCTTACAAAACTTAAAGCTCAGATCCATTTCGAGGGAAGCGGGGCTCAGG
```

-continued

```
TAATGGGCCCGATGGGGCAGCCTCTTCAGGTCCTGACCTTGAATATCGAAGACGA

GTATCGCTTGCATGAAACCTCTAAGGAACCTGATGTGTCTCTGGGGTCAACGTGGC

TGTCCGACTTTCCTCAGGCATGGGCTGAAACCGGAGGCATGGGTTTGGCGGTCAG

ACAGGCACCGCTTATTATTCCCCTTAAGGCGACGTCTACGCCCGTCTCAATAAAAC

AATACCCAATGTCTCAAGAAGCCCGGCTGGGAATCAAGCCTCACATTCAAAGACTG

CTCGATCAGGGCATCCTCGTCCCTTGCCAGAGCCCGTGGAATACGCCTCTGTTGC

CGGTGAAGAAGCCCGGCACGAATGACTATCGGCCTGTCCAGGACCTCCGGGAAGT

GAACAAGAGAGTGGAGGACATACACCCTACAGTGCCCAATCCCTATAATCTGCTGT

CCGGTCTCCCTCCTTCCCATCAATGGTATACGGTCCTCGATCTGAAGGATGCCTTT

TTTTGTCTTAGGCTTCACCCTACGTCTCAACCCCTCTTcGCCTTCGAGTGGCGCGA

TCCCGAAATGGGGATCAGCGGACAACTTACTTGGACTAGGCTTCCCCAGGGGTTC

AAAAATAGTCCCACACTGTTCGATGAGGCTCTGCACAGGGACTTGGCGGATTTCCG

GATACAACACCCTGACCTCATTTTGCTTCAATATGTCGACGATCTTCTCCTGGCGGC

CACATCTGAACTCGATTGCCAACAAGGAACTAGGGCTCTTCTGCAAACTCTCGGAA

ACTTGGGTTATCGGGCTAGTGCAAAAAAGGCTCAGATATGCCAGAAACAAGTAAAG

TACCTCGGCTATCTCCTGAAAGAAGGGCAACGGTGGCTCACAGAAGCAAGGAAGG

AAACGGTGATGGGCCAGCCAACTCCGAAAACGCCCCGACAGTTGAGAGAGTTCCT

GGGTACAGCGGGGTTTTGCCGACTCTGGATCCCGGGCTTTGCGGAAATGGCCGCC

CCACTGTATceGCTTACCAAGACGGGAACGCTTTTTAACTGGGGGCCTGACCAACA

AAAGGCATACCAGGAAATCAAGCAAGCACTGCTCACAGCTCCAGCGCTCGGTCTC

CCGGACTTGACTAAACCCTTTGAACTTTTTGTTGATGAGAAGCAAGGCTATGCAAAG

GGCGTGCTTACACAGAAGTTGGGTCCATGGAGAAGGCCGGTTGCCTATTTGTCCAA

AAAACTGGACCCTGTGGCAGCTGGCTGGCCCCCATGCTTGAGGATGGTAGCTGCC

ATAGCTGTGCTGACCAAGGACGCAGGGAAACTTACCATGGGCCAACCTCTTGTGAT

ACTTGCACCGCATGCTGTTGAAGCCCTGGTCAAGCAACCGCCGGACCGCTGGCTC

TCTAACGCGAGGATGACGCACTACCAAGCTTTGCTCCTCGACACGGACCGGGTCC

AATTCGGTCCTGTCGTCGCGCTCAATCCCGCGACACTCCTCCCCCTTCCTGAGGAA

GGGCTGCAACATGACTGTCTCGACATACTTGCAGAAGCACACGGCACGCGGTCAG

ACTTGACAGACCAGCCTCTCCCTGATGCCGACCACACTTGGTATACCGATGGCAGT

AGTTTTTTGCAGGAAGGTCAGCGAAAGGCTGGCGCCGCAGTCACCACAGAAACTG

AGGTAATTTGGGCGAGGGCTCTCCCAGCTGGGACATCTGCTCAACGCGCGGAACT

CATTGCACTCACCCAAGCCCTGAAGATGGCAGAAGGAAAAAAATTGAATGTCTACA

CTGATTCCCGGTATGCTTTTGCCACGGCGCATATCCATGGGGAGATATATCGACGC

CGAGGTCTGCTTACGTCTGAAGGTAAGGAGATTAAAAACAAAGACGAGATCCTCGC

CCTTCTGAAGGCACTGTTCTTGCCAAAAAGACTGAGTATCATACACTGTCCTGGACA

CCAGAAAGGTAATTCAGCCGAAGCGAGGGGTAACCGGATGGCAGATCAAGCAGCA

CGGGAAGTCGCTACCCGAGAAACCCCCGGAACCTCCACCCTTTTGATCGAGAACA

GTACTCCTTACACTCACGAGCATTTCCATTATACAGTGACGGACACGAAAGATTTGA

CGAAACTGGGTGCAACGTACGATAGTGCAAAAAAATACTGGGTATATCAGGGCAAA

CCCGTGATGCCTGACCAGTTCACGTTCGAGCTTCTGGATTTCCTCCACCAGCTTAC
```

-continued

```
GCATTTGTCTTTTTCCAAGACGAAAGCGCTTCTGGAACGGTCTCCGTCCCCATATTA

TATGTTAATAGAGATAGGACCTTGAAAAATATAACAGAAACCTGCAAGGCTTGTGC

TCAAGTGAATGCTTCCAAGAGCGCAGTCAAACAAGGTACGAGGGTCAGAGGCCAC

AGGCCAGGAACCCATTGGGAGATCGACTTCACTGAGGTGAAACCAGGCCTTTACG

GCTACAAGTACCTTCTTGTTTTTGTTGATACGTTCTCCGGCTGGATCGAGGCCTTTC

CAACTAAGAAGGAGACTGCGAAAGTGGTCACAAAGAAACTCCTGGAAGAAATCTTC

CCGCGCTTTGGGATGCCTCAGGTCCTTGGGACCGATAACGGGCCTGCTTTTGTATC

CAAAGTCAGCCAAACAGTCGCCGACCTCTTGGGAATCGATTGGAAACTGCACTGTG

CCTATCGCCCCAGTCAAGCGGCCAAGTAGAAAGGATGAACAGGACAATCAAAGA

AACTCTCACCAAGCTGACTTTGGCAACTGGGTCACGCGACTGGGTCTTGCTTTTGC

CACTTGCTCTTTACCGCGCTCGCAACACACCCGGTCCCCACGGTCTCACTCCATAT

GAGATTTTGTATGGCGCACCACCCCCTCTCGTGAATTTTCCCGATCCTGACATGAC

GAGGGTCACCAACTCTCCCTCTTTGCAGGCTCATCTTCAGGCGCTTTATCTTGTGC

AGCACGAGGTTTGGAGACCTCTTGCAGCTGCATACCAAGAACAGCTTGACAGGCCT

GTCGTGCCACATCCGTACCGGGTCGGAGATACGGTATGGGTAAGGAGACACCAAA

CTAAAAACCTGGAGCCAAGATGGAAAGGGCCTTATACTGTTCTCCTGACTACGCCT

ACTGCTCTCAAGGTTGATGGCATAGCAGCCTGGATTCATGCGGCCCATGTTAAGGC

TGCAGATACAGAATCCGGTCCCTCATCCGGAAGGACATGGCGGGTTCAAAGGTCC

CAAAACCCCCTCAAAATTCGACTCACACGCGGCTCCCCGTAA
```

(Gag and Pol polyprotein codon-shuffled variant)

SEQ ID NO: 3

```
ATGGGCCAGACCGTGACCACCCCCCTGAGCCTGACCCTGGGCCACTGGAAGGAC

GTGGAGCGCATCGCCCACAACCAGAGCGTGGACGTGAAGAAGCGCCGCTGGGTG

ACCTTCTGCAGCGCCGAGTGGCCCACCTTCAACGTGGGCTGGCCCCGCGACGGC

ACCTTCAACCGCGACCTGATCACCCAGGTGAAGATCAAGGTGTTCAGCCCCGGCC

CCCACGGCCACCCCGACCAGGTGCCCTACATCGTGACCTGGGAGGCCCTGGCCTT

CGACCCCCCCCCCTGGGTGAAGCCCTTCGTGCACCCCAAGCCCCCCCCCCCCCCT

GCCCCCCAGCGCCCCCAGCCTGCCCCTGGAGCCCCCCGCAGCACCCCCCCCCG

CAGCAGCCTGTACCCCGCCCTGACCCCCAGCCTGGGCGCCAAGCCCAAGCCCCA

GGTGCTGAGCGACAGCGGCGGCCCCCTGATCGACCTGCTGACCGAGGACCCCCC

CCCCTACCGCGACCCCGCCCCCCCCCAGCGACCGCGACGGCAACGGCGGCGA

GGCCACCCCGCCGGCGAGGCCCCGACCCCAGCCCCATGGCCAGCCGCCTGC

GCGGCCGCCGCGAGCCCCCGTGGCCGACAGCACCACCAGCCAGGCCTTCCCCC

TGCGCGCCGGCGGCAACGGCCAGCTGCAGTACTGGCCCTTCAGCAGCAGCGACC

TGTACAACTGGAAGAACAACAACCCCAGCTTCAGCGAGGACCCCGGCAAGCTGAC

CGCCCTGATCGAGAGCGTGCTGATCACCCACCAGCCCACCTGGGACGACTGCCAG

CAGCTGCTGGGCACCCTGCTGACCGGCGAGGAGAAGCAGCGCGTGCTGCTGGAG

GCCCGCAAGGCCGTGCGCGGCGACGACGGCCGCCCCACCCAGCTGCCCAACGA

GGTGGACGCCGCCTTCCCCCTGGAGCGCCCCGACTGGGACTACACCACCCAGGC

CGGCCGCAACCACCTGGTGCACTACCGCCAGCTGCTGCTGGCCGGCCTGCAGAA

CGCCGGCCGCAGCCCCACCAACCTGGCCAAGGTGAAGGGCATCACCCAGGGCCC

CAACGAGAGCCCCAGCGCCTTCCTGGAGCGCCTGAAGGAGGCCTACCGCCGCTA
```

-continued

```
CACCCCCTACGACCCCGAGGACCCCGGCCAGGAGACCAACGTGAGCATGAGCTTC

ATCTGGCAGAGCGCCCCCGACATCGGCCGCAAGCTGGAGCGCCTGGAGGACCTG

AAGAACAAGACCCTGGGCGACCTGGTGCGCGAGGCCGAGAAGATCTTCAACAAGC

GCGAGACCCCCGAGGAGCGCGAGGAGCGCATCCGCCGCGAGACCGAGGAGAAG

GAGGAGCGCCGCCGCACCGAGGACGAGCAGAAGGAGAAGGAGCGCGACCGCCG

CCGCCACCGCGAGATGAGCAAGCTGCTGGCCACCGTGGTGAGCGGCCAGAAGCA

GGACCGCCAGGGCGGCGAGCGCCGCCGCAGCCAGCTGGACCGCGACCAGTGCG

CCTACTGCAAGGAGAAGGGCCACTGGGCCAAGGACTGCCCCAAGAAGCCCCGCG

GCCCCCGCGGCCCCCGCCCCCAGACCAGCCTGCTGACCCTGGACGACTAAGGCG

GCCAGGGCCAGGAGCCCCCCCCGAGCCCCGCATCACCCTGAAGGTGGGCGGCC

AGCCCGTGACCTTCCTGGTGGACACCGGCGCCCAGCACAGCGTGCTGACCCAGAA

CCCCGGCCCCCTGAGCGACAAGAGCGCCTGGGTGCAGGGCGCCACCGGCGGCA

AGCGCTACCGCTGGACCACCGACCGCAAGGTGCACCTGGCCACCGGCAAGGTGA

CCCACAGCTTCCTGCACGTGCCCGACTGCCCCTACCCCTGCTGGGCCGCGACCT

GCTGACCAAGCTGAAGGCCCAGATCCACTTCGAGGGCAGCGGCGCCCAGGTGAT

GGGCCCCATGGGCCAGCCCCTGCAGGTGCTGACCCTGAACATCGAGGACGAGTA

CCGCCTGCACGAGACCAGCAAGGAGCCCGACGTGAGCCTGGGCAGCACCTGGCT

GAGCGACTTCCCCCAGGCCTGGGCCGAGACCGGCGGCATGGGCCTGGCCGTGCG

CCAGGCCCCCCTGATCATCCCCCTGAAGGCCACCAGCACCCCCGTGAGCATCAAG

CAGTACCCCATGAGCCAGGAGGCCCGCCTGGGCATCAAGCCCCACATCCAGCGC

CTGCTGGACCAGGGCATCCTGGTGCCCTGCCAGAGCCCCTGGAACACCCCCCTGC

TGCCCGTGAAGAAGCCCGGCACCAACGACTACCGCCCCGTGCAGGACCTGCGCG

AGGTGAACAAGCGCGTGGAGGACATCCACCCCACCGTGCCCAACCCCTACAACCT

GCTGAGCGGCCTGCCCCCCAGCCACCAGTGGTACACCGTGCTGGACCTGAAGGA

CGCCTTCTTCTGCCTGCGCCTGCACCCCACCAGCCAGCCCCTGTTCGCCTTCGAG

TGGCGCGACCCCGAGATGGGCATCAGCGGCCAGCTGACCTGGACCCGCCTGCCC

CAGGGCTTCAAGAACAGCCCCACCCTGTTCGACGAGGCCCTGCACCGCGACCTGG

CCGACTTCCGCATCCAGCACCCCGACCTGATCCTGCTGCAGTACGTGGACGACCT

GCTGCTGGCCGCCACCAGCGAGCTGGACTGCCAGCAGGGCACCCGCGCCCTGCT

GCAGACCCTGGGCAACCTGGGCTACCGCGCCAGCGCCAAGAAGGCCCAGATCTG

CCAGAAGCAGGTGAAGTACCTGGGCTACCTGCTGAAGGAGGGCCAGCGCTGGCT

GACCGAGGCCCGCAAGGAGACCGTGATGGGCCAGCCCACCCCCAAGACCCCCCG

CCAGCTGCGCGAGTTCCTGGGCACCGCCGGCTTCTGCCGCCTGTGGATCCCCGG

CTTCGCCGAGATGGCCGCCCCCCTGTACCCCCTGACCAAGACCGGCACCCTGTTC

AACTGGGGCCCCGACCAGCAGAAGGCCTACCAGGAGATCAAGCAGGCCCTGCTG

ACCGCCCCCGCCCTGGGCCTGCCCGACCTGACCAAGCCCTTCGAGCTGTTCGTGG

ACGAGAAGCAGGGCTACGCCAAGGGCGTGCTGACCCAGAAGCTGGGCCCCTGGC

GCCGCCCCGTGGCCTACCTGAGCAAGAAGCTGGACCCCGTGGCCGCCGGCTGGC

CCCCCTGCCTGCGCATGGTGGCCGCCATCGCCGTGCTGACCAAGGACGCCGGCA

AGCTGACCATGGGCCAGCCCCTGGTGATCCTGGCCCCCCACGCCGTGGAGGCCC
```

-continued

```
TGGTGAAGCAGCCCCCCGACCGCTGGCTGAGCAACGCCCGCATGACCCACTACCA

GGCCCTGCTGCTGGACACCGACCGCGTGCAGTTCGGCCCCGTGGTGGCCCTGAA

CCCCGCCACCCTGCTGCCCCTGCCCGAGGAGGGCCTGCAGCACGACTGCCTGGA

CATCCTGGCCGAGGCCCACGGCACCCGCAGCGACCTGACCGACCAGCCCCTGCC

CGACGCCGACCACACCTGGTACACCGACGGCAGCAGCTTCCTGCAGGAGGGCCA

GCGCAAGGCCGGCGCCGCCGTGACCACCGAGACCGAGGTGATCTGGGCCCGCG

CCCTGCCCGCCGGCACCAGCGCCCAGCGCGCCGAGCTGATCGCCCTGACCCAGG

CCCTGAAGATGGCCGAGGGCAAGAAGCTGAACGTGTACACCGACAGCCGCTACGC

CTTCGCCACCGCCCACATCCACGGCGAGATCTACCGCCGCCGCGGCCTGCTGACC

AGCGAGGGCAAGGAGATCAAGAACAAGGACGAGATCCTGGCCCTGCTGAAGGCC

CTGTTCCTGCCCAAGCGCCTGAGCATCATCCACTGCCCCGGCCACCAGAAGGGCA

ACAGCGCCGAGGCCCGCGGCAACCGCATGGCCGACCAGGCCGCCCGCGAGGTG

GCCACCCGCGAGACCCCCGGCACCAGCACCCTGCTGATCGAGAACAGCACCCCC

TACACCCACGAGCACTTCCACTACACCGTGACCGACACCAAGGACCTGACCAAGCT

GGGCGCCACCTACGACAGCGCCAAGAAGTACTGGGTGTACCAGGGCAAGCCCGT

GATGCCCGACCAGTTCACCTTCGAGCTGCTGGACTTCCTGCACCAGCTGACCCAC

CTGAGCTTCAGCAAGACCAAGGCCCTGCTGGAGCGCAGCCCCAGCCCCTACTACA

TGCTGAACCGCGACCGCACCCTGAAGAACATCACCGAGACCTGCAAGGCCTGCGC

CCAGGTGAACGCCAGCAAGAGCGCCGTGAAGCAGGGCACCCGCGTGCGCGGCCA

CCGCCCCGGCACCCACTGGGAGATCGACTTCACCGAGGTGAAGCCCGGCCTGTA

CGGCTACAAGTACCTGCTGGTGTTCGTGGACACCTTCAGCGGCTGGATCGAGGCC

TTCCCCACCAAGAAGGAGACCGCCAAGGTGGTGACCAAGAAGCTGCTGGAGGAGA

TCTTCCCCCGCTTCGGCATGCCCCAGGTGCTGGGCACCGACAACGGCCCCGCCTT

CGTGAGCAAGGTGAGCCAGACCGTGGCCGACCTGCTGGGCATCGACTGGAAGCT

GCACTGCGCCTACCGCCCCCAGAGCAGCGGCCAGGTGGAGCGCATGAACCGCAC

CATCAAGGAGACCCTGACCAAGCTGACCCTGGCCACCGGCAGCCGCGACTGGGT

GCTGCTGCTGCCCCTGGCCCTGTACCGCGCCCGCAACACCCCCGGCCCCCACGG

CCTGACCCCCTACGAGATCCTGTACGGCGCCCCCCCCCCCCTGGTGAACTTCCCC

GACCCCGACATGACCCGCGTGACCAACAGCCCCAGCCTGCAGGCCCACCTGCAG

GCCCTGTACCTGGTGCAGCACGAGGTGTGGCGCCCCCTGGCCGCCGCCTACCAG

GAGCAGCTGGACCGCCCCGTGGTGCCCCACCCCTACCGCGTGGGCGACACCGTG

TGGGTGCGCCGCCACCAGACCAAGAACCTGGAGCCCCGCTGGAAGGGCCCCTAC

ACCGTGCTGCTGACCACCCCCACCGCCCTGAAGGTGGACGGCATCGCCGCCTGG

ATCCACGCCGCCCACGTGAAGGCCGCCGACACCGAGAGCGGCCCCAGCAGCGGC

CGCACCTGGCGCGTGCAGCGCAGCCAGAACCCCCTGAAGATCCGCCTGACCCGC

GGCAGCCCCTAA

SEQ ID NO: 4: Wildtype Gag and Pol polyproteins
ATGGGCCAGACTGTTACCACTCCCTTAAGTTTGACCTTAGGTCACTGGAAAGATGT

CGAGCGGATCGCTCACAACCAGTCGGTAGATGTCAAGAAGAGACGTTGGGTTACC

TTCTGCTCTGCAGAATGGCCAACCTTTAACGTCGGATGGCCGCGAGACGGCACCTT

TAACCGAGACCTCATCACCCAGGTTAAGATCAAGGTCTTTTCACCTGGccCGCATG
```

-continued

```
GACACCCAGACCAGGTCCCCTACATCGTGACCTGGGAAGCCTTGGCTTTTGACCC

CCCTCCCTGGGTCAAGCCCTTTGTACACCCTAAGCCTCCGCCTCCTCTTCCTCCAT

CCGCCCCGTCTCTCCCCCTTGAACCTCCTCGTTCGACCCCGCCTCGATCCTCCCTT

TATCCAGCCCTCACTCCTTCTCTAGGCGCCAAACCTAAACCTCAAGTTCTTTCTGAC

AGTGGGGGGCCGCTCATCGACCTACTTACAGAAGACCCCCCGCCTTATAGGGACC

CAAGACCACCCCCTTCCGACAGGGACGGAAATGGTGGAGAAGCGACCCCTGCGG

GAGAGGCACCGGACCCCTCCCCAATGGCATCTCGCCTACGTGGGAGACGGGAGC

CCCCTGTGGCCGACTCCACTACCTCGCAGGCATTCCCCCTCCGCGCAGGAGGAAA

CGGACAGCTTCAATACTGGCCGTTCTCCTCTTCTGACCTTTACAACTGGAAAAATAA

TAACCCTTCTTTTTCTGAAGATCCAGGTAAACTGACAGCTCTGATCGAGTCTGTTCT

CATCACCCATCAGCCCACCTGGGACGACTGTCAGCAGCTGTTGGGGACTCTGCTG

ACCGGAGAAGAAAAACAACGGGTGCTCTTAGAGGCTAGAAAGGCGGTGCGGGGC

GATGATGGGCGCCCCACTCAACTGCCCAATGAAGTCGATGCCGCTTTTCCCCTCGA

GCGCCCAGACTGGGATTACACCACCCAGGCAGGTAGGAACCACCTAGTCCACTAT

CGCCAGTTGCTCCTAGCGGGTCTCCAAAACGCGGGCAGAAGCCCCACCAATTTGG

CCAAGGTAAAAGGAATAACACAAGGGCCCAATGAGTCTCCCTCGGCCTTCCTAGAG

AGACTTAAGGAAGCCTATCGCAGGTACACTCCTTATGACCCTGAGGACCCAGGGCA

AGAAACTAATGTGTCTATGTCTTTCATTTGGCAGTCTGCCCCAGACATTGGGAGAAA

GTTAGAGAGGTTAGAAGATTTAAAAAACAAGACGCTTGGAGATTTGGTTAGAGAGG

CAGAAAAGATCTTTAATAAACGAGAAACCCCGGAAGAAAGAGAGGAACGTATCAGG

AGAGAAACAGAGGAAAAAGAAGAACGCCGTAGGACAGAGGATGAGCAGAAAGAGA

AAGAAAGAGATCGTAGGAGACATAGAGAGATGAGCAAGCTATTGGCCACTGTCGTT

AGTGGACAGAAACAGGATAGACAGGGAGGAGAACGAAGGAGGTCCCAACTCGATC

GCGACCAGTGTGCCTACTGCAAAGAAAAGGGGCACTGGGCTAAAGATTGTCCCAA

GAAACCACGAGGACCTCGGGGACCAAGACCCCAGACCTCCCTCCTGACCCTAGAT

GACTAGGGAGGTCAGGGTCAGGAGCCCCCCCCTGAACCCAGGATAACCCTCAAAG

TCGGGGGGCAACCCGTCACCTTCCTGGTAGATACTGGGGCCCAACACTCCGTGCT

GACCCAAAATCCTGGACCCCTAAGTGATAAGTCTGCCTGGGTCCAAGGGGCTACT

GGAGGAAAGCGGTATCGCTGGACCACGGATCGCAAAGTACATCTAGCTACCGGTA

AGGTCACCCACTCTTTCCTCCATGTACCAGACTGTCCCTATCCTCTGTTAGGAAGA

GATTTGCTGACTAAACTAAAAGCCCAAATCCACTTTGAGGGATCAGGAGCTCAGGT

TATGGGACCAATGGGGCAGCCCCTGCAAGTGTTGACCCTAAATATAGAAGATGAGT

ATCGGCTACATGAGACCTCAAAAGAGCCAGATGTTTCTCTAGGGTCCACATGGCTG

TCTGATTTTCCTCAGGCCTGGGCGGAAACCGGGGGCATGGGACTGGCAGTTCGCC

AAGCTCCTCTGATCATACCTCTGAAAGCAACCTCTACCCCCGTGTCCATAAAACAAT

ACCCCATGTCACAAGAAGCCAGACTGGGGATCAAGCCCCACATACAGAGACTGTT

GGACCAGGGAATACTGGTACCCTGCCAGTCCCCCTGGAACACGCCCCTGCTACCC

GTTAAGAAACCAGGGACTAATGATTATAGGCCTGTCCAGGATCTGAGAGAAGTCAA

CAAGCGGGTGGAAGACATCCACCCCACCGTGCCCAACCCTTACAACCTCTTGAGC

GGGCTCCCACCGTCCCACCAGTGGTACACTGTGCTTGATTTAAAGGATGCCTTTTT

CTGCCTGAGACTCCACCCCACCAGTCAGCCTCTCTTCGCCTTTGAGTGGAGAGATC
```

-continued

```
CAGAGATGGGAATCTCAGGACAATTGACCTGGACCAGACTCCCACAGGGTTTCAAA

AACAGTCCCACCCTGTTTGATGAGGCACTGCACAGAGACCTAGCAGACTTCCGGAT

CCAGCACCCAGACTTGATCCTGCTACAGTACGTGGATGACTTACTGCTGGCCGCCA

CTTCTGAGCTAGACTGCCAACAAGGTACTCGGGCCCTGTTACAAACCCTAGGGAAC

CTCGGGTATCGGGCCTCGGCCAAGAAAGCCCAAATTTGCCAGAAACAGGTCAAGT

ATCTGGGGTATCTTCTAAAAGAGGGTCAGAGATGGCTGACTGAGGCAGAAAAGA

GACTGTGATGGGGCAGCCTACTCCGAAGACCCCTCGACAACTAAGGGAGTTCCTA

GGGACGGCAGGCTTCTGTCGCCTCTGGATCCCTGGGTTTGCAGAAATGGCAGCCC

CCTTGTACCCTCTCACCAAAACGGGGACTCTGTTTAATTGGGGCCCAGACCAACAA

AAGGCCTATCAAGAAATCAAGCAAGCTCTTCTAACTGCCCCAGCCCTGGGGTTGCC

AGATTTGACTAAGCCCTTTGAACTCTTTGTCGACGAGAAGCAGGGCTACGCCAAAG

GCGTCCTAACGCAAAAGCTGGGACCTTGGCGTCGGCCGGTGGCCTACCTGTCTAA

AAAGCTAGACCCAGTGGCAGCTGGCTGGCCCCCTGCCTACGGATGGTGGCAGC

CATTGCAGTTCTGACAAAAGATGCTGGCAAGCTCACTATGGGACAGCCGTTGGTCA

TTCTGGCCCCCATGCCGTAGAGGCACTAGTTAAGCAACCCCCTGATCGCTGGCT

CTCCAATGCCCGGATGACCCATTACCAAGCCCTGCTCCTGGACACGGACCGGGTC

CAGTTCGGGCCAGTAGTGGCCCTAAATCCAGCTACGCTGCTCCCTCTGCCTGAGG

AGGGGCTGCAACATGACTGCCTTGACATCTTGGCTGAAGCCCACGGAACTAGATCA

GATCTTACGGACCAGCCCCTCCCAGACGCCGACCACACCTGGTACACGGATGGGA

GCAGCTTCCTGCAAGAAGGGCAGCGTAAGGCCGGAGCAGCGGTGACCACTGAGA

CTGAGGTAATCTGGGCCAGGGCATTGCCAGCCGGGACATCGGCCCAAAGAGCTGA

ACTGATAGCGCTCACCCAAGCCCTAAAGATGGCAGAAGGTAAGAAGCTAAATGTTT

ATACTGATAGCCGTTACGCTTTTGCCACCGCCCATATTCATGGAGAAATATACAGAA

GGCGCGGGTTGCTCACATCAGAAGGAAAAGAGATCAAGAACAAGGACGAGATCTT

AGCCCTACTAAAGGCTCTCTTCTTGCCCAAAAGACTTAGCATAATTCATTGCCCGGG

ACATCAAAAAGGAAACAGCGCAGAGGCCAGGGGCAACCGGATGGCCGACCAAGC

GGCCCGAGAAGTAGCCACTAGAGAAACTCCAGGAACTTCCACACTTCTGATAGAAA

ACTCAACCCCCTATACCCATGAACACTTTCACTATACAGTAACTGACACAAAGGATT

TGACCAAACTAGGAGCCACTTATGACAGTGCGAAGAAATATTGGGTCTATCAAGGA

AAGCCTGTTATGCCTGATCAATTCACCTTTGAGTTACTAGACTTTCTTCACCAATTGA

CCCACCTCAGCTTCTCAAAAACAAAGGCTCTCCTAGAGAAGCCCCAGTCCCTAC

TACATGCTGAACCGGGATCGAACACTCAAAAATATCACTGAGACCTGCAAAGCTTG

TGCACAAGTCAATGCCAGCAAGTCTGCCGTTAAGCAAGGAACTAGGGTCCGCGGG

CATCGGCCTGGCACACACTGGGAGATCGATTTCACCGAGGTAAAACCTGGATTGTA

TGGCTATAAGTATCTTTTAGTTTTTGTAGATACTTTTTCTGGCTGGATAGAAGCTTTC

CCAACTAAGAAAGAAACCGCCAAGGTCGTGACCAAGAAACTGCTAGAAGAGATCTT

CCCTAGGTTCGGCATGCCGCAGGTATTGGGAACTGACAATGGGCCTGCCTTCGTC

TCCAAGGTGAGTCAGACAGTGGCCGATCTGTTGGGGATTGATTGGAAATTACATTG

TGCATACAGACCCCAAAGCTCAGGTCAGGTAGAAAGAATGAATAGGACCATCAAGG

AGACTTTAACTAAATTAACGCTTGCAACTGGCTCTAGAGACTGGGTGCTCCTACTCC
```

-continued
CCTTAGCCCTGTACCGAGCCCGCAACACGCCGGGCCCCCATGGCCTCACCCCATA

TGAGATCTTATATGGGGCACCCCCGCCCCTTGTAAACTTCCCTGACCCTGACATGA

CCAGAGTTACTAACAGCCCCTCTCTCCAAGCTCACTTACAGGCTCTCTACTTAGTCC

AGCACGAAGTTTGGAGACCACTGGCGGCAGCTTACCAAGAACAACTGGACCGGCC

GGTGGTGCCTCACCCTTACCGGGTCGGCGACACAGTGTGGGTCCGCCGACATCAA

ACCAAGAACCTAGAACCTCGCTGGAAAGGACCTTACACAGTCCTGCTGACCACCCC

CACCGCCCTCAAAGTAGACGGTATCGCAGCTTGGATACACGCAGCCCACGTAAAG

GCGGCCGACACCGAGAGTGGACCATCCTCTGGACGGACATGGCGCGTTCAACGCT

CTCAAAACCCCCTCAAGATAAGATTAACCCGTGGAAGCCCTTAA

SEQ ID NO: 5: (RD114 ENV protein codon-optimised variant)
ATGAAGCTGCCGACGGGAATGGTGATCCTGTGCAGCCTGATTATCGTGCGCGCGG

GGTTCGACGACCCGAGAAAGGCTATCGCTATCGTGCAAAAGCAGCACGGGAAACC

ATGCGAATGCAGCGGTGGCCAGGTGTCAGAGGCCCCACCGAACTCAATCCAGCAG

GTCACCTGCCCCGGTAAAACCGCATACCTGATGACCAATCAAAGTGGAAGTGCCG

GGTGACCCCGAAGAATCTGACTCCAAGCGGGGAGAACTGCAGAACTGCCCCTGC

AATACTTTCCAGGATTCAATGCACTCCTCCTGTTACACCGAATACCGCCAGTGCAG

GGCAAATAACAAAACGTACTACACTGCGACCCTGCTGAAGATCCGCTCCGGCTCCC

TAAATGAAGTGCAGATCCTGCAGAATCCAAACCAACTGTTGCAGAGCCCGTGCAGA

GGCAGCATCAATCAGCCGGTCTGCTGGAGCGCCACCGCACCTATCCACATCTCAG

ACGGAGGGGACCGCTCGATACCAAGCGCGTGTGGACCGTGCAAAAGCGGCTAG

AGCAGATCCACAAAGCTATGCACCCGGAACTGCAATACCACCCGCTGGCGCTTCC

AAAGGTCCGCGACGATCTGTCGCTGGACGCGCGGACCTTCGACATCTTGAATACTA

CCTTCCGCCTGCTGCAGATGTCGAATTTCAGCCTGGCACAGGATTGTTGGCTGTGC

CTGAAGCTGGGTACTCCGACCCCGCTGGCCATCCCCACCCCGTCACTGACTTACT

CACTCGCAGACTCGTTGGCAAACGCCTCCTGCCAGATTATCCCACCTCTGCTGGTG

CAGCCGATGCAGTTCTCGAACTCCAGCTGCCTGTCATCACCATTCATCAACGACAC

TGAACAGATTGATCTGGGAGCAGTGACTTTCACCAACTGCACTTCAGTGGCCAACG

TCTCCTCGCCACTGTGCGCTCTGAACGGGTCCGTGTTCCTGTGTGGAAACAATATG

GCGTACACTTACCTGCCGCAAAACTGGACTGGCCTGTGCGTGCAAGCGTCACTGC

TGCCTGACATCGACATTATCCCAGGAGACGAGCCCGTCCCGATCCCGGCAATCGA

CCACTACATTCACCGCCCGAAACGGGCAGTCCAGTTCATCCCGCTCCTGGCTGGA

CTGGGGATCACCGCTGCTTTCACTACCGGAGCCACTGGCTTGGGTGTCTCCGTGA

CCCAGTACACGAAGCTGTCCCACCAACTGATTTCGGACGTCCAAGTCCTATCGGGA

ACCATCCAGGACCTCCAGGATCAGGTCGATTCCCTCGCAGAGGTGGTGCTCCAGA

ACCGCAGAGGACTGGATCTGCTGACCGCTGAACAGGGAGGCATCTGCCTTGCACT

CCAGGAGAAGTGCTGCTTCTACGCCAATAAGTCGGGGATCGTGCGGAACAAAATC

AGAACTCTGCAGGAAGAACTGCAGAAGCGCCGGGAAAGCCTCGCCAGCAATCCGC

TGTGGACCGGACTCCAAGGATTTCTCCCGTATCTTCTCCCGCTGCTGGGGCCTCTG

CTCACTCTGCTGCTGATCCTGACCATCGGACCGTGCGTCTTTAGCAGACTGATGGC

ATTTATCAACGACAGACTGAACGTGGTGCATGCAATGGTCCTGGCACAGCAGTACC

AGGCCCTGAAGGCCGAGGAGGAAGCACAGGACTAG

-continued (RD114 ENV protein codon-optimised variant)
SEQ ID NO: 6
ATGAAGCTGCCCACCGGCATGGTGATCCTGTGCAGCCTGATCATCGTGCGCCCG

GCTTCGACGACCCCCGCAAGGCCATCGCCCTGGTGCAGAAGCAGCACGGCAAGC

CCTGCGAGTGCAGCGGCGGCCAGGTGAGCGAGGCCCCCCCCAACAGCATCCAGC

AGGTGACCTGCCCCGGCAAGACCGCCTACCTGATGACCAACCAGAAGTGGAAGTG

CCGCGTGACCCCCAAGAACCTGACCCCCAGCGGCGGCGAGCTGCAGAACTGCCC

CTGCAACACCTTCCAGGACAGCATGCACAGCAGCTGCTACACCGAGTACCGCCAG

TGCCGCGCCAACAACAAGACCTACTACACCGCCACCCTGCTGAAGATCCGCAGCG

GCAGCCTGAACGAGGTGCAGATCCTGCAGAACCCCAACCAGCTGCTGCAGAGCCC

CTGCCGCGGCAGCATCAACCAGCCCGTGTGCTGGAGCGCCACCGCCCCCATCCA

CATCAGCGACGGCGGCGGCCCCCTGGACACCAAGCGCGTGTGGACCGTGCAGAA

GCGCCTGGAGCAGATCCACAAGGCCATGCACCCCGAGCTGCAGTACCACCCCCTG

GCCCTGCCCAAGGTGCGCGACGACCTGAGCCTGGACGCCCGCACCTTCGACATC

CTGAACACCACCTTCCGCCTGCTGCAGATGAGCAACTTCAGCCTGGCCCAGGACT

GCTGGCTGTGCCTGAAGCTGGGCACCCCCACCCCCCTGGCCATCCCCACCCCCA

GCCTGACCTACAGCCTGGCCGACAGCCTGGCCAACGCCAGCTGCCAGATCATCCC

CCCCCTGCTGGTGCAGCCCATGCAGTTCAGCAACAGCAGCTGCCTGAGCAGCCCC

TTCATCAACGACACCGAGCAGATCGACCTGGGCGCCGTGACCTTCACCAACTGCA

CCAGCGTGGCCAACGTGAGCAGCCCCTGTGCGCCCTGAACGGCAGCGTGTTCCT

GTGCGGCAACAACATGGCCTACACCTACCTGCCCCAGAACTGGACCGGCCTGTGC

GTGCAGGCCAGCCTGCTGCCCGACATCGACATCATCCCCGGCGACGAGCCCGTG

CCCATCCCCGCCATCGACCACTACATCCACCGCCCCAAGCGCGCCGTGCAGTTCA

TCCCCCTGCTGGCCGGCCTGGGCATCACCGCCGCCTTCACCACCGGCGCCACCG

GCCTGGGCGTGAGCGTGACCCAGTACACCAAGCTGAGCCACCAGCTGATCAGCGA

CGTGCAGGTGCTGAGCGGCACCATCCAGGACCTGCAGGACCAGGTGGACAGCCT

GGCCGAGGTGGTGCTGCAGAACCGCCGCGGCCTGGACCTGCTGACCGCCGAGCA

GGGCGGCATCTGCCTGGCCCTGCAGGAGAAGTGCTGCTTCTACGCCAACAAGAGC

GGCATCGTGCGCAACAAGATCCGCACCCTGCAGGAGGAGCTGCAGAAGCGCCGC

GAGAGCCTGGCCAGCAACCCCCTGTGGACCGGCCTGCAGGGCTTCCTGCCCTAC

CTGCTGCCCCTGCTGGGCCCCCTGCTGACCCTGCTGCTGATCCTGACCATCGGCC

CCTGCGTGTTCAGCCGCCTGATGGCCTTCATCAACGACCGCCTGAACGTGGTGCA

CGCCATGGTGCTGGCCCAGCAGTACCAGGCCCTGAAGGCCGAGGAGGAGGCCCA

GGACTAA (RD114 ENV protein codon-optimised variant)
SEQ ID NO: 7
ATGAAACTTCCTACGGGCATGGTCATTCTGTGTAGTTTGATAATAGTCCGGGCCGG

GTTTGATGATCCTAGGAAGGCCATCGCATTGGTTCAGAAACAGCACGGGAAGCCCT

GTGAGTGCAGTGGTGGGCAAGTTAGTGAAGCCCCGCCTAACAGCATTCAGCAAGT

CACTTGTCCGGGTAAAACTGCATACCTGATGACTAACCAGAAATGGAAATGTAGAG

TTACTCCTAAAAATTTGACACCTTCAGGCGGAGAGCTCCAAAACTGCCCTTGTAATA

CTTTTCAGGACTCTATGCATAGCTCCTGTTACACAGAGTACAGGCAATGCAGAGCG

AATAACAAGACTTACTATACTGCGACCCTTCTGAAGATCCGGTCAGGCTCACTCAAC

```
GAAGTGCAAATTCTGCAGAACCCAAACCAACTGCTCCAAAGTCCATGTCGGGGCAG

TATCAATCAACCAGTATGCTGGTCAGCCACGGCACCTATTCACATATCTGATGGCG

GCGGACCCTTGGACACAAAGCGAGTCTGGACCGTTCAAAAGCGACTTGAGCAAAT

ACACAAAGCCATGCATCCTGAACTCCAGTATCACCCCTTGGCATTGCCAAAAGTAC

GGGACGATCTCAGTCTTGATGCAAGGACCTTTGACATACTTAACACTACATTCAGAC

TGCTCCAGATGAGTAATTTCAGCCTCGCACAGGACTGTTGGCTTTGTCTCAAGCTG

GGCACCCCCACCCCGCTCGCGATCCCGACACCGAGTCTGACATACTCACTCGCCG

ACTCATTGGCAAATGCAAGTTGCCAGATAATCCCGCCCTTGCTCGTCCAGCCGATG

CAGTTCAGTAACTCATCCTGTCTCTCAAGTCCGTTCATTAACGACACAGAACAAATC

GACTTGGGCGCAGTCACCTTCACCAACTGCACAAGTGTGGCAAATGTCAGTAGCCC

ACTTTGCGCCCTGAACGGGAGCGTATTTCTCTGTGGAAATAATATGGCGTACACGT

ATTTGCCGCAAAACTGGACCGGCCTTTGTGTTCAAGCCTCACTCCTGCCGGATATC

GACATAATCCCTGGCGACGAACCTGTACCAATCCCCGCAATCGACCACTACATTCA

CAGACCAAAGAGAGCAGTCCAGTTTATCCCCCTTCTTGCGGGCCTTGGTATCACTG

CTGCATTCACTACGGGCGCAACGGGGCTTGGGGTATCTGTAACACAATATACAAAG

CTTTCTCATCAGCTCATTTCTGACGTACAGGTGCTTTCTGGAACTATCCAAGATTTG

CAAGATCAAGTAGATTCCCTCGCAGAAGTGGTCCTCCAGAACCGGAGGGGTCTCG

ATCTTCTGACTGCCGAACAAGGGGTATCTGCCTTGCACTCCAAGAGAAATGCTGC

TTTTACGCAAACAAAAGTGGTATTGTACGCAACAAGATACGCACGCTGCAAGAGGA

GCTTCAGAAGCGACGGGAGAGCTTGGCTAGTAACCCCCTTTGGACCGGACTTCAA

GGTTTCTTGCCCTACCTTCTTCCTCTTTTGGGCCCACTCCTGACTTTGTTGCTGATT

CTCACAATAGGTCCCTGTGTTTTCTCTCGCCTTATGGCTTTCATCAACGACAGGTTG

AATGTCGTGCATGCTATGGTTTTGGCACAGCAATACCAAGCCCTTAAAGCAGAAGA

GGAAGCACAGGACTGA (Wild type RD114 ENV protein)
                                                           SEQ ID NO: 8
ATGAAACTCCCAACAGGAATGGTCATTTTATGTAGCCTAATAATAGTTCGGGCAGG

GTTTGACGACCCCCGCAAGGCTATCGCATTAGTACAAAAACAACATGGTAAACCAT

GCGAATGCAGCGGAGGGCAGGTATCCGAGGCCCCACCGAACTCCATCCAACAGGT

AACTTGCCCAGGCAAGACGGCCTACTTAATGACCAACCAAAAATGGAAATGCAGAG

TCACTCCAAAAAATCTCACCCCTAGCGGGGAGAACTCCAGAACTGCCCCTGTAAC

ACTTTCCAGGACTCGATGCACAGTTCTTGTTATACTGAATACCGGCAATGCAGGGC

GAATAATAAGACATACTACACGGCCACCTTGCTTAAAATACGGTCTGGGAGCCTCA

ACGAGGTACAGATATTACAAAACCCCAATCAGCTCCTACAGTCCCCTTGTAGGGGC

TCTATAAATCAGCCCGTTTGCTGGAGTGCCACAGCCCCCATCCATATCTCCGATGG

TGGAGGACCCCTCGATACTAAGAGAGTGTGGACAGTCCAAAAAAGGCTAGAACAAA

TTCATAAGGCTATGCATCCTGAACTTCAATACCACCCCTTAGCCCTGCCCAAAGTCA

GAGATGACCTTAGCCTTGATGCACGGACTTTTGATATCCTGAATACCACTTTTAGGT

TACTCCAGATGTCCAATTTTAGCCTTGCCCAAGATTGTTGGCTCTGTTTAAAACTAG

GTACCCCTACCCCTCTTGCGATACCCACTCCCTCTTTAACCTACTCCCTAGCAGACT

CCCTAGCGAATGCCTCCTGTCAGATTATACCTCCCCTCTTGGTTCAACCGATGCAG
```

-continued

```
TTCTCCAACTCGTCCTGTTTATCTTCCCCTTTCATTAACGATACGGAACAAATAGACT

TAGGTGCAGTCACCTTTACTAACTGCACCTCTGTAGCCAATGTCAGTAGTCCTTTAT

GTGCCCTAAACGGGTCAGTCTTCCTCTGTGGAAATAACATGGCATACACCTATTTAC

CCCAAAACTGGACAGGACTTTGCGTCCAAGCCTCCCTCCTCCCCGACATTGACATC

ATCCCGGGGATGAGCCAGTCCCCATTCCTGCCATTGATCATTATATACATAGACC

TAAACGAGCTGTACAGTTCATCCCTTTACTAGCTGGACTGGGAATCACCGCAGCAT

TCACCACCGGAGCTACAGGCCTAGGTGTCTCCGTCACCCAGTATACAAAATTATCC

CATCAGTTAATATCTGATGTCCAAGTCTTATCCGGTACCATACAAGATTTACAAGAC

CAGGTAGACTCGTTAGCTGAAGTAGTTCTCCAAAATAGGAGGGGACTGGACCTACT

AACGGCAGAACAAGGAGGAATTTGTTTAGCCTTACAAGAAAAATGCTGTTTTTATGC

TAACAAGTCAGGAATTGTGAGAAACAAAATAAGAACCCTACAAGAAGAATTACAAAA

ACGCAGGGAAAGCCTGGCATCCAACCCTCTCTGGACCGGGCTGCAGGGCTTTCTT

CCGTACCTCCTACCTCTCCTGGGACCCCTACTCACCCTCCTACTCATACTAACCATT

GGGCCATGCGTTTTCAGTCGCCTCATGGCCTTCATTAATGATAGACTTAATGTTGTA

CATGCCATGGTGCTGGCCCAGCAATACCAAGCACTCAAAGCTGAGGAAGAAGCTC

AGGATTGA (GALV ENV protein codon-optimised variant)
                                                    SEQ ID NO: 9
ATGGTGTTGCTTCCTGGGTCTATGCTGCTGACATCTAATCTCCACCATCTCAGACAC

CAGATGTCACCCGGCAGTTGGAAGCGGCTGATCATACTGTTGAGCTGCGTATTCG

GCGGAGGGGGCACCTCTCTCCAGAACAAAAATCCTCATCAACCGATGACGCTTAC

GTGGCAGGTATTGTCCCAGACGGGTGACGTGGTATGGGACACTAAGGCTGTTCAA

CCGCCTTGGACGTGGTGGCCGACGCTGAAGCCAGATGTCTGTGCCCTGGCGGCG

TCCCTTGAGAGCTGGGATATCCCGGGGACCGACGTATCCTCCAGCAAGAGAGTTC

GCCCCCCTGACTCAGACTACACAGCCGCCTATAAGCAAATCACTTGGGGCGCGATT

GGGTGTTCATATCCCCGAGCACGCACCAGAATGGCAAGCTCTACATTCTATGTTTG

TCCCCGCGATGGCCGGACGCTGTCCGAAGCGAGGCGATGCGGAGGTCTCGAAAG

CCTCTACTGCAAGGAATGGGACTGTGAGACTACGGGCACGGGTTATTGGCTTTCTA

AATCAAGCAAAGACTTGATCACTCTTAAGTGGGACCAGAACTCAGAGTGGACACAA

AAGTTTCAACAATGCCACCAGACTGGATGGTGCAACCCCTTGAAGATAGACTTTACT

GACAAAGGTAAGCTGAGCAAGGACTGGATAACAGGGAAAACTTGGGGGTTGCGCT

TTTATGTCTCAGGCCATCCGGGGGTACAATTTACGATTCGCCTCAAAATCACGAACA

TGCCGGCGGTCGCTGTAGGTCCGGACTTGGTTTTGGTAGAACAAGGCCCTCCTCG

GACTAGCCTCGCACTGCCTCCCCCACTCCCGCCTCGAGAGGCACCACCGCCGAGC

CTGCCGGATTCCAATTCAACGGCTCTGGCCACCTCCGCACAAACACCAACAGTGC

GGAAGACTATCGTGACCCTCAACACTCCGCCCCCGACCACGGGCGACAGATTGTT

TGACCTGGTTCAAGGGGCCTTCTTGACGCTCAATGCAACGAACCCTGGAGCAACA

GAGTCTTGTTGGCTTTGTCTGGCCATGGGTCCCCCTTATTATGAAGCCATCGCGTC

ATCTGGTGAAGTGGCTTACTCAACCGACCTCGATCGCTGTAGGTGGGGCACGCAA

GGAAAGCTTACTTTGACCGAGGTCTCAGGTCATGGGTTGTGCATTGGGAAGGTCCC

CTTTACACACCAACATCTTTGTAACCAGACTCTGAGTATAAATTCTTCTGGAGATCAT

CAGTATTTGCTGCCGAGTAACCATTCATGGTGGGCGTGCTCCACGGGACTCACCC
```

-continued

CTTGCCTTTCAACTTCCGTTTTTAATCAAACGAGAGATTTCTGTATCCAAGTGCAACT

CATTCCGAGGATCTACTACTATCCGGAAGAAGTACTCCTGCAGGCGTATGACAATT

CCCACCCTAGGACCAAACGCGAAGCAGTGAGCCTGACCCTTGCAGTATTGTTGGG

TTTGGGATTACTGCGGGTATCGGCACTGGTTCCACCGCGCTGATTAAGGGACCG

ATCGATTTGCAACAAGGATTGACTTCACTCCAGATAGCCATAGACGCCGACCTTCG

CGCGTTGCAGGATTCTGTGTCTAAGCTGGAGGATAGTTTGACAAGCCTCTCAGAGG

TGGTGCTGCAAAACAGACGAGGCCTTGATCTCTTGTTTCTTAAGGAGGGAGGCCTT

TGCGCTGCTCTGAAGGAAGAGTGTTGTTTCTACATCGATCATAGCGGAGCGGTCAG

AGATTCTATGAAGAAGCTTAAGGAGAAGCTTGACAAGCGACAGCTCGAACGCCAAA

AGAGCCAGAATTGGTACGAAGGATGGTTTAATAATTCTCCATGGTTCACTACACTGC

TTTCCACCATCGCTGGTCCGCTGCTGCTCCTGCTGCTCCTGTTGATACTCGGTCCG

TGCATAATTAATAAGCTCGTTCAATTCATAAACGACCGGATCTCTGCGTGCTAA (GALV ENV protein codon-optimised variant)

SEQ ID NO: 10

ATGGTGCTTCTCCCTGGTAGCATGCTTTTGACCTCAAACCTCCATCATCTGCGACAC

CAGATGTCACCTGGCTCTTGGAAACGCCTTATTATATTGCTGAGCTGTGTTTTTGGA

GGCGGAGGTACATCATTGCAGAACAAAAACCCTCATCAGCCAATGACGTTGACCTG

GCAAGTATTGTCCCAGACCGGAGATGTCGTTTGGGACACGAAAGCGGTACAACCT

CCCTGGACTTGGTGGCCGACCCTCAAGCCCGACGTTTGCGCTCTTGCGGCGTCTT

TGGAGTCTTGGACATACCGGGGACGGATGTCTCATCTTCAAAGAGGGTTCGACC

GCCGGATTCAGACTACACCGCTGCATATAAGCAGATTACGTGGGGAGCCATTGGCT

GTAGTTATCCGCGGGCGAGGACGCGGATGGCTTCCAGTACTTTTTATGTGTGTCCG

AGAGACGGCCGCACCCTGTCTGAGGCTCGGCGCTGCGGGGGGCTCGAAAGCCTG

TACTGCAAAGAATGGGATTGTGAGACTACAGGGACTGGTTATTGGCTCTCAAAATC

TAGCAAAGATCTGATTACGCTCAAATGGGATCAAAATTCAGAATGGACCCAAAAGTT

CCAGCAATGTCATCAGACCGGGTGGTGTAATCCGCTGAAGATAGACTTTACAGACA

AAGGCAAACTGTCAAAAGACTGGATTACGGGTAAGACTTGGGGCCTCCGCTTTTAC

GTAAGCGGTCATCCTGGGGTACAGTTTACTATAAGGCTGAAAATAACGAACATGCC

GGCGGTCGCTGTCGGGCCGGATTTGGTGCTCGTGGAACAAGGGCCACCTAGGAC

CTCTCTCGCTCTTCCCCCGCCATTGCCACCACGGGAAGCACCGCCACCAAGTCTTC

CAGATTCCAACTCTACCGCACTGGCTACGAGTGCGCAGACACCAACGGTTAGAAAA

ACCATTGTCACGCTTAACACCCCCCCTCCGACAACCGGAGATCGCCTTTTCGATCT

CGTACAGGGCGCGTTTCTTACGCTTAACGCCACAAATCCTGGGGCCACTGAGAGC

TGTTGGCTTTGCCTTGCTATGGGCCCACCATACTATGAGGCCATCGCCTCCTCCGG

CGAAGTAGCCTACTCCACGGACCTTGACCGATGCAGGTGGGGAACGCAAGGCAAA

TTGACTTTGACTGAGGTGAGCGGGCATGGTCTCTGCATCGGAAAAGTTCCGTTCAC

TCATCAGCACCTTTGTAACCAGACCCTCAGCATTAATTCTTCCGGGGATCATCAGTA

CCTCCTGCCGTCAAACCACTCTTGGTGGGCCTGCTCCACAGGTCTTACTCCCTGCT

TGAGCACATCCGTATTTAATCAGACCCGAGACTTCTGTATCCAGGTACAATTGATAC

CGAGAATTTATTACTACCCCGAGGAAGTGTTGCTCCAAGCATACGATAACTCACAC

CCTAGAACGAAGAGAGAAGCAGTCTCCCTGACGTTGGCCGTCCTTCTGGGACTGG

-continued
GAATCACCGCGGGTATAGGCACTGGATCTACGGCACTGATCAAGGGGCCTATAGA

TTTGCAGCAGGGGCTTACTTCACTTCAAATTGCCATAGACGCGGATCTTCGGGCGC

TCCAGGACTCCGTTTCCAAGTTGGAAGACTCTCTGACTAGCCTGTCCGAAGTTGTG

TTGCAGAACAGACGAGGACTTGACTTGTTGTTTCTCAAGGAAGGGGGTCTCTGTGC

TGCGCTTAAGGAGGAATGTTGCTTCTATATAGATCATTCCGGCGCGGTACGGGACT

CCATGAAAAAACTTAAAGAAAAGTTGGACAAGAGACAGTTGGAGAGGCAAAAGTCC

CAGAACTGGTATGAGGGCTGGTTTAATAACTCCCCATGGTTTACAACCCTTTTGTCT

ACCATTGCTGGGCCGCTCCTTCTTCTTCTGTTGCTGCTCATATTGGGGCCTTGTATT

ATTAACAAGCTTGTGCAATTCATTAATGACCGAATTTCTGCATGCTAA

SEQ ID NO: 11: (GALV ENV protein codon-optimised variant)
ATGGTGCTGCTGCCCGGCAGCATGCTGCTGACCAGCAACCTGCACCACCTGCGCC

ACCAGATGAGCCCCGGCAGCTGGAAGCGCCTGATCATCCTGCTGAGCTGCGTGTT

CGGCGGCGGCGGCACCAGCCTGCAGAACAAGAACCCCCACCAGCCCATGACCCT

GACCTGGCAGGTGCTGAGCCAGACCGGCGACGTGGTGTGGGACACCAAGGCCGT

GCAGCCCCCTGGACCTGGTGGCCCACCCTGAAGCCCGACGTGTGCGCCCTGGC

CGCCAGCCTGGAGAGCTGGGACATCCCCGGCACCGACGTGAGCAGCAGCAAGCG

CGTGCGCCCCCCCGACAGCGACTACACCGCCGCCTACAAGCAGATCACCTGGGG

CGCCATCGGCTGCAGCTACCCCCGCGCCCGCACCCGCATGGCCAGCAGCACCTT

CTACGTGTGCCCCCGCGACGGCCGCACCCTGAGCGAGGCCCGCCGCTGCGGCG

GCCTGGAGAGCCTGTACTGCAAGGAGTGGGACTGCGAGACCACCGGCACCGGCT

ACTGGCTGAGCAAGAGCAGCAAGGACCTGATCACCCTGAAGTGGGACCAGAACAG

CGAGTGGACCCAGAAGTTCCAGCAGTGCCACCAGACCGGCTGGTGCAACCCCCTG

AAGATCGACTTCACCGACAAGGGCAAGCTGAGCAAGGACTGGATCACCGGCAAGA

CCTGGGGCCTGCGCTTCTACGTGAGCGGCCACCCCGGCGTGCAGTTCACCATCCG

CCTGAAGATCACCAACATGCCCGCCGTGGCCGTGGGCCCCGACCTGGTGCTGGT

GGAGCAGGGCCCCCCCCGCACCAGCCTGGCCCTGCCCCCCCCCCTGCCCCCCCG

CGAGGCCCCCCCCCCCAGCCTGCCCGACAGCAACAGCACCGCCCTGGCCACCAG

CGCCCAGACCCCCACCGTGCGCAAGACCATCGTGACCCTGAACACCCCCCCCCCC

ACCACCGGCGACCGCCTGTTCGACCTGGTGCAGGGCGCCTTCCTGACCCTGAACG

CCACCAACCCCGGCGCCACCGAGAGCTGCTGGCTGTGCCTGGCCATGGGCCCCC

CCTACTACGAGGCCATCGCCAGCAGCGGCGAGGTGGCCTACAGCACCGACCTGG

ACCGCTGCCGCTGGGGCACCCAGGGCAAGCTGACCCTGACCGAGGTGAGCGGCC

ACGGCCTGTGCATCGGCAAGGTGCCCTTCACCCACCAGCACCTGTGCAACCAGAC

CCTGAGCATCAACAGCAGCGGCGACCACCAGTACCTGCTGCCCAGCAACCACAGC

TGGTGGGCCTGCAGCACCGGCCTGACCCCCTGCCTGAGCACCAGCGTGTTCAACC

AGACCCGCGACTTCTGCATCCAGGTGCAGCTGATCCCCCGCATCTACTACTACCCC

GAGGAGGTGCTGCTGCAGGCCTACGACAACAGCCACCCCCGCACCAAGCGCGAG

GCCGTGAGCCTGACCCTGGCCGTGCTGCTGGGCCTGGGCATCACCGCCGGCATC

GGCACCGGCAGCACCGCCCTGATCAAGGGCCCCATCGACCTGCAGCAGGGCCTG

ACCAGCCTGCAGATCGCCATCGACGCCGACCTGCGCGCCCTGCAGGACAGCGTG

AGCAAGCTGGAGGACAGCCTGACCAGCCTGAGCGAGGTGGTGCTGCAGAACCGC

-continued

CGCGGCCTGGACCTGCTGTTCCTGAAGGAGGGCGGCCTGTGCGCCGCCCTGAAG

GAGGAGTGCTGCTTCTACATCGACCACAGCGGCGCCGTGCGCGACAGCATGAAGA

AGCTGAAGGAGAAGCTGGACAAGCGCCAGCTGGAGCGCCAGAAGAGCCAGAACT

GGTACGAGGGCTGGTTCAACAACAGCCCCTGGTTCACCACCCTGCTGAGCACCAT

CGCCGGCCCCCTGCTGCTGCTGCTGCTGCTGCTGATCCTGGGCCCCTGCATCATC

AACAAGCTGGTGCAGTTCATCAACGACCGCATCAGCGCCTGCTAA (Wild type GALV ENV protein)

SEQ ID NO: 12

ATGGTATTGCTGCCTGGGTCCATGCTTCTCACCTCAAACCTGCACCACCTTCGGCA

CCAGATGAGTCCTGGGAGCTGGAAAAGACTGATCATCCTCCTAAGCTGCGTATTCG

GCGGCGGCGGTACCAGTCTGCAAAATAAGAACCCCCACCAGCCCATGACCCTCAC

TTGGCAGGTACTGTCCCAAACTGGAGACGTTGTCTGGGATACAAAGGCAGTCCAG

CCCCCTTGGACTTGGTGGCCCACACTTAAACCTGATGTATGTGCCTTGGCGGCTAG

TCTTGAGTCCTGGGATATCCCGGGAACCGATGTCTCGTCCTCTAAACGAGTCAGAC

CTCCGGACTCAGACTATACTGCCGCTTATAAGCAAATCACCTGGGGAGCCATAGGG

TGCAGCTACCCTCGGGCTAGGACTAGAATGGCAAGCTCTACCTTCTACGTATGTCC

CCGGGATGGCCGGACCCTTTCAGAAGCTAGAAGGTGCGGGGGGCTAGAATCCCTA

TACTGTAAAGAATGGGATTGTGAGACCACGGGGACCGGTTATTGGCTATCTAAATC

CTCAAAAGACCTCATAACTCTTAAGTGGGACCAAAATAGCGAATGGACTCAAAAATT

TCAACAGTGTCACCAGACCGGCTGGTGTAACCCCCTTAAAATAGATTTCACAGACA

AAGGAAAATTATCCAAGGACTGGATAACGGGAAAAACCTGGGGATTAAGATTCTAT

GTGTCTGGACATCCAGGCGTACAGTTCACCATTCGCTTAAAAATCACCAACATGCC

AGCTGTGGCAGTAGGTCCTGACCTCGTCCTTGTGGAACAAGGACCTCCTAGAACGT

CCCTCGCTCTCCCACCTCCTCTTCCCCCAAGGGAAGCGCCACCGCCATCTCTCCC

CGACTCTAACTCCACAGCCCTGGCGACTAGTGCACAAACTCCCACGGTGAGAAAAA

CAATTGTTACCCTAAACACTCCGCCTCCCACCACAGGCGACAGACTTTTTGATCTTG

TGCAGGGGGCCTTCCTAACCTTAAATGCTACCAACCCAGGGGCCACTGAGTCTTGC

TGGCTTTGTTTGGCCATGGGCCCCCCTTATTATGAAGCAATAGCCTCATCAGGAGA

GGTCGCCTACTCCACCGACCTTGACCGGTGCCGCTGGGGGACCCAAGGAAAGCTC

ACCCTCACTGAGGTCTCAGGACACGGGTTGTGCATAGGAAAGGTGCCCTTTACCCA

TCAGCATCTCTGCAATCAGACCCTATCCATCAATTCCTCCGGAGACCATCAGTATCT

GCTCCCCTCCAACCATAGCTGGTGGGCTTGCAGCACTGGCCTCACCCCTTGCCTC

TCCACCTCAGTTTTTAATCAGACTAGAGATTTCTGTATCCAGGTCCAGCTGATTCCT

CGCATCTATTACTATCCTGAAGAAGTTCGTTACAGGCCTATGACAATTCTCACCCC

AGGACTAAAAGAGAGGCTGTCTCACTTACCCTAGCTGTTTTACTGGGGTTGGGAAT

CACGGCGGGAATAGGTACTGGTTCAACTGCCTTAATTAAAGGACCTATAGACCTCC

AGCAAGGCCTGACAAGCCTCCAGATCGCCATAGATGCTGACCTCCGGGCCCTCCA

AGACTCAGTCAGCAAGTTAGAGGACTCACTGACTTCCCTGTCCGAGGTAGTGCTCC

AAAATAGGAGAGGCCTTGACTTGCTGTTTCTAAAAGAAGGTGGCCTCTGTGCGGCC cTAAAGGAAGAGTGCTGTTTTTACATAGACCACTCAGGTGCAGTACGGGACTCCAT

GAAAAAACTCAAAGAAAAACTGGATAAAAGACAGTTAGAGCGCCAGAAAAGCCAAA

ACTGGTATGAAGGATGGTTCAATAACTCCCCTTGGTTCACTACCCTGCTATCAACCA

-continued

TCGCTGGGCCCCTATTACTCCTCCTTCTGTTGCTCATCCTCGGGCCATGCATCATC

AATAAGTTAGTTCAATTCATCAATGATAGGATAAGTGCATGTTAA (Gag Polyprotein Amino Acid Sequence)
SEQ ID NO: 13
MGQTVTTPLSLTLGHWKDVERIAHNQSVDVKKRRWVTFCSAEWPTFNVGWPRDGTF

NRDLITQVKIKVFSPGPHGHPDQVPYIVTWEALAFDPPPWVKPFVHPKPPPLPPSAPS

LPLEPPRSTPPRSSLYPALTPSLGAKPKPQVLSDSGGPLIDLLTEDPPPYRDPRPPPSD

RDGNGGEATPAGEAPDPSPMASRLRGRREPPVADSTTSQAFPLRAGGNGQLQYWPF

SSSDLYNWKNNNPSFSEDPGKLTALIESVLITHQPTWDDCQQLLGTLLTGEEKQRVLLE

ARKAVRGDDGRPTQLPNEVDAAFPLERPDWDYTTQAGRNHLVHYRQLLLAGLQNAGR

SPTNLAKVKGITQGPNESPSAFLERLKEAYRRYTPYDPEDPGQETNVSMSFIWQSAPDI

GRKLERLEDLKNKTLGDLVREAEKIFNKRETPEEREERIRRETEEKEERRRTEDEQKEK

ERDRRRHREMSKLLATVVSGQKQDRQGGERRRSQLDRDQCAYCKEKGHWAKDCPK

KPRGPRGPRPQTSLLTLDD*

(Pol Polyprotein Amino Acid Sequence)
SEQ ID NO: 14
MGPMGQPLQVLTLNIEDEYRLHETSKEPDVSLGSTWLSDFPQAWAETGGMGLAVRQA

PLHPLKATSTPVSIKQYPMSQEARLGIKPHIQRLLDQGILVPCQSPWNTPLLPVKKPGTN

DYRPVQDLREVNKRVEDIHPTVPNPYNLLSGLPPSHQWYTVLDLKDAFFCLRLHPTSQ

PLFAFEWRDPEMGISGQLTWTRLPQGFKNSPTLFDEALHRDLADFRIQHPDLILLQYVD

DLLLAATSELDCQQGTRALLQTLGNLGYRASAKKAQICQKQVKYLGYLLKEGQRWLTE

ARKETVMGQPTPKTPRQLREFLGTAGFCRLWIPGFAEMAAPLYPLTKTGTLFNWGPD

QQKAYQEIKQALLTAPALGLPDLTKPFELFVDEKQGYAKGVLTQKLGPWRRPVAYLSK

KLDPVAAGWPPCLRMVAAIAVLTKDAGKLTMGQPLVILAPHAVEALVKQPPDRWLSNA

RMTHYQALLLDTDRVQFGPVVALNPATLLPLPEEGLQHDCLDILAEAHGTRSDLTDQPL

PDADHTWYTDGSSFLQEGQRKAGAAVTTETEVIWARALPAGTSAQRAELIALTQALKM

AEGKKLNVYTDSRYAFATAHIHGEIYRRRGLLTSEGKEIKNKDEILALLKALFLPKRLSIIH

CPGHQKGNSAEARGNRMADQAAREVATRETPGTSTLLIENSTPYTHEHFHYTVTDTKD

LTKLGATYDSAKKYWVYQGKPVMPDQFTFELLDFLHQLTHLSFSKTKALLERSPSPYY

MLNRDRTLKNITETCKACAQVNASKSAVKQGTRVRGHRPGTHWEIDFTEVKPGLYGYK

YLLVFVDTFSGWIEAFPTKKETAKVVTKKLLEEIFPRFGMPQVLGTDNGPAFVSKVSQT

VADLLGIDWKLHCAYRPQSSGQVERMNRTIKETLTKLTLATGSRDWVLLLPLALYRARN

TPGPHGLTPYEILYGAPPPLVNFPDPDMTRVTNSPSLQAHLQALYLVQHEVWRPLAAA

YQEQLDRPVVPHPYRVGDTVWVRRHQTKNLEPRWKGPYTVLLTTPTALKVDGIAAWIH

AAHVKAADTESGPSSGRTWRVQRSQNPLKIRLTRGSP*

SEQ ID NO: 15: RD114 Envelope Amino Acid Sequence
MKLPTGMVILCSLIIVRAGFDDPRKAIAIVQKQHGKPCECSGGQVSEAPPNSIQQVTCP

GKTAYLMTNQKWKCRVTPKNLTPSGGELQNCPCNTFQDSMHSSCYTEYRQCRANNK

TYYTATLLKIRSGSLNEVQILQNPNQLLQSPCRGSINQPVCWSATAPIHISDGGGPLDTK

RVWTVQKRLEQIHKAMHPELQYHPLALPKVRDDLSLDARTFDILNTTFRLLQMSNFSLA

QDCWLCLKLGTPTPLAIPTPSLTYSLADSLANASCQIIPPLLVQPMQFSNSSCLSSPFIND

TEQIDLGAVTFTNCTSVANVSSPLCALNGSVFLCGNNMAYTYLPQNWTGLCVQASLLP

DIDHPGDEPVPIPAIDHYIHRPKRAVQFIPLLAGLGITAAFTTGATGLGVSVTQYTKLSHQ

-continued

LISDVQVLSGTIQDLQDQVDSLAEVVLQNRRGLDLLTAEQGGICLALQEKCCFYANKSGI

VRNKIRTLQEELQKRRESLASNPLWTGLQGFLPYLLPLLGPLLTLLLILTIGPCVFSRLMA

FINDRLNWHAMVLAQQYQALKAEEEAQD*

(Galv Envelope Amino Acid Sequence)
SEQ ID NO: 16

MVLLPGSMLLTSNLHHLRHQMSPGSWKRLIILLSCVFGGGGTSLQNKNPHQPMTLTW

QVLSQTGDVVWDTKAVQPPWTWWPTLKPDVCALAASLESWDIPGTDVSSSKRVRPP

DSDYTAAYKQITWGAIGCSYPRARTRMASSTFYVCPRDGRTLSEARRCGGLESLYCKE

WDCETTGTGYWLSKSSKDLITLKWDQNSEWTQKFQQCHQTGWCNPLKIDFTDKGKLS

KDWITGKTWGLRFYVSGHPGVQFTIRLKITNMPAVAVGPDLVLVEQGPPRTSLALPPPL

PPREAPPPSLPDSNSTALATSAQTPTVRKTIVTLNTPPPTTGDRLFDLVQGAFLTLNATN

PGATESCWLCLAMGPPYYEAIASSGEVAYSTDLDRCRWGTQGKLTLTEVSGHGLCIGK

VPFTHQHLCNQTLSINSSGDHQYLLPSNHSWWACSTGLTPCLSTSVFNQTRDFCIQVQ

LIPRIYYYPEEVLLQAYDNSHPRTKREAVSLTLAVLLGLGITAGIGTGSTALIKGPIDLQQG

LTSLQIAIDADLRALQDSVSKLEDSLTSLSEVVLQNRRGLDLLFLKEGGLCAALKEECCF

YIDHSGAVRDSMKKLKEKLDKRQLERQKSQNWYEGWFNNSPWFTTLLSTIAGPLLLLL

LLLILGPCIINKLVQFINDRISAC*

(Nucleotide Sequence encoding the packaging signal in the genome plasmid)
SEQ ID NO: 17

AAGCTGGCCAGCAACTTATCTGTGTCTGTCCGATTGTCTAGTGTCTATGACTGATTT

TATGCGCCTGCGTCGGTACTAGTTAGCTAACTAGCTCTGTATCTGGCGGACCCGTG

GTGGAACTGACGAGTTCGGAACACCCGGCCGCAACCCTGGGAGACGTCCCAGGG

ACTTCGGGGGCCGTTTTTGTGGCCCGACCTGAGTCCTAAAATCCCGATCGTTTAGG

ACTCTTTGGTGCACCCCCCTTAGAGGAGGGATATGTGGTTCTGGTAGGAGACGAG

AACCTAAAACAGTTCCCGCCTCCGTCTGAATTTTTGCTTTCGGTTTGGGACCGAAG

CCGCGCCGCGCGTCTTGTCTGCTGCAGCATCGTTCTGTGTTGTCTCTGTCTGACTG

TGTTTCTGTATTTGTCTGAAAATATGGGCCCGGGCTAGCCTGTTACCACTCCCTTAA

GTTTGACCTTAGGTCACTGGAAAGATGTCGAGCGGATCGCTCACAACCAGTCGGTA

GATGTCAAGAAGAGACGTTGGGTTACCTTCTGCTCTGCAGAATGGCCAACCTTTAA

CGTCGGATGGCCGCGAGACGGCACCTTTAACCGAGACCTCATCACCCAGGTTAAG

ATCAAGGTCTTTTCACCTGGCCCGCATGGACACCCAGACCAGGTCCCCTACATCGT

GACCTGGGAAGCCTTGGCTTTTGACCCCCCTCCCTGGGTCAAGCCCTTTGTACACC

CTAAGCCTCCGCCTCCTCTTCCTCCATCCGCCCCGTCTCTCCCCCTTGAACCTCCT

CGTTCGACCCCGCCTCGATCCTCCCTTTATCCAGCCCTCACTCCTTCTCTAGGCGC

CCCCATATGGCCATATGAGATCTTATATGGGGCACCCCCGCCCCTTGTAAACTTCC

CTGACCCTGACATGACAAGAGTTACTAACAGCCCCTCTCTCCAAGCTCACTTACAG

GCTCTCTACTTAGTCCAGCACGAAGTCTGGAGACCTCTGGCGGCAGCCTACCAAG

AACAACTGGACCGA (Nucleotide sequence of CMV promoter)
SEQ ID NO: 18

AGTAATCAATTACGGGGTCATTAGTTCATAGCCCATATATGGAGTTCCGCGTTACAT

AACTTACGGTAAATGGCCCGCCTGGCTGACCGCCCAACGACCCCCGCCCATTGAC

GTCAATAATGACGTATGTTCCCATAGTAACGCCAATAGGGACTTTCCATTGACGTCA

-continued

ATGGGTGGAGTATTTACGGTAAACTGCCCACTTGGCAGTACATCAAGTGTATCATAT

GCCAAGTACGCCCCCTATTGACGTCAATGACGGTAAATGGCCCGCCTGGCATTATG

CCCAGTACATGACCTTATGGGACTTTCCTACTTGGCAGTACATCTACGTATTAGTCA

TCGCTATTACCATGCTGATGCGGTTTTGGCAGTACATCAATGGGCGTGGATAGCGG

TTTGACTCACGGGGATTTCCAAGTCTCCACCCCATTGACGTCAATGGGAGTTTGTTT

TGGCACCAAAATCAACGGGACTTTCCAAAATGTCGTAACAACTCCGCCCCATTGAC

GCAAATGGGCGGTAGGCGTGTACGGTGGGAGGTCTATATAAGCAGAGCTGGTTTA

GTGAACCGTC (Nucleotide sequence of CAG promoter)

SEQ ID NO: 19

ATAGTAATCAATTACGGGGTCATTAGTTCATAGCCCATATATGGAGTTCCGCGTTAC

ATAACTTACGGTAAATGGCCCGCCTGGCTGACCGCCCAACGACCCCCGCCCATTG

ACGTCAATAATGACGTATGTTCCCATAGTAACGCCAATAGGGACTTTCCATTGACGT

CAATGGGTGGACTATTTACGGTAAACTGCCCACTTGGCAGTACATCAAGTGTATCAT

ATGCCAAGTACGCCCCCTATTGACGTCAATGACGGTAAATGGCCCGCCTGGCATTA

TGCCCAGTACATGACCTTATGGGACTTTCCTACTTGGCAGTACATCTACGTATTAGT

CATCGCTATTACCATGCTGTCGAGGTGAGCCCCACGTTCTGCTTCACTCTCCCCATC

TCCCCCCCTCCCCACCCCCAATTTTGTATTTATTTATTTTTTAATTATTTTATGCAG

CGATGGGGGCGGGGGGGGGGGGCGCGCGCCAGGCGGGGCGGGGCGGGGC

GAGGGGCGGGGCGGGGCGAGGCGGAGAGGTGCGGCGGCAGCCAATCAGAGCG

GCGCGCTCCGAAAGTTTCCTTTTATGGCGAGGCGGCGGCGGCGGCGGCCCTATAA

AAAGCGAAGCGCGCGGCGGGCGGGAGTCGCTGCGTTGCCTTCGCCCCGTGCCCC

GCTCCGCGCCGCCTCGCGCCGCCCGCCCCGGCTCTGACTGACCGCGTTACTCCC

ACAGGTGAGCGGGCGGGACGGCCCTTCTCCCTCCGGGCTGTAATTAGCGCTTGGT

TTAATGACGGCTCGTTTCTTTTCTGTGGCTGCGTGAAAGCCTTAAAGGGCTCCGGG

AGGGCCTTTGTGCGGGGGGAGCGGCTCGGGGGGTGCGTGCGTGTGTGTGC

GTGGGGAGCGCCGCGTGCGGCCCGCGCTGCCCGGCGGCTGTGAGCGCTGCGGG

CGCGGCGCGGGGCTTTGTGCGCTCCGCGTGTGCGCGAGGGGAGCGCGGGCCGG

GGGCGGTGCCCCGCGGTGCGGGGGGGCTGCGAGGGGAACAAAGGCTGCGTGCG

GGGTGTGTGCGTGGGGGGGTGAGCAGGGGGTGTGGGCGCGGCGGTCGGGCTGT

AACCCCCCCCTGGCACCCCCCTCCCCGAGTTGCTGAGCACGGCCCGGCTTCGGG

TGCGGGCTCCGTGCGGGGCGTGGCGCGGGGCTCGCCGTGCCGGGCGGGGGGT

GGCGGCAGGTGGGGGTGCCGGGCGGGGCGGGGCCGCCTCGGGCCGGGGAGGG

CTCGGGGAGGGGCGCGGCGGCCCCGGAGCGCCGGCGGCTGTCGAGGCGCGG

CGAGCCGCAGCCATTGCCTTTTATGGTAATCGTGCGAGAGGGCGCAGGGACTTCC

TTTGTCCCAAATCTGGCGGAGCCGAAATCTGGGAGGCGCCGCCGCACCCCCTCTA

GCGGGCGCGGGCGAAGCGGTGCGGCGCCGGCAGGAAGGAAATGGGCGGGGAG

GGCCTTCGTGCGTCGCCGCGCCGCCGTCCCCTTCTCCATCTCCAGCCTCGGGGCT

GCCGCAGGGGGACGGCTGCCTTCGGGGGGGACGGGGCAGGGCGGGGTTCGGCT

-continued

TCTGGCGTGTGACCGGCGGCTTTAGAGCCTCTGCTAACCATGTTCATGCCTTCTTC

TTTTTCCTACAGCTCCTGGGCAACGTGCTGGTTGTTGTGCTGTCTCATCATTTTGGC

AA (Nucleotide sequence of Rabbit B-globin polyA)
SEQ ID NO: 20
CTGGTGTGGCCAATGCCCTGGCTCACAAATACCACTGACGATCTTTTTCCCTCTGC

CAAAAATTATGGGGACATCATGAAGCCCCTTGAGCATCTGACTTCTGGCTAATAAAG

GAAATTTATTTTCATTGCAATAGTGTGTTGGAATTTTTTGTGTCTCTCACTCGG (Nucleotide sequence of BGIntron)
SEQ ID NO: 21
AGATCGCCTGGAGACGCCATCCACGCTGTTTTGACCTCCATAGAAGACACCGGGA

CCGATCCAGCCTCCCCTCGAAGCTTACATGTGGTACCGAGCTCGGATCCTGAGAA

CTTCAGGGTGAGTCTATGGGACCCTTGATGTTTTCTTTCCCCTTCTTTTCTATGGTT

AAGTTCATGTCATAGGAAGGGGAGAAGTAACAGGGTACACATATTGACCAAATCAG

GGTAATTTTGCATTTGTAATTTTAAAAAATGCTTTCTTCTTTTAATATACTTTTTGTTT

ATCTTATTTCTAATACTTTCCCTAATCTCTTTCTTTCAGGGCAATAATGATACAATGTA

TCATGCCTCTTTGCACCATTCTAAAGAATAACAGTGATAATTTCTGGGTTAAGGCAA

TAGCAATATTTCTGCATATAAATATTTCTGCATATAAATTGTAACTGATGTAAGAGGT

TTCATATTGCTAATAGCAGCTACAATCCAGCTACCATTCTGCTTTTATTTTATGGTTG

GGATAAGGCTGGATTATTCTGAGTCCAAGCTAGGCCCTTTTGCTAATCATGTTCATA

CCTCTTATCTTCCTCCCACAGCTCCTGGGCAACGTGCTGGTCTGTGTGCTGGCCCA

TCACTTTGGCAAAG (Nucleotide sequence of Ferritin promoter)
SEQ ID NO: 22
AGTAATCAATTACGGGGTCATTAGTTCATAGCCCATATATGGAGTTCCGCGTTACAT

AACTTACGGTAAATGGCCCGCCTGGCTGACCGCCCAACGACCCCCGCCCATTGAC

GTCAATAATGACGTATGTTCCCATAGTAACGCCAATAGGGACTTTCCATTGACGTCA

ATGGGTGGAGTATTTACGGTAAACTGCCCACTTGGCAGTACATCAAGTGTATCATAT

GCCAAGTACGCCCCCTATTGACGTCAATGACGGTAAATGGCCCGCCTGGCATTATG

CCCAGTACATGACCTTATGGGACTTTCCTACTTGGCAGTACATCTACGTATTAGTCA

TCGCTATTACCATGCTGATGCGGTTTTGGCAGTACATCAATGGGCGTGGATAGCGG

TTTGACTCACGGGGATTTCCAAGTCTCCACCCCATTGACGTCAATGGGAGTTTGTTT

TGGCACCAAAATCAACGGGACTTTCCAAAATGTCGTAACAACTCCGCCCCATTGAC

GCAAATGGGCGGTAGGCGTGTACGGTGGGAGGTCTATATAAGCAGAGCTGGTTTA

GTGAACCGGATCCCCCGGGCTGCAGGAATTTATGAAATCCTTTATGGGGACCCC

CCCCTTTGTCAACCTTGCTCAATTCCTTCTCCCCCTCCGATCCTAAGACTGATTTAC

AAGCCCGACTAAAAGGGCTGCAAGCGGTGCAGGCCCAAATCTGGACACCCCTGGC

CGAATTGTACCGGCCAGGACATCCACAAACTAGCCACCCATTTCAGGTGGGAGACT

CCGTGTACGTCCGGCGGCACGCCTCTCAAGGATTGGAGCCTCGTTGGAAGGGACC

TTACATCGTCCTGCTGACCACGCCCACCGCCATAAAGGTTGACGGGATCGCCGCC

TGGATTCACGCATCGCACGCCAAGGCAGCCCCAAAAACCCCTGGACCAGAAACTC

CCAAAACCTGGAAGCTCCGCCGTTCGGAGAACCCTCTTAAGATAAGACTCTCCCGT

GTCTGACTGCTAATCCACCTTGTCCCTGTACTAACCCAAA

-continued (Nucleotide sequence of CMV-RD114UTR)
SEQ ID NO: 23
ACTAGTTCCGCCAGAGCGCGCGAGGGCCTCCAGCGGCCGCCCCTCCCCCACAGC

AGGGGCGGGGTCCCGCGCCCACCGGAAGGAGCGGGCTCGGGGCGGGCGGCGCT

GATTGGCCGGGGCGGGCCTGACGCCGACGCGGCTATAAGAGACCACAAGCGACC

CGCAGGGCCAGACGTTCTTCGCCGAAGCTT (Sv40 PolyA)
SEQ ID NO: 24
CAGACATGATAAGATACATTGATGAGTTTGGACAAACCACAACTAGAATGCAGTGAA

AAAAATGCTTTATTTGTGAAATTTGTGATGCTATTGCTTTATTTGTAACCATTATAAGC

TGCAATAAACAAGTTAACAACAACAATTGCATTCATTTTATGTTTCAGGTTCAGGGG

GAGGTGTGGGAGGTTTTTT (RD114 Intron)
SEQ ID NO: 25
GATCCCCCGGGCTGCAGGAATTTATGAAATCCTTTATGGGGGACCCCCCCCTTTGT

CAACCTTGCTCAATTCCTTCTCCCCCTCCGATCCTAAGACTGATTTACAAGCCCGAC

TAAAAGGGCTGCAAGCGGTGCAGGCCCAAATCTGGACACCCCTGGCCGAATTGTA

CCGGCCAGGACATCCACAAACTAGCCACCCATTTCAGGTGGGAGACTCCGTGTAC

GTCCGGCGGCACCGCTCTCAAGGATTGGAGCCTCGTTGGAAGGGACCTTACATCG

TCCTGCTGACCACGCCCACCGCCATAAAGGTTGACGGGATCGCCGCCTGGATTCA

CGCATCGCACGCCAAGGCAGCCCCAAAAACCCCTGGACCAGAAACTCCCAAAACC

TGGAAGCTCCGCCGTTCGGAGAACCCTCTTAAGATAAGACTCTCCCGTGTCTGACT

GCTAATCCACCTTGTCCCTGTACTAACCCAAA (MEF1 Intron)
SEQ ID NO: 26
GCCGTCAGAACGCAGGTGAGGGGCGGGTGTGGCTTCCGCGGGCCGCCGAGCTG

GAGGTCCTGCTCCGAGCGGGCCGGGCCCCGCTGTCGTCGGCGGGGATTAGCTGC

GAGCATTCCCGCTTCGAGTTGCGGGCGGCGCGGGAGGCAGAGTGCGAGGCCTAG

CGGCAACCCCGTAGCCTCGCCTCGTGTCCGGCTTGAGGCCTAGCGTGGTGTCCGC

GCCGCCGCCGCGTGCTACTCCGGCCGCACTCTGGTCTTTTTTTTTTTGTTGTTGTT

GCCCTGCTGCCTTCGATTGCCGTTCAGCAATAGGGGCTAACAAAGGGAGGGTGCG

GGGCTTGCTCGCCCGGAGCCCGGAGAGGTCATGGTTGGGGAGGAATGGAGGGAC

AGGAGTGGCGGCTGGGGCCCGCCCGCCTTCGGAGCACATGTCCGACGCCACCTG

GATGGGGCGAGGCCTGGGGTTTTTCCCGAAGCAACCAGGCTGGGGTTAGCGTGC

CGAGGCCATGTGGCCCCAGCACCCGGCACGATCTGGCTTGGCGGCGCCGCGTTG

CCCTGCCTCCCTAACTAGGGTGAGGCCATCCCGTCCGGCACCAGTTGCGTGCGTG

GAAAGATGGCCGCTCCCGGGCCCTGTTGCAAGGAGCTCAAAATGGAGGACGCGG

CAGCCCGGTGGAGCGGGCGGGTGAGTCACCCACACAAAGGAAGAGGGCCTGGTC

CCTCACCGGCTGCTGCTTCCTGTGACCCCGTGGTCCTATCGGCCGCAATAGTCAC

CTCGGGCTTTTGAGCACGGCTAGTCGCGGCGGGGGAGGGGATGTAATGGCGTT

GGAGTTTGTTCACATTTGGTGGGTGGAGACTAGTCAGGCCAGCCTGGCGCTGGAA

GTCATTTTTGGAATTTGTCCCCTTGAGTTTTGAGCGGAGCTAATTCTCGGGCTTCTT

AGCGGTTCAAAGGTATCTTTTAAACCCTTTTTTAGGTGTTGTGAAAACCACCGCTAA

TTCAAAGCAACCGG

The invention claimed is:

1. A plasmid system for transfection into a cell to create a producer cell, the system comprising:
   a) a helper plasmid comprising a first nucleotide sequence encoding Murine leukemia virus (MLV)-derived Gag and Pol poly-proteins,
   b) an envelope plasmid comprising a second nucleotide sequence encoding an Env protein,
   c) a genome plasmid comprising a third nucleotide sequence comprising a retroviral genome,
   wherein the first nucleotide sequence comprises the sequence selected from SEQ ID NO: 1, SEQ ID NO: 2 or SEQ ID NO: 3, and
   wherein the second nucleotide sequence is codon-optimized for expression in the producer cell.

2. The system of claim 1, wherein the second nucleotide sequence comprises the sequence selected from SEQ ID NO: 7, SEQ ID NO: 8, SEQ ID NO: 9, SEQ ID NO: 10 or SEQ ID NO: 11.

3. The system of claim 1, wherein the Env protein is RD114 Envelope protein.

4. The system of claim 3, wherein the codon adaptation index (CAI) of the second nucleotide sequence is at least 0.75.

5. The system of claim 1, wherein the genome plasmid further comprises a nucleotide of interest (NOI).

6. The system of claim 1, wherein genome plasmid comprises a packaging signal, which has homology with a portion of the wildtype MLV nucleotide sequence encoding Gag and/or Pol polyprotein(s).

7. A producer cell capable of producing retroviral vectors, comprising the plasma system of claim 1.

8. A nucleotide sequence encoding MLV-derived Gag and Pol poly-proteins comprising the sequence selected from: SEQ ID NO: 1 to SEQ ID NO: 3.

9. A nucleotide sequence encoding Env protein comprising the sequence selected from: SEQ ID NO: 5 to SEQ ID NO: 7 and SEQ ID NO: 9 to 11.

* * * * *

SEQUENCE LISTING

<160> NUMBER OF SEQ ID NOS: 26

<210> SEQ ID NO 1
<211> LENGTH: 5217
<212> TYPE: DNA
<213> ORGANISM: Artificial Sequence
<220> FEATURE:
<223> OTHER INFORMATION: Gag and Pol polyproteins codon-shuffled variant

<400> SEQUENCE: 1

```
atgggccaaa ccgtgaccac cccgctgtcg ctgactctgg ggcattggaa ggatgtggaa     60
cgcatcgccc acaaccagag cgtggacgtg aagaagcgcc gctgggtgac cttctgctcc    120
gcagaatggc ctacctttaa cgtggggtgg cctcgggacg caccttcaa tcgggacctg     180 atcacccagg tgaaaatcaa ggtgttcagc ccgggtccgc acggccatcc agatcaagtc    240
ccgtacatcg tgacttggga agccctggcg ttcgaccccc accgtgggt caaaccattc     300 gtccacccga agccaccgcc accctgccg ccgtcggcgc cctcactgcc gctggaacct     360
ccgagatcga ctcctccgag atcatcgctc tacccggcgc tcactccgag cctgggcgca    420
aagccaaagc cgcaagtgct gtccgattcg ggaggacctc tcatcgacct gctcaccgag    480
gaccctccac cctacagaga tccgcgccct ccccgagcg acagggacgg aacggcggg     540 gaggccaccc cggcaggaga agccccggac ccaagcccta tggcgtcaag actcagaggc    600
agaagagaac ctccggtggc agactcgact acttcgcagg cattcccact gcgcgccggg    660
ggaaatggcc agctgcagta ctggccgttc agctcatcgg acctctacaa ttggaagaac    720
aacaatccct cgttctcgga ggaccctggt aaactaaccg ctttgatcga atcggtcctg    780
attacccacc agccgacctg ggacgactgc agcagctcc tgggcactct gctgaccgga     840
gaggaaaaac aaagagtgct gctggaagca cggaaggcag tgcgcgggga tgatggcagg    900
ccgacccagc tcccgaacga ggtggacgct gccttcccac tggaacgccc agattgggac    960
tacaccaccc aagctggaag aaaccacctg gtccattacc gccaactgct gctggcagga   1020
ctccaaaacg caggacggtc ccctactaac ctggccaagg tgaaagggat tactcaaggc   1080
ccgaacgagt cgccgagcgc gttcctagag cgcctaaaag aggcctaccg gcgctacacc   1140
ccatatgacc cagaggaccc aggacaggaa accaatgtga gcatgtcatt catctggcag   1200 tcagccccg acatcggacg caagctggaa cgcctggaag acctgaagaa taaaacgctc    1260
ggcgatctgg tgcgggaagc agagaagatt ttcaataaac gggaaacccc ggaagagcgg   1320
gaggaacgca tccggcgcga gaccgaagaa aaggaggaac gcagacgcac cgaggatgaa   1380
cagaaggaga aggagagaga ccgccgccgg caccgcgaaa tgtcgaaact gctggccacg   1440
gtggtcagcg tcagaagca ggatcgccaa ggaggcgagc gcagaagatc gcaactggat    1500
cgcgaccagt gcgcctactg caaggagaag gggcactggg cgaaagattg tcccaagaaa   1560
ccacgaggac ctcgggacc aagaccccag acctccctcc tgaccctaga tgactaggga    1620
ggtcagggtc aggagccccc ccctgaaccc aggataaccc tcaaagtcgg ggggcaaccc   1680
gtcaccttcc tggtggacac cggcgcgcag cacagcgtgc tgacccaaaa cccgggacct   1740
ctgtcagaca gtccgcctg gtgcagggc gcaactggag ggaagcggta tcggtggacc     1800
actgatcgca aagtgcacct ggcaacggga aaagtgaccc attcatttct gcacgtgccg   1860
gactgcccgt accgcttct gggacgcgac ctcctgacta agctcaaggc acagatccac   1920
ttcgagggat caggagcgca ggtcatggga cctatggaca accattgca ggtcctgacc   1980 ttgaacatcg aagacgagta caggctgcac gagactagca aggaacctga cgtgtcgctg   2040
```

```
gggagcacct ggctgtcgga cttccccaa gcctgggcag agaccggagg aatgggctc      2100 gcggtcagac aggcaccact catcatccca ctcaaggcca cctccacccc ggtctcaatt    2160
aagcaatacc cgatgtcgca ggaagcccgc ctcggaatca agccgcatat tcaacgcctc    2220
ctggaccaag ggattctggt gccgtgccag tcgccgtgga acaccccact attgccggtc    2280
aagaagcctg gaactaacga ttacaggccg gtgcaggacc tgcgggaagt gaacaaacgg    2340
gtggaggaca tccacccgac cgtgccgaat ccgtacaacc ttctgtccgg actccctccc    2400
tcacatcagt ggtacactgt gctcgacctt aaggacgcgt tcttctgcct gcgcctgcat    2460
ccgacgtcac agccgttgtt cgctttcgag tggcgcgatc ccgaaatggg tatctcgggc    2520
caactgactt ggactcggct gccacaagga ttcaagaact cgccaactct gtttgatgaa    2580
gctctacacc gcgacctggc cgacttcaga atccaacacc cggacctgat cctgcttcaa    2640
tacgtggatg acctgctgct cgccgcgact tccgagctgg actgtcagca gggcactaga    2700
gcactgctac agaccttggg taatctggga tacagagcaa cgccaagaa agctcagatt     2760 tgccaaaagc aagtgaagta cctgggctac cttctcaaag aaggccagag atggctgacc    2820
gaagccagaa aggagaccgt gatgggacaa ccgacccta aaccctcg gcagctgcgc       2880 gagttcctgg aaccgcagg cttctgccgc ctgtggattc ccggattcgc agagatggcc     2940
gccccgctat accctctgac caagaccgga accctgttta attggggacc tgaccagcag    3000
aaggcgtacc aagagatcaa gcaagccctg ctgaccgccc ctgccctcgg actgccggac    3060
ctgactaagc cctttgagct gttcgtggac gagaagcaag gatacgcaaa gggcgtcctg    3120
actcagaagc tgggaccgtg gagaagaccg gtcgcgtacc tgtccaagaa gctggacccg    3180
gtggccgctg gatggccacc gtgcctgcgg atggtggctg ccattgctgt gctcaccaag    3240
gacgcaggca agctgactat gggacagcca ctggtgatcc tcgcaccgca cgccgtggag    3300
gctctggtga acagcctcc tgaccggtgg ctgtccaatg cgcgcatgac tcattaccag    3360
gccctgctcc tagacaccga tcgggtgcag ttcggaccag tggtggcact gaacccagca    3420
actctgctgc cgctgccgga agaggggttg cagcacgact gcctggacat cctcgcagaa    3480
gctcacggaa cgcggtccga ccttaccgac caaccactgc ccgatgctga tcacacttgg    3540
tacactgatg ggtcatcatt cctgcaagaa ggccagcgca aagcagggc tgcagtgact     3600 accgaaactg aagtcatttg ggctcgggca ctgccggcgg ggacgtcggc acagcgggcg    3660
gaactcatcg cactcaccca ggcgctgaag atggccgagg gcaaaaagct gaacgtgtac    3720
accgactcaa gatacgcgtt cgcaactgca catatccacg gggagattta cagacggcgc    3780
ggtctgctga cttcggaggg caaggaaatc aaaaacaagg acgagatcct ggcgctcctg    3840
aaagccctgt tcctgccaaa gcggctgtca atcatccact gccctggcca tcagaagggt    3900
aactccgctg aagccagggg aaaccgcatg gccgatcaag ccgcgcgcga ggtcgctacc    3960
agagagaccc ccggaacttc gacgctgctt atcgagaact ccacgccata cacccacgag    4020
cactttcact acactgtcac cgacactaag gatctaacta agctgggtgc cacttatgat    4080
agcgcaaaga agtactgggt gtaccagggg aagcctgtga tgcccgatca gttcaccttc    4140
gagctgctgg atttcctgca tcaactgacg cacctgagct tctcaaagac caaggctctg    4200
ctggaacgca gccccttcgcc gtactatatg ttgaataggg atcgcaccct gaagaatatc    4260
accgaaacct gcaaggcctg cgcccaggtg aatgcttcca gtccgccgt gaagcagggc     4320 acccgcgtcc gcggacaccg ccctggaact cactgggaga tcgacttcac tgaggtgaaa    4380
```

-continued

```
ccgggccttt acggctacaa atacctgctg gtgttcgtgg acactttctc gggatggatc    4440
gaggccttcc cgactaaaaa ggaaactgca aaagtggtga ctaagaagct gctggaggag    4500
attttccccc gctttggcat gccgcaggta ttgggaactg acaatgggcc tgccttcgtc    4560
tccaaggtga gtcagacagt ggccgatctg ttggggattg attggaaatt acattgtgca    4620
tacagacccc aaagctcagg tcaggtagaa agaatgaata ggaccatcaa ggagactttg    4680
actaaattaa cgcttgcaac tggctctaga gactgggtgc tcctactccc cttagccctg    4740
taccgagccc gcaacacgcc gggcccccat ggcctcaccc catatgagat cttatatggg    4800 gcaccccgc cccttgtaaa cttccctgac cctgacatga ccagagttac taacagcccc    4860
tctctccaag ctcacttaca ggctctctac ttagtccagc acgaagtttg agaccactg    4920 gcggcagctt accaagaaca actgaccgg ccggtggtgc ctcaccctta ccgggtcggc    4980
gacacagtgt gggtccgccg acatcaaacc aagaacctag aacctcgctg gaaaggacct    5040
tacacagtcc tgctgaccac ccccaccgcc ctcaaagtag acggtatcgc agcttggata    5100
cacgcagccc acgtaaaggc ggccgacacc gagagtggac catcctctgg acggacatgg    5160
cgcgttcaac gctctcaaaa ccccctcaag ataagattaa cccgtggaag cccttag      5217
```

<210> SEQ ID NO 2
<211> LENGTH: 5217
<212> TYPE: DNA
<213> ORGANISM: Artificial Sequence
<220> FEATURE:
<223> OTHER INFORMATION: Gag and Pol polyproteins codon-shuffled variant

<400> SEQUENCE: 2

```
atgggtcaga cggtgactac tccgctttca ctcacactcg gtcattggaa agacgttgag      60
cgaatcgcgc acaatcagag tgtggacgta aaaaagcgcc gctgggttac gttctgttct     120
gctgagtggc ctacgtttaa tgtagggtgg ccaagggatg gcactttcaa cagggatctg     180
ataacacagg taaagataaa agttttttagt ccaggcccac acgtcatcc tgatcaggtg     240 ccttacattg taacatggga agcactggcg tttgatcctc cgccgtgggt taaacccttt     300
gtacacccca aacccctcc accactccca ccctctgccc catcattgcc gttggaaccg     360
cccaggtcta cgccccccg ctcatccctt taccctgctc tgacacctag ccttggtgcc     420
aaacccaagc cacaagtgct ctcagacagc ggcggccctc tgatagattt gctgactgaa     480
gatccgcctc cttatcgcga cccgcggcct ccaccgtcag atagggatgg caatggcggc     540
gaagccacac ccgcaggtga ggcccctgat ccaagtccca tggcttctcg acttcgaggc     600
cgacgggagc cgcctgtcgc tgatagtacg acttcacaag cattcccttt gagagcgggg     660
gggaatgggc aattgcaata ttggcccttt agcagcagtg acctgtacaa ttggaaaaac     720
ataacccctt cttttagtga ggatcctggt aagcttacgg ctttgatagg atccgtgctt     780
attacacatc agccgacatg gatgactgc caacaactct gggtacatt gctgacgggt     840 gaagaaaaac agcgcgtgct cttggaagcc aggaaagctg tacgcggcga cgacggtcgg     900
cccacacagc ttcctaacga agtcgacgcc gcttttcctc tcgagcggcc agattgggat     960
tacacaaccc aggccggccg gaaccatttg gtacattacc ggcaactctt gttggcaggg    1020
ttgcaaaacg ctggtcggag ccccacgaac ttggcgaaag tgaagggtat cacccaaggc    1080
ccaaacgagt caccttcagc ttttctcgaa cgacttaaag aagcctacag acgatacact    1140
ccgtacgatc cagaggaccc gggccaggaa accaacgtat ctatgtcttt catttggcag    1200
agcgctccag acatcgggcg aaaactggaa cgcctcgaag acctgaagaa taaaactctc    1260
```

```
ggtgacctcg ttcgcgaagc cgagaaaatt tttaataaaa gagaaactcc ggaagagcgc   1320
gaggaaagaa ttaggcgcga gacggaggaa aagaagaac ggaggagaac cgaggacgaa    1380
caaaaggaga aagagcgaga ccgacggcgc cacagagaaa tgagcaaact gcttgccacc   1440
gtggtgagcg gtcaaaagca agaccgacag ggaggggagc ggagacgaag tcagctcgac   1500
agggaccagt gtgcttattg taaagaaaag ggccactggg ctaaagactg ccccaaaaaa   1560
ccgagaggcc ccaggggtcc gagaccgcag acctctttgt tgactttgga tgattaaggc   1620
ggacagggtc aagagcctcc accggaacca cgcataactc tcaaagtggg aggccagcca   1680
gtaacgtttc tcgtcgacac aggagcacaa cattcagttc ttactcaaaa cccagggccg   1740
ctgagtgaca agtctgcttg ggtgcaggga gctactggag ggaagcggta ccggtggacg   1800
acggaccgga aagtgcatct ggcgacgggt aaagtaacac actctttctt gcatgtaccg   1860
gattgcccct acccacttct cggccgcgac ttgcttacaa aacttaaagc tcagatccat   1920
ttcgagggaa gcggggctca gtaatgggc ccgatgggc agcctcttca ggtcctgacc     1980
ttgaatatcg aagacgagta tcgcttgcat gaaacctcta aggaacctga tgtgtctctg   2040
gggtcaacgt ggctgtccga cttttcctcag gcatgggctg aaaccggagg catgggtttg  2100
gcggtcagac aggcaccgct tattattccc cttaaggcga cgtctacgcc cgtctcaata   2160
aaacaatacc caatgtctca agaagcccgg ctgggaatca agcctcacat tcaaagactg   2220
ctcgatcagg gcatcctcgt cccttgccag agcccgtgga atacgcctct gttgccggtg   2280
aagaagcccg gcacgaatga ctatcggcct gtccaggacc tccgggaagt gaacaagaga   2340
gtggaggaca tacaccctac agtgcccaat ccctataatc tgctgtccgg tctccctcct   2400
tcccatcaat ggtatacggt cctcgatctg aaggatgcct ttttttgtct taggcttcac   2460
cctacgtctc aacccctctt cgccttcgag tggcgcgatc ccgaaatggg gatcagcgga   2520
caacttactt ggactaggct tccccagggg ttcaaaaata gtcccacact gttcgatgag   2580
gctctgcaca gggacttggc ggatttccgg atacaacacc ctgacctcat tttgcttcaa   2640
tatgtcgacg atcttctcct ggcggccaca tctgaactcg attgccaaca aggaactagg   2700
gctcttctgc aaactctcgg aaacttgggt tatcgggcta gtgcaaaaaa ggctcagata   2760
tgccagaaac aagtaaagta cctcggctat ctcctgaaag aagggcaacg gtggctcaca   2820
gaagcaagga aggaaacggt gatgggccag ccaactccga aaacgccccg acagttgaga   2880
gagttcctgg gtacagcggg gttttgccga ctctggatcc cgggctttgc ggaaatggcc   2940
gccccactgt atccgcttac caagacggga acgcttttta actgggggcc tgaccaacaa   3000
aaggcatacc aggaaatcaa gcaagcactg ctcacagctc cagcgctcgg tctcccggac   3060 ttgactaaaac cctttgaact ttttgttgat gagaagcaag gctatgcaaa gggcgtgctt   3120
acacagaagt tgggtccatg gagaaggccg gttgcctatt tgtccaaaaa actggaccct   3180
gtggcagctg gctggccccc atgcttgagg atggtagctg ccatagctgt gctgaccaag   3240
gacgcaggga aacttaccat gggccaacct cttgtgatac ttgcaccgca tgctgttgaa   3300
gccctggtca gcaaccgcc ggaccgctgg ctctctaacg cgaggatgac gcactaccaa   3360
gctttgctcc tcgacacgga ccgggtccaa ttcggtcctg tcgtcgcgct caatcccgcg   3420
acactcctcc cccttcctga ggaagggctg caacatgact gtctcgacat acttgcagaa   3480
gcacacggca cgcggtcaga cttgacagac cagcctctcc ctgatgccga ccacacttgg   3540
tataccgatg gcagtagttt tttgcaggaa ggtcagcgaa aggctggcgc cgcagtcacc   3600
```

```
acagaaactg aggtaatttg ggcgagggct ctcccagctg ggacatctgc tcaacgcgcg    3660
gaactcattg cactcaccca agccctgaag atggcagaag gaaaaaaatt gaatgtctac    3720
actgattccc ggtatgcttt tgccacggcg catatccatg gggagatata tcgacgccga    3780
ggtctgctta cgtctgaagg taaggagatt aaaaacaaag acgagatcct cgcccttctg    3840
aaggcactgt tcttgccaaa aagactgagt atcatacact gtcctggaca ccagaaaggt    3900
aattcagccg aagcgagggg taaccggatg gcagatcaag cagcacggga agtcgctacc    3960
cgagaaaccc ccggaacctc caccctttg atcgagaaca gtactcctta cactcacgag     4020
catttccatt atacagtgac ggacacgaaa gatttgacga aactgggtgc aacgtacgat    4080
agtgcaaaaa aatactgggt atatcagggc aaacccgtga tgcctgacca gttcacgttc    4140
gagcttctgg atttcctcca ccagcttacg catttgtctt tttccaagac gaaagcgctt    4200
ctggaacggt ctccgtcccc atattatatg ttgaatagaa ataggacctt gaaaaatata    4260
acagaaacct gcaaggcttg tgctcaagtg aatgcttcca agagcgcagt caaacaaggt    4320
acgagggtca gaggccacag gccaggaacc cattgggaga tcgacttcac tgaggtgaaa    4380
ccaggccttt acggctacaa gtaccttctt gttttgttg atacgttctc cggctggatc     4440
gaggcctttc caactaagaa ggagactgcg aaagtggtca caaagaaact cctggaagaa    4500
atcttcccgc gctttgggat gcctcaggtc cttgggaccg ataacgggcc tgcttttgta    4560
tccaaagtca gccaaacagt cgccgacctc ttgggaatcg attggaaact gcactgtgcc    4620
tatcgccccc agtcaagcgg ccaagtagaa aggatgaaca ggacaatcaa agaaactctc    4680
accaagctga ctttggcaac tgggtcacgc gactgggtct tgcttttgcc acttgctctt    4740
taccgcgctc gcaacacacc cggtccccac ggtctcactc catatgagat tttgtatggc    4800
gcaccacccc ctctcgtgaa ttttcccgat cctgacatga cgagggtcac caactctccc    4860
tctttgcagg ctcatcttca ggcgctttat cttgtgcagc acgaggtttg gagacctctt    4920
gcagctgcat accaagaaca gcttgacagg cctgtcgtgc cacatccgta ccgggtcgga    4980
gatacggtat gggtaaggag acaccaaact aaaaacctgg agccaagatg gaaagggcct    5040
tatactgttc tcctgactac gcctactgct ctcaaggttg atggcatagc agcctggatt    5100
catgcggccc atgttaaggc tgcagataca gaatccggtc cctcatccgg aaggacatgg    5160
cgggttcaaa ggtcccaaaa ccccctcaaa attcgactca cacgcggctc cccgtaa      5217
```

<210> SEQ ID NO 3
<211> LENGTH: 5217
<212> TYPE: DNA
<213> ORGANISM: Artificial Sequence
<220> FEATURE:
<223> OTHER INFORMATION: Gag and Pol polyproteins codon-shuffled variant

<400> SEQUENCE: 3

```
atgggccaga ccgtgaccac cccccctgagc ctgaccctgg ccactggaa ggacgtggag       60 cgcatcgccc acaaccagag cgtggacgtg aagaagcgcc gctgggtgac cttctgcagc    120
gccgagtggc ccaccttcaa cgtgggctgg ccccgcgacg gcaccttcaa ccgcgacctg    180
atcacccagg tgaagatcaa ggtgttcagc cccggcccc acggccaccc cgaccaggtg     240
ccctacatcg tgacctggga ggccctggcc ttcgacccc ccctgggt gaagcccttc        300 gtgcacccca gcccccccc ccctgccc ccagcgccc ccagcctgcc cctggagccc         360
ccccgcagca ccccccccg cagcagcctg taccccgccc tgaccccag cctgggcgcc      420 aagcccaagc ccaggtgct gagcgacagc ggcggccccc tgatcgacct gctgaccgag    480
```

-continued

```
gaccccccc cctaccgcga ccccccgcccc cccccagcg accgcgacgg caacggcggc      540
gaggccaccc ccgccggcga ggcccccgac cccagcccca tggccagccg cctgcgcggc      600
cgccgcgagc cccccgtggc cgacagcacc accagccagg ccttcccccct gcgcgccggc    660
ggcaacggcc agctgcagta ctggcccttc agcagcagcc acctgtacaa ctggaagaac      720
aacaacccca gcttcagcga ggaccccggc aagctgaccg ccctgatcga gagcgtgctg      780
atcacccacc agcccacctg ggacgactgc agcagctgc tgggcaccct gctgaccggc      840
gaggagaagc agcgcgtgct gctggaggcc cgcaaggccg tgcgcggcga cgacggccgc     900
cccacccagc tgcccaacga ggtggacgcc gccttccccc tggagcgccc cgactgggac     960
tacaccaccc aggccggccg caaccacctg gtgcactacc gccagctgct gctggccggc    1020
ctgcagaacg ccggccgcag ccccaccaac ctggccaagg tgaagggcat cacccagggc    1080
cccaacgaga gccccagcgc cttcctggag cgcctgaagg aggcctaccg ccgctacacc    1140
ccctacgacc ccgaggaccc cggccaggag accaacgtga gcatgagctt catctggcag    1200
agcgcccccg acatcggccg caagctggag cgcctggagg acctgaagaa caagaccctg    1260
ggcgacctgg tgcgcgaggc cgagaagatc ttcaacaagc gcgagacccc cgaggagcgc    1320
gaggagcgca tccgccgcga gaccgaggag aaggaggagc gccgccgcac cgaggacgag    1380
cagaaggaga aggagcgcga ccgccgccgc caccgcgaga tgagcaagct gctggccacc    1440
gtggtgagcg ccagaagca ggaccgccag ggcggcgagc gccgccgcag ccagctggac    1500
cgcgaccagt gcgcctactg caaggagaag ggccactggg ccaaggactg ccccaagaag    1560
ccccgcggcc cccgcggccc ccgccccag accagcctgc tgaccctgga cgactaaggc    1620
ggccagggcc aggagccccc cccgagccc cgcatcaccc tgaaggtggg cggccagccc    1680
gtgaccttcc tggtggacac cggcgcccag cacagcgtgc tgacccagaa ccccggcccc    1740
ctgagcgaca gagcgcctg ggtgcagggc gccaccggcg gcaagcgcta ccgctggacc    1800
accgaccgca aggtgcacct ggccaccggc aaggtgaccc acagcttcct gcacgtgccc    1860
gactgcccct accccctgct gggccgcgac ctgctgacca gctgaaggc ccagatccac    1920
ttcgagggca gcggcgccca ggtgatgggc cccatgggcc agcccctgca ggtgctgacc    1980
ctgaacatcg aggacgagta ccgcctgcac gagaccagca aggagcccga cgtgagcctg    2040
ggcagcacct ggctgagcga cttcccccag gcctgggccg agaccggcgg catgggcctg    2100
gccgtgcgcc aggcccccct gatcatcccc ctgaaggcca ccagcacccc cgtgagcatc    2160
aagcagtacc ccatgagcca ggaggcccgc ctgggcatca gccccacat ccagcgcctg    2220
ctggaccagg gcatcctggt gccctgccag agcccctgga acaccccccct gctgccgtg    2280
aagaagcccg gcaccaacga ctaccgcccc gtgcaggacc tgcgcgaggt gaacaagcgc    2340
gtggaggaca tccacccccac cgtgcccaac ccctacaacc tgctgagcgg cctgccccc    2400
agccaccagt ggtacaccgt gctggacctg aaggacgcct tcttctgcct cgcctgcac    2460
cccaccagcc agcccctgtt cgccttcgag tggcgcgacc ccgagatggg catcagcggc    2520
cagctgacct ggaccgcct gcccagggc ttcaagaaca gccccaccct gttcgacgag    2580
gccctgcacc gcgacctggc cgacttccgc atccagcacc ccgacctgat cctgctgcag    2640
tacgtggacg acctgctgct ggccgccacc agcgagctgg actgccagca gggcacccgc    2700
gccctgctgc agaccctggg caacctgggc taccgcgcca cgccaagaa ggcccagatc    2760
tgccagaagc aggtgaagta cctgggctac ctgctgaagg agggccagcg ctggctgacc    2820
```

```
gaggcccgca aggagaccgt gatgggccag cccaccccca agacccccg ccagctgcgc    2880
gagttcctgg gcaccgccgg cttctgccgc ctgtggatcc ccggcttcgc cgagatggcc    2940
gcccccctgt acccctgac caagaccggc accctgttca actggggccc cgaccagcag    3000
aaggcctacc aggagatcaa gcaggccctg ctgaccgccc ccgccctggg cctgcccgac    3060
ctgaccaagc ccttcgagct gttcgtggac gagaagcagg gctacgccaa gggcgtgctg    3120
acccagaagc tgggcccctg cgccgcccc gtggcctacc tgagcaagaa gctggacccc    3180
gtggccgccg gctggccccc ctgcctgcgc atggtggccg ccatcgccgt gctgaccaag    3240
gacgccggca agctgaccat gggccagccc ctggtgatcc tggcccccca cgccgtggag    3300
gccctggtga agcagccccc cgaccgctgg ctgagcaacg cccgcatgac ccactaccag    3360
gccctgctgc tggacaccga ccgcgtgcag ttcggccccg tggtggccct gaaccccgcc    3420
accctgctgc ccctgcccga ggagggcctg cagcacgact gcctggacat cctggccgag    3480
gcccacggca cccgcagcga cctgaccgac cagcccctgc cgacgccga ccacacctgg    3540
tacaccgacg gcagcagctt cctgcaggag ggccagcgca aggccggcgc cgccgtgacc    3600
accgagaccg aggtgatctg ggcccgcgcc ctgcccgccg gcaccagcgc ccagcgcgcc    3660
gagctgatcg ccctgaccca ggccctgaag atggccgagg caagaagct gaacgtgtac    3720
accgacagcc gctacgcctt cgccaccgcc cacatccacg gcgagatcta ccgccgccgc    3780
ggcctgctga ccagcgaggg caaggagatc aagaacaagg acgagatcct ggccctgctg    3840
aaggccctgt cctgcccaa gcgcctgagc atcatccact gccccggcca ccagaagggc    3900
aacagcgccg aggcccgcgg caaccgcatg gccgaccagg ccgcccgcga ggtggccacc    3960
cgcgagaccc ccggcaccag caccctgctg atcgagaaca gcacccccta cacccacgag    4020
cacttccact acaccgtgac cgacaccaag gacctgacca gctgggcgc cacctacgac    4080
agcgccaaga agtactgggt gtaccagggc aagcccgtga tgcccgacca gttcaccttc    4140
gagctgctgg acttcctgca ccagctgacc cacctgagct tcagcaagac caaggccctg    4200
ctggagcgca gccccagccc ctactacatg ctgaaccgcg accgcaccct gaagaacatc    4260
accgagacct gcaaggcctg cgcccaggtg aacgccagca gagcgccgt gaagcagggc    4320
acccgcgtgc gcggccaccg ccccggcacc cactgggaga tcgacttcac cgaggtgaag    4380
cccgcctgt acggctacaa gtacctgctg gtgttcgtgg acacccttcag cggctggatc    4440
gaggccttcc ccaccaagaa ggagaccgcc aaggtggtga ccaagaagct gctggaggag    4500
atcttccccc gcttcggcat gcccaggtg ctgggcaccg acaacggccc cgccttcgtg    4560
agcaaggtga gccagaccgt ggccgacctg ctgggcatcg actggaagct gcactgcgcc    4620
taccgccccc agagcagcgg ccaggtggag cgcatgaacc gcaccatcaa ggagaccctg    4680
accaagctga ccctggccac cggcagccgc gactgggtgc tgctgctgcc cctggccctg    4740
taccgcgccc gcaacacccc cggccccac ggcctgaccc cctacgagat cctgtacggc    4800
gccccccccc ccctggtgaa cttccccgac cccgacatga cccgcgtgac caacagcccc    4860
agcctgcagg cccacctgca ggcctgtac ctggtgcagc acgaggtgtg cgcccctg     4920
gccgccgcct accaggagca gctggaccgc ccgtggtgc ccaccccta ccgcgtgggc    4980
gacaccgtgt gggtgcgccg ccaccagacc aagaacctgg agcccgctg aagggcccc    5040
tacaccgtgc tgctgaccac ccccaccgcc ctgaaggtgg acggcatcgc cgcctggatc    5100
cacgccgccc acgtgaaggc cgccgacacc gagagcggcc ccagcagcgg ccgcacctgg    5160
cgcgtgcagc gcagccagaa cccctgaag atccgcctga cccgcggcag ccctaa        5217
```

<210> SEQ ID NO 4
<211> LENGTH: 5217
<212> TYPE: DNA
<213> ORGANISM: Artificial Sequence
<220> FEATURE:
<223> OTHER INFORMATION: Wildtype Gag and Pol polyproteins

<400> SEQUENCE: 4

| | |
|---|---|
| atgggccaga ctgttaccac tcccttaagt ttgaccttag gtcactggaa agatgtcgag | 60 |
| cggatcgctc acaaccagtc ggtagatgtc aagaagagac gttgggttac cttctgctct | 120 |
| gcagaatggc caacctttaa cgtcggatgg ccgcgagacg gcacctttaa ccgagacctc | 180 |
| atcacccagg ttaagatcaa ggtctttttca cctggcccgc atggacaccc agaccaggtc | 240 |
| ccctacatcg tgacctggga agccttggct tttgaccccc ctccctgggt caagcccttt | 300 |
| gtacacccta gcctccgcc tcctcttcct ccatccgccc cgtctctccc ccttgaacct | 360 |
| cctcgttcga ccccgcctcg atcctccctt tatccagccc tcactccttc tctaggcgcc | 420 |
| aaacctaaac tcaagttct ttctgacagt gggggccgc tcatcgacct acttacagaa | 480 |
| gacccccgc cttataggga cccaagacca ccccttccg acaggacgg aaatggtgga | 540 |
| gaagcgaccc ctgcgggaga ggcaccggac ccctccccaa tggcatctcg cctacgtggg | 600 |
| agacgggagc cccctgtggc cgactccact acctcgcagg cattccccct ccgcgcagga | 660 |
| ggaaacggac agcttcaata ctggccgttc tcctcttctg acctttacaa ctggaaaaat | 720 |
| aataaccctt cttttttctga agatccaggt aaactgacag ctctgatcga gtctgttctc | 780 |
| atcacccatc agcccacctg gacgactgt cagcagctgt gggactct gctgaccgga | 840 |
| gaagaaaaac aacgggtgct cttagaggct agaaaggcgg tgcggggcga tgatgggcgc | 900 |
| cccactcaac tgcccaatga agtcgatgcc gcttttcccc tcgagcgccc agactgggat | 960 |
| tacaccaccc aggcaggtag gaaccaccta gtccactatc gccagttgct cctagcgggt | 1020 |
| ctccaaaacg cgggcagaag ccccaccaat ttggccaagg taaaaggaat aacacaaggg | 1080 |
| cccaatgagt ctccctcggc cttcctagag agacttaagg aagcctatcg caggtacact | 1140 |
| ccttatgacc ctgaggaccc agggcaagaa actaatgtgt ctatgtcttt catttggcag | 1200 |
| tctgccccag acattgggag aaagttagag aggttagaag atttaaaaaa caagacgctt | 1260 |
| ggagatttgg ttagagaggc agaaaagatc tttaataaac gagaaacccc ggaagaaaga | 1320 |
| gaggaacgta tcaggagaga acagagggaa aagaagaac gccgtaggac agaggatgag | 1380 |
| cagaaagaga agaaaagaga tcgtaggaga catagagaga tgagcaagct attggccact | 1440 |
| gtcgttagtg gacagaaaca ggatagacag ggaggagaac aaggaggtc ccaactcgat | 1500 |
| cgcgaccagt gtgcctactg caaagaaaag gggcactggg ctaaagattg tcccaagaaa | 1560 |
| ccacgaggac ctcggggacc aagaccccag acctccctcc tgaccctaga tgactaggga | 1620 |
| ggtcagggtc aggagccccc ccctgaaccc aggataaccc tcaaagtcgg ggggcaaccc | 1680 |
| gtcaccttcc tggtagatac tggggcccaa cactccgtgc tgacccaaaa tcctggaccc | 1740 |
| ctaagtgata gtctgcctg gtccaagggg ctactggag aaagcggta tcgctggacc | 1800 |
| acggatcgca agtacatct agctaccggt aaggtcaccc actctttcct ccatgtacca | 1860 |
| gactgtccct atcctctgtt aggaagagat ttgctgacta aactaaaagc ccaaatccac | 1920 |
| tttgagggat caggagctca ggttatggga ccaatgggc agcccctgca agtgttgacc | 1980 |
| ctaaatatag aagatgagta tcggctacat gagacctcaa aagagccaga tgtttctcta | 2040 |

```
gggtccacat ggctgtctga ttttcctcag gcctgggcgg aaaccggggg catgggactg    2100
gcagttcgcc aagctcctct gatcatacct ctgaaagcaa cctctacccc cgtgtccata    2160
aaacaatacc ccatgtcaca agaagccaga ctggggatca agccccacat acagagactg    2220
ttggaccagg gaatactggt accctgccag tccccctgga acacgcccct gctacccgtt    2280
aagaaaccag ggactaatga ttataggcct gtccaggatc tgagagaagt caacaagcgg    2340
gtggaagaca tccaccccac cgtgcccaac ccttacaacc tcttgagcgg gctcccaccg    2400
tcccaccagt ggtacactgt gcttgattta aaggatgcct ttttctgcct gagactccac    2460
cccaccagtc agcctctctt cgcctttgag tggagagatc cagagatggg aatctcagga    2520
caattgacct ggaccagact cccacagggt ttcaaaaaca gtcccaccct gtttgatgag    2580
gcactgcaca gagacctagc agacttccgg atccagcacc cagacttgat cctgctacag    2640
tacgtggatg acttactgct ggccgccact tctgagctag actgccaaca aggtactcgg    2700
gccctgttac aaaccctagg gaacctcggg tatcgggcct cggccaagaa agcccaaatt    2760
tgccagaaac aggtcaagta tctggggtat cttctaaaag agggtcagag atggctgact    2820
gaggccagaa aagagactgt gatggggcag cctactccga agaccctcg acaactaagg    2880 gagttcctag ggacggcagg cttctgtcgc tctggatcc ctgggtttgc agaaatggca    2940 gccccttgt accctctcac caaaacgggg actctgttta attggggccc agaccaacaa    3000
aaggcctatc aagaaatcaa gcaagctctt ctaactgccc cagccctggg gttgccagat    3060
ttgactaagc cctttgaact ctttgtcgac gagaagcagg gctacgccaa aggcgtccta    3120
acgcaaaagc tgggaccttg gcgtcggccg gtggcctacc tgtctaaaaa gctagaccca    3180
gtggcagctg gctggccccc ctgcctacgg atggtggcag ccattgcagt tctgacaaaa    3240
gatgctggca agctcactat gggacagccg ttggtcattc tggcccccca tgccgtagag    3300
gcactagtta agcaacccccc tgatcgctgg ctctccaatg cccggatgac ccattaccaa    3360
gccctgctcc tggacacgga ccgggtccag ttcgggccag tagtggccct aaatccagct    3420
acgctgctcc ctctgcctga ggaggggctg caacatgact gccttgacat cttggctgaa    3480
gcccacggaa ctagatcaga tcttacggac cagcccctcc cagacgccga ccacacctgg    3540
tacacggatg ggagcagctt cctgcaagaa gggcagcgta aggccggagc agcggtgacc    3600
actgagactg aggtaatctg ggccagggca ttgccagccg ggacatcggc caaagagct    3660 gaactgatag cgctcacccca agccctaaag atggcagaag gtaagaagct aaatgtttat    3720
actgatagcc gttacgcttt tgccaccgcc catattcatg gagaaatata cagaaggcgc    3780
gggttgctca catcagaagg aaaagagatc aagaacaagg acgagatctt agccctacta    3840
aaggctctct tcttgcccaa aagacttagc ataattcatt gcccgggaca tcaaaaagga    3900
aacagcgcag aggccagggg caaccggatg gccgaccaag cggcccgaga agtagccact    3960
agagaaactc caggaacttc cacacttctg atagaaaact caaccccta tacccatgaa    4020 cactttcact atacagtaac tgacacaaag gatttgacca aactaggagc cacttatgac    4080
agtgcgaaga aatattgggt ctatcaagga aagcctgtta tgcctgatca attcacccttt    4140 gagttactag actttcttca ccaattgacc cacctcagct tctcaaaaac aaaggctctc    4200
ctagagagaa gccccagtcc ctactacatg ctgaaccggg atcgaacact caaaaatatc    4260
actgagacct gcaaagcttg tgcacaagtc aatgccagca agtctgccgt taagcaagga    4320
actagggtcc gcgggcatcg gcctggcaca cactgggaga tcgatttcac cgaggtaaaa    4380
cctggattgt atggctataa gtatcttttta gttttttgtag atactttttc tggctggata    4440
```

| | |
|---|---|
| gaagctttcc caactaagaa agaaaccgcc aaggtcgtga ccaagaaact gctagaagag | 4500 |
| atcttcccta ggttcggcat gccgcaggta ttgggaactg acaatgggcc tgccttcgtc | 4560 |
| tccaaggtga gtcagacagt ggccgatctg ttggggattg attggaaatt acattgtgca | 4620 |
| tacagacccc aaagctcagg tcaggtagaa agaatgaata ggaccatcaa ggagacttta | 4680 |
| actaaattaa cgcttgcaac tggctctaga gactgggtgc tcctactccc cttagccctg | 4740 |
| taccgagccc gcaacacgcc gggcccccat ggcctcaccc catatgagat cttatatggg | 4800 |
| gcacccccgc cccttgtaaa cttccctgac cctgacatga ccagagttac taacagcccc | 4860 |
| tctctccaag ctcacttaca ggctctctac ttagtccagc acgaagtttg agaccactg | 4920 |
| gcggcagctt accaagaaca actggaccgg ccggtggtgc ctcacccta ccgggtcggc | 4980 |
| gacacagtgt gggtccgccg acatcaaacc aagaacctag aacctcgctg aaaggacct | 5040 |
| tacacagtcc tgctgaccac ccccaccgcc ctcaaagtag acggtatcgc agcttggata | 5100 |
| cacgcagccc acgtaaaggc ggccgacacc gagagtggac catcctctgg acggacatgg | 5160 |
| cgcgttcaac gctctcaaaa cccccctcaag ataagattaa cccgtggaag cccttaa | 5217 |

<210> SEQ ID NO 5
<211> LENGTH: 1698
<212> TYPE: DNA
<213> ORGANISM: Artificial Sequence
<220> FEATURE:
<223> OTHER INFORMATION: RD114 ENV protein codon-optimised variant

<400> SEQUENCE: 5

| | |
|---|---|
| atgaagctgc cgacgggaat ggtgatcctg tgcagcctga ttatcgtgcg cgcggggttc | 60 |
| gacgacccga aaaggctat cgctatcgtg caaaagcagc acgggaaacc atgcgaatgc | 120 |
| agcggtggcc aggtgtcaga ggccccaccg aactcaatcc agcaggtcac ctgcccggt | 180 |
| aaaaccgcat acctgatgac caatcaaaag tggaagtgcc gggtgacccc gaagaatctg | 240 |
| actccaagcg ggggagaact gcagaactgc ccctgcaata ctttccagga ttcaatgcac | 300 |
| tcctcctgtt acaccgaata ccgccagtgc agggcaaata caaaacgta ctacactgcg | 360 |
| accctgctga agatccgctc cggctcccta aatgaagtgc agatcctgca gaatccaaac | 420 |
| caactgttgc agagcccgtg cagaggcagc atcaatcagc cggtctgctg gagcgccacc | 480 |
| gcacctatcc acatctcaga cggaggggga ccgctcgata ccaagcgcgt gtggaccgtg | 540 |
| caaaagcggc tagagcagat ccacaaagct atgcacccgg aactgcaata ccacccgctg | 600 |
| gcgcttccaa aggtccgcga cgatctgtcg ctggacgcgc ggaccttcga catcttgaat | 660 |
| actaccttcc gcctgctgca gatgtcgaat ttcagcctgg cacaggattg ttggctgtgc | 720 |
| ctgaagctgg gtactccgac cccgctgccc atccccaccc cgtcactgac ttactcactc | 780 |
| gcagactcgt tggcaaacgc ctcctgccag attatcccac ctctgctggt gcagccgatg | 840 |
| cagttctcga actccagctg cctgtcatca ccattcatca cgacactga acagattgat | 900 |
| ctgggagcag tgactttcac caactgcact tcagtggcca cgtctcctc gccactgtgc | 960 |
| gctctgaacg gtccgtgtt cctgtgtgga acaatatgg cgtacactta cctgccgcaa | 1020 |
| aactggactg gctgtgcgt gcaagcgtca ctgctgcctg catcgacat tacccctga | 1080 |
| gacgagcccg tcccgatccc ggcaatcgac cactacattc accgccgaa acgggcagtc | 1140 |
| cagttcatcc cgctcctggc tggactgggg atcaccgctg cttcactac cggagccact | 1200 |
| ggcttgggtg tctccgtgac ccagtacacg aagctgtccc ccaactgat ttcggacgtc | 1260 |

-continued

| | |
|---|---|
| caagtcctat cgggaaccat ccaggacctc caggatcagg tcgattccct cgcagaggtg | 1320 |
| gtgctccaga accgcagagg actggatctg ctgaccgctg aacagggagg catctgcctt | 1380 |
| gcactccagg agaagtgctg cttctacgcc aataagtcgg ggatcgtgcg gaacaaaatc | 1440 |
| agaactctgc aggaagaact gcagaagcgc cgggaaagcc tcgccagcaa tccgctgtgg | 1500 |
| accggactcc aaggatttct cccgtatctt ctcccgctgc tggggcctct gctcactctg | 1560 |
| ctgctgatcc tgaccatcgg accgtgcgtc tttagcagac tgatggcatt tatcaacgac | 1620 |
| agactgaacg tggtgcatgc aatggtcctg gcacagcagt accaggccct gaaggccgag | 1680 |
| gaggaagcac aggactag | 1698 |

<210> SEQ ID NO 6
<211> LENGTH: 1698
<212> TYPE: DNA
<213> ORGANISM: Artificial Sequence
<220> FEATURE:
<223> OTHER INFORMATION: RD114 ENV protein codon-optimised variant

<400> SEQUENCE: 6

| | |
|---|---|
| atgaagctgc ccaccggcat ggtgatcctg tgcagcctga tcatcgtgcg cgccggcttc | 60 |
| gacgacccccc gcaaggccat cgccctggtg cagaagcagc acggcaagcc ctgcgagtgc | 120 |
| agcggcggcc aggtgagcga ggccccccccc aacagcatcc agcaggtgac ctgccccggc | 180 |
| aagaccgcct acctgatgac caaccagaag tggaagtgcc gcgtgacccc caagaacctg | 240 |
| accccccagcg gcggcgagct gcagaactgc ccctgcaaca ccttccagga cagcatgcac | 300 |
| agcagctgct acaccgagta ccgccagtgc cgcgccaaca caagaccta ctacaccgcc | 360 |
| accctgctga agatccgcag cggcagcctg aacgaggtgc agatcctgca gaaccccaac | 420 |
| cagctgctgc agagccccctg ccgcggcagc atcaaccagc ccgtgtgctg gagcgccacc | 480 |
| gccccccatcc acatcagcga cggcggcggc ccctggaca ccaagcgcgt gtggaccgtg | 540 |
| cagaagcgcc tggagcagat ccacaaggcc atgcaccccg agctgcagta ccacccctg | 600 |
| gccctgccca aggtgcgcga cgacctgagc ctggacgccc gcaccttcga tcctgaac | 660 |
| accaccttcc gcctgctgca gatgagcaac ttcagcctgg cccaggactg ctggctgtgc | 720 |
| ctgaagctgg gcaccccac ccccctggcc atccccaccc ccagcctgac ctacagcctg | 780 |
| gccgacagcc tggccaacgc cagctgccag atcatccccc ccctgctggt gcagcccatg | 840 |
| cagttcagca acagcagctg cctgagcagc cccttcatca cgacaccga gcagatcgac | 900 |
| ctgggcgccc tgaccttcac caactgcacc agcgtggcca acgtgagcag ccccctgtgc | 960 |
| gccctgaacg gcagcgtgtt cctgtgcggc aacaacatgg cctacaccta cctgcccag | 1020 |
| aactggaccg gctgtgcgt gcaggccagc ctgctgcccg acatcgacat catccccggc | 1080 |
| gacgagcccg tgcccatccc cgccatcgac cactacatcc accgccccaa gcgcgccgtg | 1140 |
| cagttcatcc cctgctggc cggcctgggc atcaccgccg ccttcaccac cggcgccacc | 1200 |
| ggcctgggcg tgagcgtgac ccagtacacc aagctgagcc accagctgat cagcgacgtg | 1260 |
| caggtgctga gcggcaccat ccaggacctg caggaccagg tggacagcct ggccgaggtg | 1320 |
| gtgctgcaga accgccgcgg cctggacctg ctgaccgccg agcagggcgg catctgcctg | 1380 |
| gccctgcagg agaagtgctg cttctacgcc aacaagagcg gcatcgtgcg caacaagatc | 1440 |
| cgcaccctgc aggaggagct gcagaagcgc gcgagagcc tggccagcaa ccccctgtgg | 1500 |
| accggcctgc agggcttcct gcctacctg ctgcccctgc tggggccccct gctgaccctg | 1560 |
| ctgctgatcc tgaccatcgg ccccctgcgtg ttcagccgcc tgatggcctt catcaacgac | 1620 |

```
cgcctgaacg tggtgcacgc catggtgctg gcccagcagt accaggccct gaaggccgag      1680
gaggaggccc aggactaa                                                    1698

<210> SEQ ID NO 7
<211> LENGTH: 1698
<212> TYPE: DNA
<213> ORGANISM: Artificial Sequence
<220> FEATURE:
<223> OTHER INFORMATION: RD114 ENV protein codon-optimised variant

<400> SEQUENCE: 7
atgaaacttc ctacgggcat ggtcattctg tgtagtttga taatagtccg ggccgggttt        60
gatgatccta ggaaggccat cgcattggtt cagaaacagc acgggaagcc ctgtgagtgc       120
agtggtgggc aagttagtga agccccgcct aacagcattc agcaagtcac ttgtccgggt       180
aaaactgcat acctgatgac taaccagaaa tggaaatgta gagttactcc taaaaatttg       240
acaccttcag gcggagagct ccaaaactgc ccttgtaata cttttcagga ctctatgcat       300
agctcctgtt acacagagta caggcaatgc agagcgaata caagactta ctatactgcg        360 acccttctga gatccggtc aggctcactc aacgaagtgc aaattctgca gaacccaaac        420
caactgctcc aaagtccatg tcggggcagt atcaatcaac agtatgctg gtcagccacg        480 gcacctattc acatatctga tggcggcgga cccttggaca caaagcgagt ctggaccgtt       540
caaaagcgac ttgagcaaat acacaaagcc atgcatcctg aactccagta tcaccccttg       600
gcattgccaa agtacgggga cgatctcagt cttgatgcaa ggacctttga catacttaac       660
actacattca gactgctcca gatgagtaat ttcagcctcg cacaggactg ttggctttgt       720
ctcaagctgg gcaccccccac cccgctcgcg atcccgacac cgagtctgac atactcactc      780
gccgactcat tggcaaatgc aagttgccag ataatcccgc ccttgctcgt ccagccgatg       840
cagttcagta actcatcctg tctctcaagt ccgttcatta cgacacaga acaaatcgac        900 ttgggcgcag tcaccttcac caactgcaca agtgtggcaa atgtcagtag cccactttgc       960
gccctgaacg ggagcgtatt tctctgtgga ataatatgg cgtacacgta tttgccgcaa       1020
aactggaccg gcctttgtgt tcaagcctca ctcctgccgg atatcgacat aatccctggc       1080
gacgaacctg taccaatccc cgcaatcgac cactacattc acagaccaaa gagagcagtc      1140
cagtttatcc cccttcttgc gggccttggt atcactgctg cattcactac gggcgcaacg      1200
gggcttgggg tatctgtaac acaatataca aagctttctc atcagctcat ttctgacgta      1260
caggtgcttt ctggaactat ccaagatttg caagatcaag tagattccct cgcagaagtg      1320
gtcctccaga accggagggg tctcgatctt ctgactgccg aacaaggggg tatctgcctt      1380
gcactccaag agaaatgctg cttttacgca aacaaaagtg gtattgtacg caacaagata      1440
cgcacgctgc aagaggagct tcagaagcga cgggagagct ggctagtaa ccccctttgg       1500 accggacttc aaggtttctt gcctacctt cttcctcttt tgggcccact cctgactttg       1560
ttgctgattc tcacaatagg tccctgtgtt ttctctcgcc ttatggcttt catcaacgac      1620
aggttgaatg tcgtgcatgc tatggttttg gcacagcaat accaagccct taaagcagaa      1680
gaggaagcac aggactga                                                   1698

<210> SEQ ID NO 8
<211> LENGTH: 1698
<212> TYPE: DNA
<213> ORGANISM: Artificial Sequence
<220> FEATURE:
```

<223> OTHER INFORMATION: Wildtype RD114 ENV protein

<400> SEQUENCE: 8

```
atgaaactcc caacaggaat ggtcatttta tgtagcctaa taatagttcg ggcagggttt      60
gacgaccccc gcaaggctat cgcattagta caaaaacaac atggtaaacc atgcgaatgc     120
agcggagggc aggtatccga ggccccaccg aactccatcc aacaggtaac ttgcccaggc     180
aagacggcct acttaatgac caaccaaaaa tggaaatgca gagtcactcc aaaaaatctc     240
accccctagcg ggggagaact ccagaactgc cctgtaaca ctttccagga ctcgatgcac     300
agttcttgtt atactgaata ccggcaatgc agggcgaata taagacata ctacacggcc     360
accttgctta aaatacggtc tgggagcctc aacgaggtac agatattaca aaaccccaat     420
cagctcctac agtccccttg taggggctct ataaatcagc cgtttgctg gagtgccaca     480
gcccccatcc atatctccga tggtggagga ccctcgata ctaagagagt gtggacagtc     540
caaaaaggc tagaacaaat tcataaggct atgcatcctg aacttcaata ccacccctta     600
gccctgccca agtcagaga tgaccttagc cttgatgcac ggactttga tatcctgaat     660
accactttta ggttactcca gatgtccaat tttagccttg cccaagattt ttggctctgt     720
ttaaaactag gtacccctac ccctcttgcg atacccactc cctctttaac ctactcccta     780
gcagactccc tagcgaatgc ctcctgtcag attatacctc ccctcttggt tcaaccgatg     840
cagttctcca actcgtcctg tttatcttcc cctttcatta acgatacgga acaaatagac     900
ttaggtgcag tcacctttac taactgcacc tctgtagcca atgtcagtag tcctttatgt     960
gccctaaacg ggtcagtctt cctctgtgga aataacatgg catacaccta tttaccccaa    1020
aactggacag actttgcgt ccaagcctcc ctcctccccg acattgacat catcccgggg    1080
gatgagccag tccccattcc tgccattgat cattatatac atagacctaa acgagctgta    1140
cagttcatcc ctttactagc tggactggga atcaccgcag cattcaccac cggagctaca    1200
ggcctaggtg tctccgtcac ccagtataca aaattatccc atcagttaat atctgatgtc    1260
caagtcttat ccggtaccat acaagattta caagaccagg tagactcgtt agctgaagta    1320
gttctccaaa ataggagggg actggaccta ctaacggcag aacaaggagg aatttgttta    1380
gccttacaag aaaaatgctg tttttatgct aacaagtcag gaattgtgag aaacaaaata    1440
agaaccctac aagaagaatt acaaaaacgc agggaaagcc tggcatccaa ccctctctgg    1500
accgggctgc agggctttct tccgtacctc ctacctctcc tgggacccct actcaccctc    1560
ctactcatac taaccattgg gccatgcgtt ttcagtcgcc tcatggcctt cattaatgat    1620
agacttaatg ttgtacatgc catggtgctg gcccagcaat accaagcact caaagctgag    1680
gaagaagctc aggattga                                                  1698
```

<210> SEQ ID NO 9
<211> LENGTH: 2004
<212> TYPE: DNA
<213> ORGANISM: Artificial Sequence
<220> FEATURE:
<223> OTHER INFORMATION: GALV ENV protein codon-optimised variant

<400> SEQUENCE: 9

```
atggtgttgc ttcctgggtc tatgctgctg acatctaatc tccaccatct cagacaccag      60
atgtcacccg gcagttggaa gcggctgatc atactgttga gctgcgtatt cggcggaggg     120
ggcacctctc tccagaacaa aaatcctcat caaccgatga cgcttacgtg gcaggtattg     180
tcccagacgg gtgacgtggt atgggacact aaggctgttc aaccgccttg gacgtggtgg     240
```

```
ccgacgctga agccagatgt ctgtgccctg gcggcgtccc ttgagagctg ggatatcccg      300
gggaccgacg tatcctccag caagagagtt cgccccctg actcagacta cacagccgcc       360
tataagcaaa tcacttgggg cgcgattggg tgttcatatc cccgagcacg caccagaatg      420
gcaagctcta cattctatgt ttgtccccgc gatggccgga cgctgtccga agcgaggcga      480
tgcggaggtc tcgaaagcct ctactgcaag gaatgggact gtgagactac gggcacgggt     540
tattggcttt ctaaatcaag caaagacttg atcactctta gtgggaccga aactcagag      600 tggacacaaa gtttcaaca atgccaccag actggatggt gcaaccccct gaagatagac      660
tttactgaca aggtaagct gagcaaggac tggataacag gaaaacttg ggggttgcgc        720 ttttatgtct caggccatcc gggggtacaa tttacgattc gcctcaaaat cacgaacatg     780
ccggcggtcg ctgtaggtcc ggacttggtt ttggtagaac aaggccctcc tcggactagc     840
ctcgcactgc ctccccccact cccgcctcga gaggcaccac cgccgagcct gccggattcc     900
aattcaacgg ctctggccac ctccgcacaa acaccaacag tgcggaagac tatcgtgacc      960
ctcaacactc cgcccccgac cacgggcgac agattgtttg acctggttca aggggccttc     1020
ttgacgctca atgcaacgaa ccctggagca acagagtctt gttggctttg tctggccatg     1080
ggtccccctt attatgaagc catcgcgtca tctggtgaag tggcttactc aaccgacctc     1140
gatcgctgta ggtggggcac gcaaggaaag cttactttga ccgaggtctc aggtcatggg     1200
ttgtgcattg gaaggtcccc cttacacac caacatcttt gtaaccagac tctgagtata     1260
aattcttctg gagatcatca gtatttgctg ccgagtaacc attcatggtg ggcgtgctcc     1320
acgggactca cccttgcct ttcaacttcc gtttttaatc aaacgagaga tttctgtatc     1380
caagtgcaac tcattccgag gatctactac tatccggaag aagtactcct gcaggcgtat     1440
gacaattccc accctaggac caaacgcgaa gcagtgagcc tgaccccttgc agtattgttg    1500 ggtttgggga ttactgcggg tatcggcact ggttccaccg cgctgattaa gggaccgatc     1560
gatttgcaac aaggattgac ttcactccag atagccatag acgccgacct tcgcgcgttg    1620
caggattctg tgtctaagct ggaggatagt ttgacaagcc tctcagaggt ggtgctgcaa     1680
aacagacgag gccttgatct cttgtttctt aaggagggag gcctttgcgc tgctctgaag     1740
gaagagtgtt gtttctacat cgatcatagc ggagcggtca gagattctat gaagaagctt     1800
aaggagaagc ttgacaagcg acagctcgaa cgccaaaaga gccagaattg gtacgaagga     1860
tggtttaata attctccatg gttcactaca ctgctttcca ccatcgctgg tccgctgctg     1920
ctcctgctgc tcctgttgat actcggtccg tgcataatta taagctcgt tcaattcata     1980 aacgaccgga tctctgcgtg ctaa                                             2004
```

<210> SEQ ID NO 10
<211> LENGTH: 2004
<212> TYPE: DNA
<213> ORGANISM: Artificial Sequence
<220> FEATURE:
<223> OTHER INFORMATION: GALV ENV protein codon-optimised variant

<400> SEQUENCE: 10

```
atggtgcttc tccctggtag catgcttttg acctcaaacc tccatcatct gcgacaccag       60
atgtcacctg gctcttggaa acgccttatt atattgctga gctgtgtttt tggaggcgga      120
ggtacatcat tgcagaacaa aaaccctcat cagccaatga cgttgacctg gcaagtattg      180
tcccagaccg gagatgtcgt ttgggacacg aaagcggtac aacctccctg gacttggtgg     240
```

```
ccgaccctca agcccgacgt tgcgctctt gcggcgtctt tggagtcttg ggacataccg      300
gggacggatg tctcatcttc aaagagggtt cgaccgccgg attcagacta caccgctgca      360
tataagcaga ttacgtgggg agccattggc tgtagttatc cgcgggcgag gacgcggatg      420
gcttccagta ctttttatgt gtgtccgaga cggccgca ccctgtctga ggctcggcgc      480 tgcgggggc tcgaaagcct gtactgcaaa gaatgggatt gtgagactac agggactggt      540
tattggctct caaaatctag caaagatctg attacgctca aatgggatca aaattcagaa      600
tggacccaaa agttccagca atgtcatcag accgggtggt gtaatccgct gaagatagac      660
tttacagaca aaggcaaact gtcaaaagac tggattacgg gtaagacttg gggcctccgc      720
ttttacgtaa gcggtcatcc tggggtacag tttactataa ggctgaaaat aacgaacatg      780
ccggcggtcg ctgtcgggcc ggatttggtg ctcgtggaac aagggccacc taggacctct      840
ctcgctcttc ccccgccatt gccaccacgg gaagcaccgc caccaagtct tccagattcc      900
aactctaccg cactggctac gagtgcgcag acaccaacgg ttagaaaaac cattgtcacg      960
cttaacaccc ccctccgac aaccgagat cgccttttcg atctcgtaca gggcgcgttt     1020
cttacgctta acgccacaaa tcctggggcc actgagagct gttggctttg ccttgctatg     1080
ggcccaccat actatgaggc catcgcctcc tccggcgaag tagcctactc cacggacctt     1140
gaccgatgca ggtggggaac gcaaggcaaa ttgactttga ctgaggtgag cgggcatggt     1200
ctctgcatcg gaaaagttcc gttcactcat cagcaccttt gtaaccagac cctcagcatt     1260
aattcttccg gggatcatca gtacctcctg ccgtcaaacc actcttggtg ggcctgctcc     1320
acaggtctta ctccctgctt gagcacatcc gtatttaatc agacccgaga cttctgtatc     1380
caggtacaat tgataccgag aatttattac taccccgagg aagtgttgct ccaagcatac     1440
gataactcac accctagaac gaagagagaa gcagtctccc tgacgttggc cgtccttctg     1500
ggactgggaa tcaccgcggg tataggcact ggatctacgg cactgatcaa ggggcctata     1560
gatttgcagc aggggcttac ttcacttcaa attgccatag acgcggatct tcgggcgctc     1620
caggactccg tttccaagtt ggaagactct ctgactagcc tgtccgaagt tgtgttgcag     1680
aacagacgag gacttgactt gttgtttctc aaggaagggg gtctctgtgc tgcgcttaag     1740
gaggaatgtt gcttctatat agatcattcc ggcgcggtac gggactccat gaaaaaactt     1800
aaagaaaagt tggacaagag acagttggag aggcaaaagt cccagaactg gtatgagggc     1860
tggtttaata actcccccatg gtttacaacc cttttgtcta ccattgctgg gccgctcctt     1920
cttcttctgt tgctgctcat attggggcct tgtattatta caagcttgt gcaattcatt     1980 aatgaccgaa tttctgcatg ctaa                                           2004

<210> SEQ ID NO 11
<211> LENGTH: 2004
<212> TYPE: DNA
<213> ORGANISM: Artificial Sequence
<220> FEATURE:
<223> OTHER INFORMATION: GALV ENV protein codon-optimised variant

<400> SEQUENCE: 11
atggtgctgc tgcccggcag catgctgctg accagcaacc tgcaccacct gcgccaccag       60
atgagccccg gcagctggaa cgcctgatc atcctgctga gctgcgtgtt cggcggcggc      120
ggcaccagcc tgcagaacaa gaaccccac cagcccatga ccctgacctg caggtgctg      180 agccagaccg gcgacgtggt gtgggacacc aaggccgtgc agccccctg acctggtgg      240 cccacccctga agcccgacgt gtgcgccctg gccgccagcc tggagagctg ggacatcccc      300
```

-continued

```
ggcaccgacg tgagcagcag caagcgcgtg cgcccccccg acagcgacta caccgccgcc    360
tacaagcaga tcacctgggg cgccatcggc tgcagctacc cccgcgcccg cacccgcatg    420
gccagcagca ccttctacgt gtgcccccgc gacggccgca ccctgagcga ggcccgccgc    480
tgcggcggcc tggagagcct gtactgcaag gagtgggact gcgagaccac cggcaccggc    540
tactggctga gcaagagcag caaggacctg atcaccctga agtgggacca gaacagcgag    600
tggacccaga agttccagca gtgccaccag accggctggt gcaacccccct gaagatcgac    660 ttcaccgaca agggcaagct gagcaaggac tggatcaccg gcaagacctg gggcctgcgc    720
ttctacgtga gcggccaccc cggcgtgcag ttcaccatcc gcctgaagat caccaacatg    780
cccgccgtgg ccgtgggccc cgacctggtg ctggtggagc agggcccccc ccgcaccagc    840
ctggccctgc ccccccccct gccccccccgc gaggcccccc cccccagcct gcccgacagc    900
aacagcaccg ccctggccac cagcgcccag acccccaccg tgcgcaagac catcgtgacc    960
ctgaacaccc cccccccccac caccggcgac cgcctgttcg acctggtgca gggcgccttc   1020
ctgaccctga acgccaccaa ccccggcgcc accgagagct gctggctgtg cctggccatg   1080 ggcccccccct actacgaggc catcgccagc agcggcgagg tggcctacag caccgacctg   1140
gaccgctgcc gctggggcac ccagggcaag ctgaccctga ccgaggtgag cggccacggc   1200
ctgtgcatcg gcaaggtgcc cttcacccac cagcacctgt gcaaccagac cctgagcatc   1260
aacagcagcg gcgaccacca gtacctgctg cccagcaacc acagctggtg ggcctgcagc   1320
accggcctga cccccctgcct gagcaccagc gtgttcaacc agacccgcga cttctgcatc   1380
caggtgcagc tgatcccccg catctactac taccccgagg aggtgctgct gcaggcctac   1440
gacaacagcc acccccgcac caagcgcgag gccgtgagcc tgaccctggc cgtgctgctg   1500
ggcctgggca tcaccgccgg catcggcacc ggcagcaccg ccctgatcaa gggccccatc   1560
gacctgcagc agggcctgac cagcctgcag atcgccatcg acgccgacct gcgcgccctg   1620
caggacagcg tgagcaagct ggaggacagc ctgaccagcc tgagcgaggt ggtgctgcag   1680
aaccgccgcg gcctggacct gctgttcctg aaggagggcg gcctgtgcgc cgccctgaag   1740
gaggagtgct gcttctacat cgaccacagc ggcgccgtgc gcgacagcat gaagaagctg   1800
aaggagaagc tggacaagcg ccagctggag cgccagaaga gccagaactg gtacgagggc   1860
tggttcaaca acagcccctg gttcaccacc ctgctgagca ccatcgccgg cccccctgctg   1920 ctgctgctgc tgctgctgat cctgggcccc tgcatcatca acaagctggt gcagttcatc   1980
aacgaccgca tcagcgcctg ctaa                                           2004
```

<210> SEQ ID NO 12
<211> LENGTH: 2004
<212> TYPE: DNA
<213> ORGANISM: Artificial Sequence
<220> FEATURE:
<223> OTHER INFORMATION: Wild type GALV ENV protein

<400> SEQUENCE: 12

```
atggtattgc tgcctgggtc catgcttctc acctcaaacc tgcaccacct tcggcaccag     60
atgagtcctg ggagctggaa aagactgatc atcctcctaa gctgcgtatt cggcggcggc    120
ggtaccagtc tgcaaaataa gaacccccac cagcccatga ccctcacttg gcaggtactg    180
tcccaaactg gagacgttgt ctgggataca aaggcagtcc agccccccttg gacttggtgg    240 cccacactta aacctgatgt atgtgccttg gcggctagtc ttgagtcctg ggatatcccg    300
```

-continued

```
ggaaccgatg tctcgtcctc taaacgagtc agacctccgg actcagacta tactgccgct    360
tataagcaaa tcacctgggg agccataggg tgcagctacc ctcgggctag gactagaatg    420
gcaagctcta ccttctacgt atgtccccgg gatggccgga ccctttcaga agctagaagg    480 tgcgggggc tagaatccct atactgtaaa gaatgggatt gtgagaccac ggggaccggt     540
tattggctat ctaaatcctc aaaagacctc ataactctta agtgggacca aaatagcgaa    600
tggactcaaa aatttcaaca gtgtcaccag accggctggt gtaacccct taaaatagat     660 ttcacagaca aaggaaaatt atccaaggac tggataacgg gaaaaacctg gggattaaga    720
ttctatgtgt ctggacatcc aggcgtacag ttcaccattc gcttaaaaat caccaacatg    780
ccagctgtgg cagtaggtcc tgacctcgtc cttgtggaac aaggacctcc tagaacgtcc    840
ctcgctctcc cacctcctct tcccccaagg gaagcgccac cgccatctct ccccgactct    900
aactccacag ccctggcgac tagtgcacaa actcccacgg tgagaaaaac aattgttacc    960
ctaaacactc cgcctcccac cacaggcgag agacttttg atcttgtgca gggggccttc    1020
ctaaccttaa atgctaccaa cccaggggcc actgagtctt gctggctttg tttggccatg    1080
ggcccccctt attatgaagc aatagcctca tcaggagagg tcgcctactc caccgacctt    1140
gaccggtgcc gctgggggac ccaaggaaag ctcaccctca ctgaggtctc aggacacggg    1200
ttgtgcatag aaaggtgcc ctttacccat cagcatctct gcaatcagac cctatccatc     1260
aattcctccg gagaccatca gtatctgctc ccctccaacc atagctggtg ggcttgcagc    1320
actggcctca cccccttgcct ctccacctca gttttaatc agactagaga tttctgtatc    1380
caggtccagc tgattcctcg catctattac tatcctgaag aagttttgtt acaggcctat    1440
gacaattctc accccaggac taaaagagag gctgtctcac ttaccctagc tgttttactg    1500
gggttgggaa tcacggcggg aataggtact ggttcaactg ccttaattaa aggacctata    1560
gacctccagc aaggcctgac aagcctccag atcgccatag atgctgacct ccgggccctc    1620
caagactcag tcagcaagtt agaggactca ctgacttccc tgtccgaggt agtgctccaa    1680
aataggagag gccttgactt gctgtttcta aaagaaggtg gcctctgtgc ggccctaaag    1740
gaagagtgct gtttttacat agaccactca ggtgcagtac gggactccat gaaaaaactc    1800
aaagaaaaac tggataaaag acagttagag cgccagaaaa gccaaactg gtatgaagga    1860 tggttcaata actccccttg gttcactacc ctgctatcaa ccatcgctgg gccctatta     1920 ctcctccttc tgttgctcat cctcgggcca tgcatcatca ataagttagt tcaattcatc    1980
aatgatagga taagtgcatg ttaa                                          2004
```

<210> SEQ ID NO 13
<211> LENGTH: 538
<212> TYPE: PRT
<213> ORGANISM: Artificial Sequence
<220> FEATURE:
<223> OTHER INFORMATION: Gag Polyprotein Amino Acid Sequence

<400> SEQUENCE: 13

```
Met Gly Gln Thr Val Thr Thr Pro Leu Ser Leu Thr Leu Gly His Trp
1               5                   10                  15

Lys Asp Val Glu Arg Ile Ala His Asn Gln Ser Val Asp Val Lys Lys
            20                  25                  30

Arg Arg Trp Val Thr Phe Cys Ser Ala Glu Trp Pro Thr Phe Asn Val
        35                  40                  45

Gly Trp Pro Arg Asp Gly Thr Phe Asn Arg Asp Leu Ile Thr Gln Val
    50                  55                  60
```

```
Lys Ile Lys Val Phe Ser Pro Gly His Gly His Pro Asp Gln Val
 65                  70                  75                  80

Pro Tyr Ile Val Thr Trp Glu Ala Leu Ala Phe Asp Pro Pro Trp
                 85                  90                  95

Val Lys Pro Phe Val His Pro Lys Pro Pro Pro Leu Pro Pro Ser
                100                 105                 110

Ala Pro Ser Leu Pro Leu Glu Pro Pro Arg Ser Thr Pro Arg Ser
                115                 120                 125

Ser Leu Tyr Pro Ala Leu Thr Pro Ser Leu Gly Ala Lys Pro Lys Pro
130                 135                 140

Gln Val Leu Ser Asp Ser Gly Gly Pro Leu Ile Asp Leu Leu Thr Glu
145                 150                 155                 160

Asp Pro Pro Pro Tyr Arg Asp Pro Arg Pro Pro Pro Ser Asp Arg Asp
                    165                 170                 175

Gly Asn Gly Gly Glu Ala Thr Pro Ala Gly Glu Ala Pro Asp Pro Ser
                180                 185                 190

Pro Met Ala Ser Arg Leu Arg Gly Arg Arg Glu Pro Pro Val Ala Asp
                195                 200                 205

Ser Thr Thr Ser Gln Ala Phe Pro Leu Arg Ala Gly Gly Asn Gly Gln
210                 215                 220

Leu Gln Tyr Trp Pro Phe Ser Ser Ser Asp Leu Tyr Asn Trp Lys Asn
225                 230                 235                 240

Asn Asn Pro Ser Phe Ser Glu Asp Pro Gly Lys Leu Thr Ala Leu Ile
                    245                 250                 255

Glu Ser Val Leu Ile Thr His Gln Pro Thr Trp Asp Asp Cys Gln Gln
                260                 265                 270

Leu Leu Gly Thr Leu Leu Thr Gly Glu Glu Lys Gln Arg Val Leu Leu
                275                 280                 285

Glu Ala Arg Lys Ala Val Arg Gly Asp Asp Gly Arg Pro Thr Gln Leu
290                 295                 300

Pro Asn Glu Val Asp Ala Ala Phe Pro Leu Glu Arg Pro Asp Trp Asp
305                 310                 315                 320

Tyr Thr Thr Gln Ala Gly Arg Asn His Leu Val His Tyr Arg Gln Leu
                    325                 330                 335

Leu Leu Ala Gly Leu Gln Asn Ala Gly Arg Ser Pro Thr Asn Leu Ala
                340                 345                 350

Lys Val Lys Gly Ile Thr Gln Gly Pro Asn Glu Ser Pro Ser Ala Phe
                355                 360                 365

Leu Glu Arg Leu Lys Glu Ala Tyr Arg Arg Tyr Thr Pro Tyr Asp Pro
                370                 375                 380

Glu Asp Pro Gly Gln Glu Thr Asn Val Ser Met Ser Phe Ile Trp Gln
385                 390                 395                 400

Ser Ala Pro Asp Ile Gly Arg Lys Leu Glu Arg Leu Glu Asp Leu Lys
                    405                 410                 415

Asn Lys Thr Leu Gly Asp Leu Val Arg Glu Ala Glu Lys Ile Phe Asn
                420                 425                 430

Lys Arg Glu Thr Pro Glu Glu Arg Glu Glu Arg Ile Arg Arg Glu Thr
                435                 440                 445

Glu Glu Lys Glu Glu Arg Arg Arg Thr Glu Asp Glu Gln Lys Glu Lys
                450                 455                 460

Glu Arg Asp Arg Arg Arg His Arg Glu Met Ser Lys Leu Leu Ala Thr
465                 470                 475                 480
```

-continued

```
Val Val Ser Gly Gln Lys Gln Asp Arg Gln Gly Gly Glu Arg Arg Arg
                485                 490                 495

Ser Gln Leu Asp Arg Asp Gln Cys Ala Tyr Cys Lys Glu Lys Gly His
        500                 505                 510

Trp Ala Lys Asp Cys Pro Lys Lys Pro Arg Gly Pro Arg Gly Pro Arg
        515                 520                 525

Pro Gln Thr Ser Leu Leu Thr Leu Asp Asp
        530                 535

<210> SEQ ID NO 14
<211> LENGTH: 1090
<212> TYPE: PRT
<213> ORGANISM: Artificial Sequence
<220> FEATURE:
<223> OTHER INFORMATION: Pol Polyprotein Amino Acid Sequence

<400> SEQUENCE: 14

Met Gly Pro Met Gly Gln Pro Leu Gln Val Leu Thr Leu Asn Ile Glu
1               5                   10                  15

Asp Glu Tyr Arg Leu His Glu Thr Ser Lys Glu Pro Asp Val Ser Leu
            20                  25                  30

Gly Ser Thr Trp Leu Ser Asp Phe Pro Gln Ala Trp Ala Glu Thr Gly
        35                  40                  45

Gly Met Gly Leu Ala Val Arg Gln Ala Pro Leu Ile Ile Pro Leu Lys
    50                  55                  60

Ala Thr Ser Thr Pro Val Ser Ile Lys Gln Tyr Pro Met Ser Gln Glu
65                  70                  75                  80

Ala Arg Leu Gly Ile Lys Pro His Ile Gln Arg Leu Leu Asp Gln Gly
                85                  90                  95

Ile Leu Val Pro Cys Gln Ser Pro Trp Asn Thr Pro Leu Leu Pro Val
            100                 105                 110

Lys Lys Pro Gly Thr Asn Asp Tyr Arg Pro Val Gln Asp Leu Arg Glu
        115                 120                 125

Val Asn Lys Arg Val Glu Asp Ile His Pro Thr Val Pro Asn Pro Tyr
    130                 135                 140

Asn Leu Leu Ser Gly Leu Pro Pro Ser His Gln Trp Tyr Thr Val Leu
145                 150                 155                 160

Asp Leu Lys Asp Ala Phe Phe Cys Leu Arg Leu His Pro Thr Ser Gln
                165                 170                 175

Pro Leu Phe Ala Phe Glu Trp Arg Asp Pro Glu Met Gly Ile Ser Gly
            180                 185                 190

Gln Leu Thr Trp Thr Arg Leu Pro Gln Gly Phe Lys Asn Ser Pro Thr
        195                 200                 205

Leu Phe Asp Glu Ala Leu His Arg Asp Leu Ala Asp Phe Arg Ile Gln
    210                 215                 220

His Pro Asp Leu Ile Leu Leu Gln Tyr Val Asp Asp Leu Leu Leu Ala
225                 230                 235                 240

Ala Thr Ser Glu Leu Asp Cys Gln Gln Gly Thr Arg Ala Leu Leu Gln
                245                 250                 255

Thr Leu Gly Asn Leu Gly Tyr Arg Ala Ser Ala Lys Lys Ala Gln Ile
            260                 265                 270

Cys Gln Lys Gln Val Lys Tyr Leu Gly Tyr Leu Leu Lys Glu Gly Gln
        275                 280                 285

Arg Trp Leu Thr Glu Ala Arg Lys Glu Thr Val Met Gly Gln Pro Thr
    290                 295                 300
```

```
Pro Lys Thr Pro Arg Gln Leu Arg Glu Phe Leu Gly Thr Ala Gly Phe
305                 310                 315                 320

Cys Arg Leu Trp Ile Pro Gly Phe Ala Glu Met Ala Ala Pro Leu Tyr
            325                 330                 335

Pro Leu Thr Lys Thr Gly Thr Leu Phe Asn Trp Gly Pro Asp Gln Gln
        340                 345                 350

Lys Ala Tyr Gln Glu Ile Lys Gln Ala Leu Leu Thr Ala Pro Ala Leu
            355                 360                 365

Gly Leu Pro Asp Leu Thr Lys Pro Phe Glu Leu Phe Val Asp Glu Lys
    370                 375                 380

Gln Gly Tyr Ala Lys Gly Val Leu Thr Gln Lys Leu Gly Pro Trp Arg
385                 390                 395                 400

Arg Pro Val Ala Tyr Leu Ser Lys Lys Leu Asp Pro Val Ala Ala Gly
                405                 410                 415

Trp Pro Pro Cys Leu Arg Met Val Ala Ala Ile Ala Val Leu Thr Lys
            420                 425                 430

Asp Ala Gly Lys Leu Thr Met Gly Gln Pro Leu Val Ile Leu Ala Pro
            435                 440                 445

His Ala Val Glu Ala Leu Val Lys Gln Pro Pro Asp Arg Trp Leu Ser
450                 455                 460

Asn Ala Arg Met Thr His Tyr Gln Ala Leu Leu Leu Asp Thr Asp Arg
465                 470                 475                 480

Val Gln Phe Gly Pro Val Val Ala Leu Asn Pro Ala Thr Leu Leu Pro
                485                 490                 495

Leu Pro Glu Glu Gly Leu Gln His Asp Cys Leu Asp Ile Leu Ala Glu
            500                 505                 510

Ala His Gly Thr Arg Ser Asp Leu Thr Asp Gln Pro Leu Pro Asp Ala
        515                 520                 525

Asp His Thr Trp Tyr Thr Asp Gly Ser Ser Phe Leu Gln Glu Gly Gln
    530                 535                 540

Arg Lys Ala Gly Ala Ala Val Thr Thr Glu Thr Glu Val Ile Trp Ala
545                 550                 555                 560

Arg Ala Leu Pro Ala Gly Thr Ser Ala Gln Arg Ala Glu Leu Ile Ala
                565                 570                 575

Leu Thr Gln Ala Leu Lys Met Ala Glu Gly Lys Lys Leu Asn Val Tyr
            580                 585                 590

Thr Asp Ser Arg Tyr Ala Phe Ala Thr Ala His Ile His Gly Glu Ile
        595                 600                 605

Tyr Arg Arg Arg Gly Leu Leu Thr Ser Glu Gly Lys Glu Ile Lys Asn
    610                 615                 620

Lys Asp Glu Ile Leu Ala Leu Leu Lys Ala Leu Phe Leu Pro Lys Arg
625                 630                 635                 640

Leu Ser Ile Ile His Cys Pro Gly His Gln Lys Gly Asn Ser Ala Glu
                645                 650                 655

Ala Arg Gly Asn Arg Met Ala Asp Gln Ala Ala Arg Glu Val Ala Thr
            660                 665                 670

Arg Glu Thr Pro Gly Thr Ser Thr Leu Leu Ile Glu Asn Ser Thr Pro
        675                 680                 685

Tyr Thr His Glu His Phe His Tyr Thr Val Thr Asp Thr Lys Asp Leu
    690                 695                 700

Thr Lys Leu Gly Ala Thr Tyr Asp Ser Ala Lys Lys Tyr Trp Val Tyr
705                 710                 715                 720

Gln Gly Lys Pro Val Met Pro Asp Gln Phe Thr Phe Glu Leu Leu Asp
```

```
                        725                 730                 735
Phe Leu His Gln Leu Thr His Leu Ser Phe Ser Lys Thr Lys Ala Leu
                    740                 745                 750
Leu Glu Arg Ser Pro Ser Pro Tyr Tyr Met Leu Asn Arg Asp Arg Thr
                755                 760                 765
Leu Lys Asn Ile Thr Glu Thr Cys Lys Ala Cys Ala Gln Val Asn Ala
            770                 775                 780
Ser Lys Ser Ala Val Lys Gln Gly Thr Arg Val Arg Gly His Arg Pro
785                 790                 795                 800
Gly Thr His Trp Glu Ile Asp Phe Thr Glu Val Lys Pro Gly Leu Tyr
                805                 810                 815
Gly Tyr Lys Tyr Leu Leu Val Phe Val Asp Thr Phe Ser Gly Trp Ile
                820                 825                 830
Glu Ala Phe Pro Thr Lys Lys Glu Thr Ala Lys Val Val Thr Lys Lys
                835                 840                 845
Leu Leu Glu Glu Ile Phe Pro Arg Phe Gly Met Pro Gln Val Leu Gly
                850                 855                 860
Thr Asp Asn Gly Pro Ala Phe Val Ser Lys Val Ser Gln Thr Val Ala
865                 870                 875                 880
Asp Leu Leu Gly Ile Asp Trp Lys Leu His Cys Ala Tyr Arg Pro Gln
                885                 890                 895
Ser Ser Gly Gln Val Glu Arg Met Asn Arg Thr Ile Lys Glu Thr Leu
                900                 905                 910
Thr Lys Leu Thr Leu Ala Thr Gly Ser Arg Asp Trp Val Leu Leu Leu
                915                 920                 925
Pro Leu Ala Leu Tyr Arg Ala Arg Asn Thr Pro Gly Pro His Gly Leu
                930                 935                 940
Thr Pro Tyr Glu Ile Leu Tyr Gly Ala Pro Pro Pro Leu Val Asn Phe
945                 950                 955                 960
Pro Asp Pro Asp Met Thr Arg Val Thr Asn Ser Pro Ser Leu Gln Ala
                965                 970                 975
His Leu Gln Ala Leu Tyr Leu Val Gln His Glu Val Trp Arg Pro Leu
                980                 985                 990
Ala Ala Ala Tyr Gln Glu Gln Leu Asp Arg Pro Val Val Pro His Pro
                995                 1000                1005
Tyr Arg Val Gly Asp Thr Val Trp Val Arg Arg His Gln Thr Lys
                1010                1015                1020
Asn Leu Glu Pro Arg Trp Lys Gly Pro Tyr Thr Val Leu Leu Thr
                1025                1030                1035
Thr Pro Thr Ala Leu Lys Val Asp Gly Ile Ala Ala Trp Ile His
                1040                1045                1050
Ala Ala His Val Lys Ala Ala Asp Thr Glu Ser Gly Pro Ser Ser
                1055                1060                1065
Gly Arg Thr Trp Arg Val Gln Arg Ser Gln Asn Pro Leu Lys Ile
                1070                1075                1080
Arg Leu Thr Arg Gly Ser Pro
                1085                1090

<210> SEQ ID NO 15
<211> LENGTH: 565
<212> TYPE: PRT
<213> ORGANISM: Artificial Sequence
<220> FEATURE:
<223> OTHER INFORMATION: RD114 Envelope Amino Acid Sequence
```

```
<400> SEQUENCE: 15

Met Lys Leu Pro Thr Gly Met Val Ile Leu Cys Ser Leu Ile Ile Val
1               5                   10                  15

Arg Ala Gly Phe Asp Asp Pro Arg Lys Ala Ile Ala Ile Val Gln Lys
            20                  25                  30

Gln His Gly Lys Pro Cys Glu Cys Ser Gly Gly Gln Val Ser Glu Ala
        35                  40                  45

Pro Pro Asn Ser Ile Gln Gln Val Thr Cys Pro Gly Lys Thr Ala Tyr
    50                  55                  60

Leu Met Thr Asn Gln Lys Trp Lys Cys Arg Val Thr Pro Lys Asn Leu
65                  70                  75                  80

Thr Pro Ser Gly Gly Glu Leu Gln Asn Cys Pro Cys Asn Thr Phe Gln
                85                  90                  95

Asp Ser Met His Ser Ser Cys Tyr Thr Glu Tyr Arg Gln Cys Arg Ala
            100                 105                 110

Asn Asn Lys Thr Tyr Tyr Thr Ala Thr Leu Leu Lys Ile Arg Ser Gly
        115                 120                 125

Ser Leu Asn Glu Val Gln Ile Leu Gln Asn Pro Asn Gln Leu Leu Gln
    130                 135                 140

Ser Pro Cys Arg Gly Ser Ile Asn Gln Pro Val Cys Trp Ser Ala Thr
145                 150                 155                 160

Ala Pro Ile His Ile Ser Asp Gly Gly Pro Leu Asp Thr Lys Arg
                165                 170                 175

Val Trp Thr Val Gln Lys Arg Leu Glu Gln Ile His Lys Ala Met His
                180                 185                 190

Pro Glu Leu Gln Tyr His Pro Leu Ala Leu Pro Lys Val Arg Asp Asp
            195                 200                 205

Leu Ser Leu Asp Ala Arg Thr Phe Asp Ile Leu Asn Thr Thr Phe Arg
210                 215                 220

Leu Leu Gln Met Ser Asn Phe Ser Leu Ala Gln Asp Cys Trp Leu Cys
225                 230                 235                 240

Leu Lys Leu Gly Thr Pro Thr Pro Leu Ala Ile Pro Thr Pro Ser Leu
                245                 250                 255

Thr Tyr Ser Leu Ala Asp Ser Leu Ala Asn Ala Ser Cys Gln Ile Ile
                260                 265                 270

Pro Pro Leu Leu Val Gln Pro Met Gln Phe Ser Asn Ser Ser Cys Leu
            275                 280                 285

Ser Ser Pro Phe Ile Asn Asp Thr Glu Gln Ile Asp Leu Gly Ala Val
    290                 295                 300

Thr Phe Thr Asn Cys Thr Ser Val Ala Asn Val Ser Ser Pro Leu Cys
305                 310                 315                 320

Ala Leu Asn Gly Ser Val Phe Leu Cys Gly Asn Asn Met Ala Tyr Thr
                325                 330                 335

Tyr Leu Pro Gln Asn Trp Thr Gly Leu Cys Val Gln Ala Ser Leu Leu
            340                 345                 350

Pro Asp Ile Asp Ile Ile Pro Gly Asp Glu Pro Val Pro Ile Pro Ala
        355                 360                 365

Ile Asp His Tyr Ile His Arg Pro Lys Arg Ala Val Gln Phe Ile Pro
    370                 375                 380

Leu Leu Ala Gly Leu Gly Ile Thr Ala Ala Phe Thr Thr Gly Ala Thr
385                 390                 395                 400

Gly Leu Gly Val Ser Val Thr Gln Tyr Thr Lys Leu Ser His Gln Leu
                405                 410                 415
```

```
Ile Ser Asp Val Gln Val Leu Ser Gly Thr Ile Gln Asp Leu Gln Asp
            420                 425                 430

Gln Val Asp Ser Leu Ala Glu Val Leu Gln Asn Arg Arg Gly Leu
                435                 440                 445

Asp Leu Leu Thr Ala Glu Gln Gly Gly Ile Cys Leu Ala Leu Gln Glu
        450                 455                 460

Lys Cys Cys Phe Tyr Ala Asn Lys Ser Gly Ile Val Arg Asn Lys Ile
465                 470                 475                 480

Arg Thr Leu Gln Glu Glu Leu Gln Lys Arg Arg Glu Ser Leu Ala Ser
                485                 490                 495

Asn Pro Leu Trp Thr Gly Leu Gln Gly Phe Leu Pro Tyr Leu Leu Pro
                500                 505                 510

Leu Leu Gly Pro Leu Leu Thr Leu Leu Leu Ile Leu Thr Ile Gly Pro
            515                 520                 525

Cys Val Phe Ser Arg Leu Met Ala Phe Ile Asn Asp Arg Leu Asn Val
        530                 535                 540

Val His Ala Met Val Leu Ala Gln Gln Tyr Gln Ala Leu Lys Ala Glu
545                 550                 555                 560

Glu Glu Ala Gln Asp
                565

<210> SEQ ID NO 16
<211> LENGTH: 667
<212> TYPE: PRT
<213> ORGANISM: Artificial Sequence
<220> FEATURE:
<223> OTHER INFORMATION: Galv Envelope Amino Acid Sequence

<400> SEQUENCE: 16

Met Val Leu Leu Pro Gly Ser Met Leu Leu Thr Ser Asn Leu His His
1               5                   10                  15

Leu Arg His Gln Met Ser Pro Gly Ser Trp Lys Arg Leu Ile Ile Leu
                20                  25                  30

Leu Ser Cys Val Phe Gly Gly Gly Gly Thr Ser Leu Gln Asn Lys Asn
            35                  40                  45

Pro His Gln Pro Met Thr Leu Thr Trp Gln Val Leu Ser Gln Thr Gly
        50                  55                  60

Asp Val Val Trp Asp Thr Lys Ala Val Gln Pro Pro Trp Thr Trp Trp
65                  70                  75                  80

Pro Thr Leu Lys Pro Asp Val Cys Ala Leu Ala Ala Ser Leu Glu Ser
                85                  90                  95

Trp Asp Ile Pro Gly Thr Asp Val Ser Ser Ser Lys Arg Val Arg Pro
                100                 105                 110

Pro Asp Ser Asp Tyr Thr Ala Ala Tyr Lys Gln Ile Thr Trp Gly Ala
            115                 120                 125

Ile Gly Cys Ser Tyr Pro Arg Ala Arg Thr Arg Met Ala Ser Ser Thr
        130                 135                 140

Phe Tyr Val Cys Pro Arg Asp Gly Arg Thr Leu Ser Glu Ala Arg Arg
145                 150                 155                 160

Cys Gly Gly Leu Glu Ser Leu Tyr Cys Lys Glu Trp Asp Cys Glu Thr
                165                 170                 175

Thr Gly Thr Gly Tyr Trp Leu Ser Lys Ser Ser Lys Asp Leu Ile Thr
            180                 185                 190

Leu Lys Trp Asp Gln Asn Ser Glu Trp Thr Gln Lys Phe Gln Gln Cys
        195                 200                 205
```

-continued

```
His Gln Thr Gly Trp Cys Asn Pro Leu Lys Ile Asp Phe Thr Asp Lys
    210                 215                 220
Gly Lys Leu Ser Lys Asp Trp Ile Thr Gly Lys Thr Trp Gly Leu Arg
225                 230                 235                 240
Phe Tyr Val Ser Gly His Pro Gly Val Gln Phe Thr Ile Arg Leu Lys
                245                 250                 255
Ile Thr Asn Met Pro Ala Val Ala Val Gly Pro Asp Leu Val Leu Val
            260                 265                 270
Glu Gln Gly Pro Pro Arg Thr Ser Leu Ala Leu Pro Pro Pro Leu Pro
        275                 280                 285
Pro Arg Glu Ala Pro Pro Ser Leu Pro Asp Ser Asn Ser Thr Ala
    290                 295                 300
Leu Ala Thr Ser Ala Gln Thr Pro Thr Val Arg Lys Thr Ile Val Thr
305                 310                 315                 320
Leu Asn Thr Pro Pro Thr Thr Gly Asp Arg Leu Phe Asp Leu Val
                325                 330                 335
Gln Gly Ala Phe Leu Thr Leu Asn Ala Thr Asn Pro Gly Ala Thr Glu
                340                 345                 350
Ser Cys Trp Leu Cys Leu Ala Met Gly Pro Pro Tyr Tyr Glu Ala Ile
            355                 360                 365
Ala Ser Ser Gly Glu Val Ala Tyr Ser Thr Asp Leu Asp Arg Cys Arg
370                 375                 380
Trp Gly Thr Gln Gly Lys Leu Thr Leu Thr Glu Val Ser Gly His Gly
385                 390                 395                 400
Leu Cys Ile Gly Lys Val Pro Phe Thr His Gln His Leu Cys Asn Gln
                405                 410                 415
Thr Leu Ser Ile Asn Ser Ser Gly Asp His Gln Tyr Leu Leu Pro Ser
            420                 425                 430
Asn His Ser Trp Trp Ala Cys Ser Thr Gly Leu Thr Pro Cys Leu Ser
        435                 440                 445
Thr Ser Val Phe Asn Gln Thr Arg Asp Phe Cys Ile Gln Val Gln Leu
    450                 455                 460
Ile Pro Arg Ile Tyr Tyr Tyr Pro Glu Glu Val Leu Leu Gln Ala Tyr
465                 470                 475                 480
Asp Asn Ser His Pro Arg Thr Lys Arg Glu Ala Val Ser Leu Thr Leu
                485                 490                 495
Ala Val Leu Leu Gly Leu Gly Ile Thr Ala Gly Ile Gly Thr Gly Ser
                500                 505                 510
Thr Ala Leu Ile Lys Gly Pro Ile Asp Leu Gln Gln Gly Leu Thr Ser
        515                 520                 525
Leu Gln Ile Ala Ile Asp Ala Asp Leu Arg Ala Leu Gln Asp Ser Val
    530                 535                 540
Ser Lys Leu Glu Asp Ser Leu Thr Ser Leu Ser Glu Val Val Leu Gln
545                 550                 555                 560
Asn Arg Arg Gly Leu Asp Leu Leu Phe Leu Lys Glu Gly Gly Leu Cys
                565                 570                 575
Ala Ala Leu Lys Glu Glu Cys Cys Phe Tyr Ile Asp His Ser Gly Ala
            580                 585                 590
Val Arg Asp Ser Met Lys Lys Leu Lys Glu Lys Leu Asp Lys Arg Gln
        595                 600                 605
Leu Glu Arg Gln Lys Ser Gln Asn Trp Tyr Glu Gly Trp Phe Asn Asn
    610                 615                 620
```

```
Ser Pro Trp Phe Thr Thr Leu Leu Ser Thr Ile Ala Gly Pro Leu Leu
625                 630                 635                 640

Leu Leu Leu Leu Leu Leu Ile Leu Gly Pro Cys Ile Ile Asn Lys Leu
                645                 650                 655

Val Gln Phe Ile Asn Asp Arg Ile Ser Ala Cys
            660                 665

<210> SEQ ID NO 17
<211> LENGTH: 1019
<212> TYPE: DNA
<213> ORGANISM: Artificial Sequence
<220> FEATURE:
<223> OTHER INFORMATION: Nucleotide sequence encoding the packaging
      signal in the genome plasmid

<400> SEQUENCE: 17
aagctggcca gcaacttatc tgtgtctgtc cgattgtcta gtgtctatga ctgattttat      60
gcgcctgcgt cggtactagt tagctaacta gctctgtatc tggcggaccc gtggtggaac     120
tgacgagttc ggaacacccg ccgcaaccct gggagacgtc ccagggactc ggggggccg     180 tttttgtggc ccgacctgag tcctaaaatc ccgatcgttt aggactcttt ggtgcacccc    240
ccttagagga gggatatgtg gttctggtag gagacgagaa cctaaaacag ttcccgcctc    300
cgtctgaatt tttgctttcg gtttgggacc gaagccgcgc cgcgcgtctt gtctgctgca    360
gcatcgttct gtgttgtctc tgtctgactg tgtttctgta tttgtctgaa atatgggcc     420 cgggctagcc tgttaccact cccttaagtt tgaccttagg tcactggaaa gatgtcgagc    480
ggatcgctca caaccagtcg gtagatgtca agaagagacg ttgggttacc ttctgctctg    540
cagaatggcc aacctttaac gtcggatggc cgcgagacgg cacctttaac cgagacctca    600
tcacccaggt taagatcaag gtcttttcac ctggcccgca tggacaccca gaccaggtcc    660
cctacatcgt gacctgggaa gccttggctt ttgacccccc tccctgggtc aagccctttg    720
tacaccctaa gcctccgcct cctcttcctc catccgcccc gtctctcccc cttgaacctc    780
ctcgttcgac cccgcctcga tcctcccttt atccagccct cactccttct ctaggcgccc    840
ccatatggcc atatgagatc ttatatgggg caccccccgcc ccttgtaaac ttccctgacc    900
ctgacatgac aagagttact aacagcccct ctctccaagc tcacttacag gctctctact    960
tagtccagca cgaagtctgg agacctctgg cggcagccta ccaagaacaa ctggaccga    1019

<210> SEQ ID NO 18
<211> LENGTH: 573
<212> TYPE: DNA
<213> ORGANISM: Artificial Sequence
<220> FEATURE:
<223> OTHER INFORMATION: Nucleotide sequence of CMV promoter

<400> SEQUENCE: 18
agtaatcaat tacggggtca ttagttcata gcccatatat ggagttccgc gttacataac      60
ttacggtaaa tggcccgcct ggctgaccgc ccaacgaccc ccgcccattg acgtcaataa     120
tgacgtatgt tcccatagta acgccaatag ggactttcca ttgacgtcaa tgggtggagt    180
atttacggta aactgcccac ttggcagtac atcaagtgta tcatatgcca agtacgcccc    240
ctattgacgt caatgacggt aaatggcccg cctggcatta tgcccagtac atgaccttat    300
gggactttcc tacttggcag tacatctacg tattagtcat cgctattacc atgctgatgc    360
ggttttggca gtacatcaat gggcgtggat agcggtttga ctcacgggga tttccaagtc    420
tccaccccat tgacgtcaat gggagtttgt tttggcacca aaatcaacgg gactttccaa    480
```

```
aatgtcgtaa caactccgcc ccattgacgc aaatgggcgg taggcgtgta cggtgggagg     540
tctatataag cagagctggt ttagtgaacc gtc                                  573

<210> SEQ ID NO 19
<211> LENGTH: 1691
<212> TYPE: DNA
<213> ORGANISM: Artificial Sequence
<220> FEATURE:
<223> OTHER INFORMATION: Nucleotide sequence of CAG promoter

<400> SEQUENCE: 19
atagtaatca attacggggt cattagttca tagcccatat atggagttcc gcgttacata     60
acttacggta aatggcccgc ctggctgacc gcccaacgac ccccgcccat tgacgtcaat    120
aatgacgtat gttcccatag taacgccaat agggactttc cattgacgtc aatgggtgga    180
ctatttacgg taaactgccc acttggcagt acatcaagtg tatcatatgc caagtacgcc    240
ccctattgac gtcaatgacg gtaaatggcc cgcctggcat tatgcccagt acatgacctt    300
atgggacttt cctacttggc agtacatcta cgtattagtc atcgctatta ccatgcgtcg    360
aggtgagccc cacgttctgc ttcactctcc ccatctcccc cccctcccca ccccaatttt    420
tgtatttatt tatttttaa ttattttatg cagcgatggg ggcggggggg gggggggcgc     480
gcgccaggcg gggcggggcg gggcgagggg cgggcgggg cgaggcggag aggtgcggcg     540
gcagccaatc agagcggcgc gctccgaaag tttccttta tggcgaggcg gcggcggcgg    600
cggccctata aaaagcgaag cgcgcggcgg gcgggagtcg ctgcgttgcc ttcgccccgt    660
gccccgctcc gcgccgcctc gcgccgcccg ccccggctct gactgaccgc gttactccca    720
caggtgagcg gcgggacgg cccttctccc tccgggctgt aattagcgct tggtttaatg    780
acggctcgtt tcttttctgt ggctgcgtga agccttaaa gggctccggg agggcctttg    840 tgcgggggg agcggctcgg ggggtgcgtg cgtgtgtgtg tgcgtgggga gcgccgcgtg    900
cggcccgcgc tgcccggcgg ctgtgagcgc tgcgggcgcg gcgcggggct ttgtgcgctc    960
cgcgtgtgcg cgaggggagc gcgggccggg ggcggtgccc cgcggtgcgg ggggctgcg    1020 aggggaacaa aggctgcgtg cggggtgtgt gcgtgggggg gtgagcaggg ggtgtgggcg   1080
cggcggtcgg gctgtaaccc ccccctggca ccccctccc cgagttgctg agcacggccc    1140
ggcttcgggt gcgggctcc gtgcgggcg tggcgcgggg ctcgccgtgc cgggcggggg    1200
gtggcggcag gtggggtgc cgggcggggc ggggccgcct cgggccgggg agggctcggg    1260 ggagggcgc ggcggccccg gagcgccggc ggctgtcgag gcgcggcgag ccgcagccat    1320 tgcctttat ggtaatcgtg cgagagggcg cagggacttc ctttgtccca aatctggcgg    1380
agccgaaatc tgggaggcgc cgccgcaccc cctctagcgg gcgcgggcga agcggtgcgg    1440
cgccggcagg aaggaaatgg gcggggaggg ccttcgtgcg tcgccgcgcc gccgtcccct    1500
tctccatctc cagcctcggg gctgccgcag ggggacggct gccttcgggg gggacgggc     1560 agggcgggt tcggcttctg gcgtgtgacc ggcggcttta gagcctctgc taaccatgtt    1620
catgccttct tctttttcct acagctcctg ggcaacgtgc tggttgttgt gctgtctcat    1680
cattttggca a                                                        1691

<210> SEQ ID NO 20
<211> LENGTH: 167
<212> TYPE: DNA
<213> ORGANISM: Artificial Sequence
<220> FEATURE:
```

<223> OTHER INFORMATION: Nucleotide sequence of Rabbit B-globin polyA

<400> SEQUENCE: 20

```
ctggtgtggc caatgccctg gctcacaaat accactgacg atcttttcc ctctgccaaa    60
aattatgggg acatcatgaa gccccttgag catctgactt ctggctaata aaggaaattt   120
attttcattg caatagtgtg ttggaatttt ttgtgtctct cactcgg                167
```

<210> SEQ ID NO 21
<211> LENGTH: 642
<212> TYPE: DNA
<213> ORGANISM: Artificial Sequence
<220> FEATURE:
<223> OTHER INFORMATION: Nucleotide sequence of BGIntron

<400> SEQUENCE: 21

```
agatcgcctg gagacgccat ccacgctgtt ttgacctcca tagaagacac cgggaccgat    60
ccagcctccc ctcgaagctt acatgtggta ccgagctcgg atcctgagaa cttcagggtg   120
agtctatggg acccttgatg ttttctttcc ccttcttttc tatggttaag ttcatgtcat   180
aggaagggga gaagtaacag ggtacacata ttgaccaaat cagggtaatt ttgcatttgt   240
aattttaaaa aatgctttct tcttttaata tactttttg tttatcttat ttctaatact   300
ttccctaatc tctttctttc agggcaataa tgatacaatg tatcatgcct ctttgcacca   360
ttctaaagaa taacagtgat aatttctggg ttaaggcaat agcaatattt ctgcatataa   420
atatttctgc atataaattg taactgatgt aagaggtttc atattgctaa tagcagctac   480
aatccagcta ccattctgct tttatttat ggttgggata aggctggatt attctgagtc   540
caagctaggc ccttttgcta atcatgttca tacctcttat cttcctccca cagctcctgg   600
gcaacgtgct ggtctgtgtg ctggcccatc actttggcaa ag                    642
```

<210> SEQ ID NO 22
<211> LENGTH: 1047
<212> TYPE: DNA
<213> ORGANISM: Artificial Sequence
<220> FEATURE:
<223> OTHER INFORMATION: Nucleotide sequence of Ferritin promoter

<400> SEQUENCE: 22

```
agtaatcaat tacggggtca ttagttcata gcccatatat ggagttccgc gttacataac    60
ttacggtaaa tggcccgcct ggctgaccgc ccaacgaccc ccgcccattg acgtcaataa   120
tgacgtatgt tcccatagta acgccaatag ggactttcca ttgacgtcaa tgggtggagt   180
atttacggta aactgcccac ttggcagtac atcaagtgta tcatatgcca agtacgcccc   240
ctattgacgt caatgacggt aaatggcccg cctggcatta tgcccagtac atgaccttat   300
gggactttcc tacttggcag tacatctacg tattagtcat cgctattacc atgctgatgc   360
ggttttggca gtacatcaat gggcgtggat agcggtttga ctcacgggga tttccaagtc   420
tccaccccat tgacgtcaat gggagtttgt tttggcacca aaatcaacgg gactttccaa   480
aatgtcgtaa caactccgcc ccattgacgc aaatgggcgg taggcgtgta cggtgggagg   540
tctatataag cagagctggt ttagtgaacc ggatccccg gctgcagga atttatgaaa   600
tcctttatgg gggaccccc ctttgtcaa ccttgctcaa ttccttctcc cctccgatc   660
ctaagactga tttacaagcc cgactaaaag ggctgcaagc ggtgcaggcc caaatctgga   720
caccctggc cgaattgtac cggccaggac atccacaaac tagccaccca tttcaggtgg   780
gagactccgt gtacgtccgg cggcacgcct ctcaaggatt ggagcctcgt tggaagggac   840
```

```
cttacatcgt cctgctgacc acgcccaccg ccataaaggt tgacgggatc gccgcctgga    900
ttcacgcatc gcacgccaag gcagcccaa aaaccctgg accagaaact cccaaaacct     960
ggaagctccg ccgttcggag aaccctctta agataagact ctcccgtgtc tgactgctaa  1020
tccaccttgt ccctgtacta acccaaa                                       1047

<210> SEQ ID NO 23
<211> LENGTH: 191
<212> TYPE: DNA
<213> ORGANISM: Artificial Sequence
<220> FEATURE:
<223> OTHER INFORMATION: Nucleotide sequence of CMV-RD114UTR

<400> SEQUENCE: 23
actagttccg ccagagcgcg cgagggcctc cagcggccgc ccctccccca cagcaggggc     60
ggggtcccgc gcccaccgga aggagcgggc tcggggcggg cggcgctgat tggccgggc    120 gggcctgacg ccgacgcggc tataagagac cacaagcgac ccgcagggcc agacgttctt   180
cgccgaagct t                                                         191

<210> SEQ ID NO 24
<211> LENGTH: 192
<212> TYPE: DNA
<213> ORGANISM: Artificial Sequence
<220> FEATURE:
<223> OTHER INFORMATION: Sv40 PolyA

<400> SEQUENCE: 24
cagacatgat aagatacatt gatgagtttg gacaaaccac aactagaatg cagtgaaaaa     60
aatgctttat ttgtgaaatt tgtgatgcta ttgctttatt tgtaaccatt ataagctgca    120
ataaacaagt taacaacaac aattgcattc attttatgtt tcaggttcag ggggaggtgt   180
gggaggtttt tt                                                        192

<210> SEQ ID NO 25
<211> LENGTH: 476
<212> TYPE: DNA
<213> ORGANISM: Artificial Sequence
<220> FEATURE:
<223> OTHER INFORMATION: RD114 Intron

<400> SEQUENCE: 25 gatccccgg gctgcaggaa tttatgaaat cctttatggg ggaccccccc ctttgtcaac      60
cttgctcaat tccttctccc cctccgatcc taagactgat ttacaagccc gactaaaagg    120
gctgcaagcg gtgcaggccc aaatctggac accctggcc gaattgtacc ggccaggaca    180 tccacaaaact agccacccat ttcaggtggg agactccgtg tacgtccggc ggcaccgctc   240
tcaaggattg gagcctcgtt ggaagggacc ttacatcgtc ctgctgacca cgcccaccgc    300
cataaaggtt gacgggatcg ccgcctggat tcacgcatcg cacgccaagg cagccccaaa    360
aacccctgga ccagaaactc ccaaaacctg gaagctccgc cgttcggaga accctcttaa    420
gataagactc tcccgtgtct gactgctaat ccaccttgtc cctgtactaa cccaaa         476

<210> SEQ ID NO 26
<211> LENGTH: 999
<212> TYPE: DNA
<213> ORGANISM: Artificial Sequence
<220> FEATURE:
<223> OTHER INFORMATION: MEF1 Intron
```

```
<400> SEQUENCE: 26
gccgtcagaa cgcaggtgag gggcgggtgt ggcttccgcg ggccgccgag ctggaggtcc      60
tgctccgagc gggccgggcc ccgctgtcgt cggcggggat tagctgcgag cattcccgct     120
tcgagttgcg ggcggcgcgg gaggcagagt gcgaggccta gcggcaaccc cgtagcctcg     180
cctcgtgtcc ggcttgaggc ctagcgtggt gtccgcgccg ccgccgcgtg ctactccggc     240
cgcactctgg tcttttttt ttttgttgtt gttgccctgc tgccttcgat tgccgttcag     300 caatagggc taacaaaggg agggtgcggg gcttgctcgc ccggagcccg gagaggtcat     360
ggttggggag gaatggaggg acaggagtgg cggctgggc ccgcccgcct tcggagcaca     420
tgtccgacgc cacctggatg gggcgaggcc tggggttttt cccgaagcaa ccaggctggg     480
gttagcgtgc cgaggccatg tggccccagc acccggcacg atctggcttg gcggcgccgc     540
gttgccctgc ctccctaact agggtgaggc catcccgtcc ggcaccagtt gcgtgcgtgg     600
aaagatggcc gctcccgggc cctgttgcaa ggagctcaaa atggaggacg cggcagcccg     660
gtggagcggg cgggtgagtc acccacacaa aggaagaggg cctggtccct caccggctgc     720
tgcttcctgt gacccccgtgg tcctatcggc cgcaatagtc acctcgggct tttgagcacg     780
gctagtcgcg gcgggggag gggatgtaat ggcgttggag tttgttcaca tttggtgggt     840
ggagactagt caggccagcc tggcgctgga agtcattttt ggaatttgtc cccttgagtt     900
ttgagcggag ctaattctcg ggcttcttag cggttcaaag gtatctttta aacccttttt     960
taggtgttgt gaaaaccacc gctaattcaa agcaaccgg                           999
```